(12) United States Patent
Tsai et al.

(10) Patent No.: US 11,369,579 B2
(45) Date of Patent: *Jun. 28, 2022

(54) POLYMORPHIC FORMS OF SODIUM BENZOATE AND USES THEREOF

(71) Applicant: SyneuRx International (Taiwan) Corp., New Taipei (TW)

(72) Inventors: Guochuan Emil Tsai, Pasadena, CA (US); Ching-Cheng Wang, New Taipei (TW); Tien-Lan Hsieh, New Taipei (TW)

(73) Assignee: SyneuRx International (Taiwan) Corp., New Taipei (TW)

( * ) Notice: Subject to any disclaimer, the term of this patent is extended or adjusted under 35 U.S.C. 154(b) by 0 days.

This patent is subject to a terminal disclaimer.

(21) Appl. No.: 16/393,762

(22) Filed: Apr. 24, 2019

(65) Prior Publication Data

US 2019/0274984 A1 Sep. 12, 2019

Related U.S. Application Data

(63) Continuation-in-part of application No. PCT/CN2017/107436, filed on Oct. 24, 2017, which
(Continued)

(51) Int. Cl.
*A61K 31/192* (2006.01)
*A61P 25/00* (2006.01)

(52) U.S. Cl.
CPC ............ *A61K 31/192* (2013.01); *A61P 25/00* (2018.01)

(58) Field of Classification Search
None
See application file for complete search history.

(56) References Cited

U.S. PATENT DOCUMENTS

| 3,498,989 A | 3/1970 | Sallay et al. |
| 3,870,715 A | 3/1975 | Hansl |

(Continued)

FOREIGN PATENT DOCUMENTS

| DE | 4340273 | 6/1995 |
| WO | WO 01/09143 A1 | 2/2001 |

(Continued)

OTHER PUBLICATIONS

Martin CrystEngComm vol. 18, pp. 5811-5817. (Year: 2016).*

(Continued)

*Primary Examiner* — Katherine Peebles
(74) *Attorney, Agent, or Firm* — McDermott Will & Emery LLP

(57) ABSTRACT

The present disclosure provides polymorphic forms of sodium benzoate with a X-ray diffraction pattern comprising characteristic peaks at a reflection angle 2θ of approximately 5.9, 30.2, and 31.2 degrees; or a X-ray diffraction pattern comprising characteristic peaks at a reflection angle 2θ of approximately 3.7, 5.9, and 26.6 degrees. The present disclosure provides polymorphic forms of sodium benzoate with a X-ray diffraction pattern comprising characteristic peaks at a reflection angle 2θ of approximately 3.6, 7.5, 26.6, and 29.4 degrees. Also provided herein are methods of preparing the polymorphic forms of sodium benzoate and uses thereof in treating and/or reducing the risk for a neuropsychiatric disorder (e.g., schizophrenia, psychotic disorders, depressive disorders, or Alzheimer's disease).

16 Claims, 29 Drawing Sheets

Related U.S. Application Data is a continuation-in-part of application No. 15/452,137, filed on Mar. 7, 2017, now Pat. No. 10,336,679.

(60) Provisional application No. 62/412,160, filed on Oct. 24, 2016.

(56) References Cited

U.S. PATENT DOCUMENTS

| | | |
|---|---|---|
| 4,041,174 A | 8/1977 | Sapse |
| 4,956,363 A | 8/1990 | Wulfert et al. |
| 5,198,217 A | 3/1993 | Vedros |
| 5,453,425 A | 9/1995 | Francois et al. |
| 5,616,587 A | 4/1997 | Francois et al. |
| 5,658,900 A | 8/1997 | Boireau et al. |
| 6,255,089 B1 | 7/2001 | Teitler et al. |
| 6,569,848 B1 | 5/2003 | Davis et al. |
| 6,746,678 B1 | 6/2004 | Shapiro |
| RE39,181 E | 7/2006 | Francois et al. |
| 7,094,930 B2 | 8/2006 | Quallich et al. |
| 7,166,725 B2 | 1/2007 | Fang et al. |
| 7,811,604 B1 | 10/2010 | Ahmed et al. |
| 9,649,304 B2 | 5/2017 | Tsai |
| 9,675,604 B2 | 6/2017 | Tsai |
| 10,098,861 B1 | 10/2018 | Tsai et al. |
| 10,149,845 B2 | 12/2018 | Tsai |
| 2001/0044446 A1* | 11/2001 | Phillips ............... A61K 31/485 514/282 |
| 2003/0185754 A1 | 10/2003 | Cohen et al. |
| 2004/0087658 A1 | 5/2004 | Moebius |
| 2004/0138197 A1 | 5/2004 | Maw et al. |
| 2004/0138298 A1 | 7/2004 | Mermelstein et al. |
| 2005/0272721 A1 | 12/2005 | Keltjens |
| 2006/0204486 A1 | 9/2006 | Pyke et al. |
| 2008/0045512 A1 | 2/2008 | Duplantier et al. |
| 2008/0070984 A1 | 3/2008 | Tran |
| 2010/0189818 A1 | 7/2010 | Tsai et al. |
| 2011/0045065 A1 | 2/2011 | Vyas et al. |
| 2015/0045312 A1* | 2/2015 | Neary ............... A61K 31/497 514/21.91 |
| 2016/0008476 A1 | 1/2016 | Embrechts et al. |
| 2017/0181989 A1 | 6/2017 | Tsai |
| 2017/0189358 A1 | 7/2017 | Tsai |
| 2018/0036267 A1 | 2/2018 | Tsai et al. |

FOREIGN PATENT DOCUMENTS

| | | |
|---|---|---|
| WO | 2002/066672 | 8/2002 |
| WO | WO 03/033508 A1 | 4/2003 |
| WO | 2005/000205 | 1/2005 |
| WO | 2005/117911 | 12/2005 |
| WO | 2006/129160 | 12/2006 |
| WO | 2007/093829 | 8/2007 |
| WO | 2010/085452 | 7/2010 |
| WO | 2015/147742 A1 | 10/2015 |

OTHER PUBLICATIONS

Howard. Organic Process Research & Development vol. 13, pp. 590-597. (Year: 2009).*
Inoue and Hirasawa, Journal of Crystal Growth vol. 380 pp. 169-175; publication year 2013.
Motta, [Application of paraaminobenzoic acid in three groups of agitated, apathetic and confused schizophrenics] Rass Studi Psichiatr. 1953;42(4):731-40. Undetermined Language. Italian.
Quastel et al., Faulty Detoxication in Schizophrenia. Lancet. 1938;232:301-305.
Lin et al., PM405. Sodium Benzoate Add-on Treatment for Refractory Schizophrenia: A Randomized, Double-Blind, Placebo-Controlled Trial Int. J. Neuropsychopharmacol. Jun. 2016; 19 (Suppl 1 ): 47.
Lin et al., Sodium Benzoate, a D-Amino Acid Oxidase Inhibitor, Added to Clozapine for the Treatment of Schizophrenia: A Randomized, Double-Blind, Placebo-Controlled Trial. Biological Psychiatry, Available online Dec. 26, 2017, pp. 1-11.
Stern et al., Ageing and detoxication; studies in hippuric acid synthesis during psychoses of the involutional and old age group. Am J Psychiatry Nov. 1945;102:325-9.
Howard et al., A Process Analytical Technology Based Investigation of the Polymorphic Transformations during the Antisolvent Crystallization of Sodium Benzoate from IPA/Water Mixture. Crystal Growth & Design. 2009;9(9):3964-75.
Butterhof et al., Microphase Separation with Small Amphiphilic Molecules: Crystal Structure of Preservatives Sodium Benzoate (E 211) and Potassium Benzoate (E 212). Z. Anorg. Allg. Chem. 2013;639(15):2816-21.
FDA Orange Book: Approved Drug Products with Therapeutic Equivalence, Information related to Risderidal/Risperdal. 2014.
[No Author Listed] Janssen Pharmaceutical Products, L.P. Drug information for Risderidal/Risperdal. 2003;1-39.
Adage et al., In vitro and in vivo pharmacological profile of AS057278, a selective d-amino acid oxidase inhibitor with potential anti-psychoticproperties, Mar. 2008, pp. 200-214, Eur Neuropsychopharmacol.
Berge et al., Pharmaceutical Salts. J Pharmaceutical Sciences. 1977;66(1 ): 1-19.
Dorwald. Side reactions in organic synthesis. 2006.
Fang, Pharmaceutics. China Medical Science Technology Press. Mar. 31, 2016. 49-50.
Frisell et al. Flavoenzyme catalysis. Substrate-competitive inhibition of D-amino acid oxidase. J Biological Chemistry. 1956;223:75-83.
Gaisler-Salomon et al. Abnormally persistent latent inhibition induced by MK801 is reversed by risperidone and by positive modulations of NMDA receptor function; differential efficacy depending on the stage of the task at which they areadministered, Psychopharmacology (2008) 196:255-67.
Ishiyama et al. Lurasidone (SM-13496), a novel atypical antipsychotic drug, reverses MK-801-induced impairment of learning and memory in the rat passive-avoidance test, European Journal of Pharmacology 572 (2007) pp. 160-170.
Lin et al., Synthesis and Purification of Sodium Benzoate. Shandong Science. Mar. 31, 1991;4:68.
Matin et al. Dextromethorphan-Induced Near-Fatal Suicide Attempt in a Slow Metabolizer at Cytochrome P450 2D6. American J Geriatric Pharmacotherapy. Jun. 2007;5(2):162-165.
McCracken et al., Risperidone in children with autism and serious behavioral problems. N. Eng. J. Med. Aug. 1, 2002;347(5).
McLean et al. A preliminary investigation into the effects of antipsychotics on sub-chronic phencyclidine-induced deficits in attentional set-shifting in female rats, Behavioral Brain Research 189 (2008) pp. 152-158.
Millan et al., Overview of drug classes proposed for the treatment of cognitive impairments in psychiatric disorders. table 2, Feb. 2012. 1-7. Retrieved from www.nature.com/nrd/journal/v11/n2/fig_tab/nrd3628_T2.htm 1.
Osol, [Editor], Chapter 27: Structure-Activity Relationship and Drug Design. Remington's Pharmaceutical Sciences (Sixteenth Edition). Mack Publishing. 1980;420-435.
Smith et al., The Therapeutic Potential of D-Amino Acid Oxidase (DAAO) Inhibitors, 2010;4:3-9, The Open Medicinal Chemistry J.
Su et al. Risperidone attenuates MK-801-induced hyperlocomotion in mice via the blockade of serotonin 5-HT2A/2C receptors. European J Pharmacology. 2007;654:123-130.
Tsai et al., Strategies to Enhance N-Methyl-D-Aspartate Receptor-Mediated Neurotransmission in Schizophrenia, a Critical Review and Meta-Analysis. Curr. Pharm. Design, 2010;16:1-16.
Zhao et al.; Inhibition of D-Amino-Acid Oxidase Activity Induces Pain Relief in Mice; Cell Mol Neurobiol (2008) 28:581-591.
Zhu et al., Investigation of the Therapy of TD with ADHD. Department of Pediatrics of Shanghai Baoshan Centre Hospital, Shanghai, China, Guide of China Medicine, Oct. 2008;6(19):1-7.
Butterhof C, Milius W, Breu J. Co-crystallisation of benzoic acid with sodium benzoate: the significance of stoichiometry. CrystEngComm. 2012;14(11):3945-50.

(56) References Cited

OTHER PUBLICATIONS

Hashimoto K. Targeting of NMDA receptors in new treatments for schizophrenia. Expert opinion on therapeutic targets. Sep. 1, 2014;18(9):1049-63.

Lane HY, Lin CH, Green MF, Hellemann G, Huang CC, Chen PW, Tun R, Chang YC, Tsai GE. Add-on treatment of benzoate for schizophrenia: a randomized, double-blind, placebo-controlled trial of D-amino acid oxidase inhibitor. JAMA psychiatry. Dec. 1, 2013;70(12):1267-75.

Lin, et al. Synthesis and Purification of Sodium Benzoate, Shandong Science, vol. 4 No. 1, 1999, pp. 68-69, and English translation of abstract.

Caira, Crystalline Polymorphism of Organic Compounds. Design of Organic Solids. Feb. 26, 1999;163-208.

\* cited by examiner

POLYMORPHIC FORMS OF SODIUM BENZOATE AND USES THEREOF

RELATED APPLICATION

The present application claims priority under 35 U.S.C. §§ 120 and 365(c) to and is a continuation-in-part of international PCT Application, PCT/CN2017/107436, filed Oct. 24, 2017, which claims priority to U.S. application Ser. No. 15/452,137, filed Mar. 7, 2017 and U.S. Provisional Application No. 62/412,160, filed Oct. 24, 2016, each of which is herein incorporated by reference in the entirety.

BACKGROUND OF THE INVENTION

The central nervous system (CNS) includes the brain and spinal cord. The CNS is vulnerable to various disorders, which may be caused by various factors, including genetic, trauma, infections, degeneration, structural defects and/or damages, tumors, blood flow disruption, and autoimmune disorders. Symptoms of a CNS disorder would depend on the area of the nervous system that is involved and the cause of the disorder.

The development of effective therapies for CNS disorders has lagged behind other therapeutic areas due to the complexity of such disorders and the lack of efficient technology for delivering therapeutic agents through the blood-brain barrier. As such, it is of great interest to develop new treatment approaches for CNS disorders.

SUMMARY OF THE INVENTION

Provided herein are novel polymorphic forms of sodium benzoate, compositions and kits comprising such, methods of making such, and uses of the polymorphic forms of sodium benzoate for treating and/or reducing the risk for a neuropsychiatric disorder (e.g., schizophrenia, psychotic disorders, pain, or Alzheimer's disease). Also provided herein are pharmaceutical compositions comprising a sodium benzoate compound and clozapine; and a method for preventing, treating and/or reducing the risk of a neuropsychiatric disorder by administering such pharmaceutical compositions.

In one aspect, the present disclosure provides a polymorphic form of sodium benzoate which has an X-ray powder diffraction pattern comprising characteristic peaks at a reflection angle 2θ of approximately 5.9, 30.2, and 31.2 degrees, which may be determined by a period of a scan speed of about 0.1 to 0.3 seconds per step. In certain embodiments, the X-ray powder diffraction pattern of the polymorphic form of sodium benzoate may further comprise characteristic peaks at a reflection angle 2θ of approximately 3.6, 7.2, 7.5, 14.9, 15.9, 16.6, 17.6, 18.8, 20.4, 22.9, 23.7, 25.1, 25.8, 26.6, 28.1, 29.1, 29.4, 29.7, 31.5, 32.9, 34.2, and 35.7 degrees. In some embodiments, the X-ray powder diffraction pattern of the polymorphic form of sodium benzoate may further comprise characteristic peaks at a reflection angle 2θ of approximately 3.7, 6.8, 7.5, 11.3, 11.6, 17.6, 22.7, 23.5, 26.2, 27.6, 28.3, 29.3, 32.2, 32.9, 34.0, and 35.7 degrees. In some embodiments, the X-ray powder diffraction pattern of the polymorphic form of sodium benzoate may further comprise characteristic peaks at a reflection angle 2θ of approximately 3.7, 6.3, 6.8, 7.5, 11.7, 17.7, 23.6, 24.5, 26.5, 27.0, 27.7, 28.4, 29.0, 31.0, 32.3, 34.2, and 35.9 degrees. In some embodiments, the X-ray powder diffraction pattern of the polymorphic form of sodium benzoate may further comprise characteristic peaks at a reflection angle 2θ of approximately 4.3, 7.1, 8.6, 10.1, 10.7, 12.9, 13.8, 14.4, 17.2, 17.7, 18.5, 21.5, 22.0, 22.6, 23.7, 25.1, 25.9, 26.2, 26.9, 27.9, 28.2, 28.8, 29.1, 29.7, 33.2, 34.9, 35.8, 36.1, and 39.3 degrees.

In another aspect, the present disclosure provides a polymorphic form of sodium benzoate which has an X-ray powder diffraction pattern comprising characteristic peaks at a reflection angle 2θ of approximately 3.7, 5.9, and 26.6 degrees. In some embodiments, the X-ray diffraction pattern may be determined by a period of a scan speed of about 0.1 to 0.3 seconds per step. In some embodiments, a X-ray powder diffraction pattern of the polymorphic form of sodium benzoate may further comprise characteristic peaks at a reflection angle 2θ of approximately 5.5, 6.7, 7.4, 12.5, 14.7, 16.5, 17.7, 22.0, 23.6, 24.6, 25.8, 27.6, 28.4, 30.2, 31.1, 32.3, 34.3, and 35.9 degrees. In some embodiments, the X-ray powder diffraction pattern of the polymorphic form of sodium benzoate may further comprise characteristic peaks at a reflection angle 2θ of approximately 6.6, 7.4, 9.4, 11.2, 12.5, 22.8, 25.1, 26.3, 28.2, 29.5, 30.2, 31.1, 31.2, 33.0, and 34.0 degrees.

In one aspect, the present disclosure provides a polymorphic form of sodium benzoate which has an X-ray powder diffraction pattern comprising characteristic peaks at a reflection angle 2θ of approximately 3.6, 7.5, 26.6, and 29.4 degrees; wherein the X-ray diffraction pattern is determined by a period of a scan speed of about 1.0 second per step. In certain embodiments, the X-ray powder diffraction pattern of the polymorphic form of sodium benzoate may further comprise characteristic peaks at a reflection angle 2θ of approximately 5.9, 6.8, 17.6, 27.6, 30.2, 30.9, and 32.3 degrees. In certain embodiments, the X-ray powder diffraction pattern of the polymorphic form of sodium benzoate may further comprise characteristic peaks at a reflection angle 2θ of approximately 11.1, 14.9, 26.2, 32.9, and 35.7 degrees. In certain embodiments, the X-ray powder diffraction pattern of the polymorphic form of sodium benzoate may further comprise characteristic peaks at a reflection angle 2θ of approximately 12.4 and 22.9 degrees, In certain embodiments, the X-ray powder diffraction pattern of the polymorphic form of sodium benzoate may further comprise characteristic peaks at a reflection angle 2θ of approximately 4.2, 8.5, 9.2, 11.1, 11.7, 12.4, 14.9, 15.9, 16.6, 18.8, 19.4, 20.4, 21.6, 22.9, 23.7, 24.7, 25.1, 25.8, 26.1, 28.1, 29.1, 29.7, 30.6, 31.5, 32.9, 33.6, 34.2, 35.7, 38.6, and 39.6 degrees. In certain embodiments, the X-ray powder diffraction pattern of the polymorphic form of sodium benzoate may further comprise characteristic peaks at a reflection angle 2θ of approximately 8.9, 11.1, 14.9, 22.7, 23.5, 24.8, 26.2, 28.3, 32.9, 34.0, 35.7, and 37.8 degrees. In certain embodiments, the X-ray powder diffraction pattern of the polymorphic form of sodium benzoate may further comprise characteristic peaks at a reflection angle 2θ of approximately 6.3, 9.4, 11.7, 16.4, 23.6, 24.5, 25.7, 28.4, 29.0, 30.4, 31.0, 31.2, 34.2, 35.4, and 35.9 degrees. In certain embodiments, the X-ray powder diffraction pattern of the polymorphic form of sodium benzoate may further comprise characteristic peaks at a reflection angle 2θ of approximately 4.2, 5.6, 5.9, 6.6, 8.4, 9.4, 12.5, 17.6, 18.6, 21.6, 22.8, 23.6, 25.1, 27.1, 28.2, 30.2, 31.1, 31.3, 32.0, 34.0, and 38.0 degrees.

In another aspect, the present disclosure provides compositions (e.g., a pharmaceutical composition, a nutraceutical composition, a health food, or a medical food) including (i) an effective amount of one or more of the polymorphic forms of sodium benzoate described herein, and (ii) a carrier, excipient, diluent, binder, additive, filler, lubricant, or a mixture thereof. An effective amount described herein may be a therapeutically effective amount or prophylactically effective amount.

In yet another aspect, the present disclosure provides methods for treating and/or reducing the risk for a neuropsychiatric disorder (e.g., schizophrenia, psychotic disorders, depression, pain, Alzheimer's disease, or dementia), the method comprising administering to a subject in need of the treatment an effective amount of any of the compositions described herein.

A target neuropsychiatric disorder can include, but is not limited to, schizophrenia, psychotic disorders, Alzheimer's disease, dementia, frontotemporal dementia, mild cognitive impairment, benign forgetfulness, closed head injury, autistic spectrum disorder, Asperger's disorder, attention deficit hyperactivity disorders, obsessive compulsive disorder, tic disorders, childhood learning disorders, premenstrual syndrome, depression, suicidal ideation, suicidal behavior, bipolar disorder, anxiety disorders, post-traumatic stress disorder, chronic pain, eating disorders, addiction disorders, personality disorders, Parkinson's disorder, Huntington's disorder, multiple sclerosis, or amyotrophic lateral sclerosis.

In any of the treatment methods as described herein, the subject being treated can be a mammal (e.g., human or non-human mammal). For example, the subject can be a human patient having or suspected of having a target disease as described herein.

Another aspect of the present disclosure relates to kits comprising a container in which a polymorphic form of sodium benzoate, or composition thereof, as described herein, is placed. The kits described herein may include a single dose or multiple doses of the polymorph or composition. The kits may be useful in a method of the disclosure. In certain embodiments, the kit further includes instructions for using the polymorph or composition.

In yet another aspect, the present disclosure provides polymorphic forms of sodium benzoate and compositions described herein for use in treating and/or reducing the risk for a neuropsychiatric disorder as described herein. The present disclosure also provides uses of one or more of the polymorphic form of sodium benzoate for manufacturing a medicament for use in treating a target neuropsychiatric disorder as described herein.

The present disclosure also provides methods for preparing the novel polymorphic forms of sodium benzoate described herein.

In some embodiments, provided herein is a method for preparing a polymorphic form of sodium benzoate, the method comprising: (i) dissolving an excess amount of sodium benzoate in a single or mixed solvent to form a saturated solution at ambient pressure and temperature, (ii) filtrating the saturated solution to remove insoluble components; (iii) evaporating the saturated solution obtained in (ii) to form a polymorphic form of sodium benzoate at ambient or reduced pressure and at an elevated temperature of approximately 40-110° C.; and (vi) collecting the polymorphic form of sodium benzoate formed in (iii).

In other embodiments, provided herein is a method for preparing a polymorphic form of sodium benzoate, the method comprising: (i) dissolving sodium benzoate in a single or mixed solvent at a temperature ranging from about 50-110° C. to form a solution; (ii) cooling the solution to ambient temperature while stirring; (iii) placing the cooled solution at ambient temperature to allow formation of a polymorphic form of sodium benzoate; and (iv) collecting the polymorphic form of sodium benzoate formed in (iii).

In yet other embodiments, provided herein is a method for preparing a polymorphic form of sodium benzoate, the method comprising: (i) placing sodium benzoate at a relative humidity (RH) greater than about 90% for about 1 to 10 days, during which a polymorphic form of sodium benzoate forms; and (ii) collecting the polymorphic form of sodium benzoate formed in (i).

In other embodiments, provided herein is a method for preparing a polymorphic form of sodium benzoate, the method comprising: (i) dissolving sodium benzoate in a polar solvent, to form a slurry; (ii) stirring the slurry for approximately 10 minutes to approximately 6 days to produce the polymorphic form of sodium benzoate, and (iii) filtering and collecting the polymorphic form of sodium benzoate thus formed. In some embodiments, the sodium benzoate is dissolved in methanol in step (i) of the method. In some embodiments, the polar solvent may comprise methanol, acetonitrile, or isobutanol, or a combination thereof. In some embodiments, the polar solvent comprises water. In some embodiments, the polar solvent does not comprise water. In some embodiments, the polar solvent comprises methanol, acetonitrile, or isobutanol, or a combination thereof, and no water.

In some embodiments, in step (i), the solvent comprises methanol and the method further comprises adding acetonitrile after the sodium benzoate is dissolved in the solvent in step (i). In some embodiments, the sodium benzoate is dissolved in methanol in step (i) of the method and wherein in step (ii) the stirring of the slurry is for approximately 10 minutes, or for approximately 2 days to approximately 6 days. In some embodiments, the sodium benzoate is dissolved in methanol in step (i) of the method and wherein in step (ii) the stirring of the slurry is for approximately 10 minutes, or for approximately 2 days to approximately 4 days. In some embodiments, the sodium benzoate is dissolved in methanol in step (i) of the method and wherein in step (ii) the stirring of the slurry is for approximately 10 minutes. In some embodiments, in step (i), the solvent comprises acetonitrile. In some embodiments, the sodium benzoate is dissolved in acetonitrile in step (i) of the method and wherein in step (ii) the stirring of the slurry is for approximately 2 days. In some embodiments, the sodium benzoate is dissolved in acetonitrile in step (i) of the method and wherein in step (ii) the stirring of the slurry is for approximately 2 days to approximately 4 days. In some embodiments, in step (i), the solvent comprises isobutanol. In some embodiments, the sodium benzoate is dissolved in isobutanol in step (i) of the method and wherein in step (ii) the stirring of the slurry is for approximately 2 days to approximately 6 days. In some embodiments, the sodium benzoate is dissolved in isobutanol in step (i) of the method and wherein in step (ii) the stirring of the slurry is for approximately 4 days to approximately 6 days. In some embodiments, the sodium benzoate is dissolved in isobutanol in step (i) of the method and wherein in step (ii) the stirring of the slurry is for approximately 6 days. In some embodiments, wherein the sodium benzoate is dissolved in methanol in step (i) of the method, wherein step (ii) comprises further adding the acetonitrile after the sodium benzoate is dissolved in methanol, and wherein in step (ii) the stirring of the slurry is for approximately 2 days. In some embodiments, wherein the sodium benzoate is dissolved in methanol in step (i) of the method, wherein step (ii) comprises further adding the acetonitrile after the sodium benzoate is dissolved in methanol, and wherein in step (ii) the stirring of the slurry is for approximately 2 days to approximately 6 days. In some embodiments, in the process, the sodium benzoate is dissolved in methanol in step (i) of the method, the process further comprises adding acetonitrile after the sodium benzoate is dissolved in methanol in step (i) of the method, and wherein in step (ii) the stirring of the slurry is for approximately 2 days to approximately 4 days.

Alternatively, one or more polymorphic forms of sodium benzoate described herein can be prepared by a method comprising: (i) preparing a slurry of sodium benzoate in a single or mixed solvent; (ii) stirring the slurry for 6 hours to 10 days, during which a polymorphic form of sodium benzoate forms; and (iii) collecting the polymorphic form of sodium benzoate formed in (ii).

In other examples, such a method may comprise: (i) dissolving sodium benzoate in a single or mixed solvent to form a solution; (ii) mixing an anti-solvent with the solution obtained in (i) to form a slurry, wherein the volume ratio between the anti-solvent and the solution in (i) is about 4:1 to 15:1; (iii) stirring the slurry at ambient pressure and temperature for about 2-10 days, during which a polymorphic form of sodium benzoate forms; and (iv) collecting the polymorphic form of sodium benzoate formed in (iii).

In still other examples, the preparation method may comprise: (i) preparing a slurry of any suitable polymorphic form of sodium benzoate as described herein in a single or mixed solvent in the presence of about 2-10% of water; (ii) stirring the slurry at ambient pressure and temperature for about 2 to 10 days, during which a polymorphic form of sodium benzoate forms; and (iii) collecting the polymorphic form of sodium benzoate formed in (iii).

In yet another aspect, the present disclosure provides a pharmaceutical composition comprising 50 to 1000 mg of a sodium benzoate compound and 25 to 300 mg of clozapine in a solid dosage form, e.g., tablet, dragee, capsule, pill, powder, or granule. In some embodiments, the solid dosage form may further comprise a film coating.

The aforementioned sodium benzoate compound can be in amorphous form, in polymorphic forms, or both. In some embodiments, the sodium benzoate compound comprises any of the polymorphic forms of sodium benzoate described herein (e.g., polymorph #4).

Any of the pharmaceutical compositions described herein may further comprise a pharmaceutically acceptable excipient, which may be boric acid, sodium alginate, sodium citrate, sodium hyaluronate, chitosan, magnesium stearate, sodium stearyl fumarate, colloidal silicon dioxide, talc, sodium starch glycolate, croscarmellose, crospovidone, tannic acid, or a combination thereof. In some embodiments, the pharmaceutical composition may comprise 50 to 1000 mg of sodium benzoate, 25-300 mg of clozapine, 50-500 mg of sodium alginate, 50-400 mg of sodium citrate, 5-100 mg of magnesium stearate, and 80-200 mg of sodium starch glycolate.

In another aspect, the present disclosure provides a method for treating and/or reducing the risk for a neuropsychiatric disorder, which comprises administering to a subject in need of the treatment an effective amount of any of the pharmaceutical compositions described herein. Target neuropsychiatric disorders include, but are not limited to, schizophrenia, psychotic disorders, Alzheimer's disease, dementia, frontotemporal dementia, mild cognitive impairment, benign forgetfulness, closed head injury, autistic spectrum disorder, Asperger's disorder, attention deficit hyperactivity disorders, obsessive compulsive disorder, tic disorders, childhood learning disorders, premenstrual syndrome, depression, suicidal ideation and/or behaviors, bipolar disorder, anxiety disorders, post-traumatic stress disorder, chronic pain, eating disorders, addiction disorders, personality disorders, Parkinson's disorder, Huntington's disorder, multiple sclerosis, or amyotrophic lateral sclerosis.

In some embodiments, the subject can be a human patient having, suspected of having, or at risk for the neuropsychiatric disorder. The pharmaceutical composition may be administered to the subject by a systemic route, e.g., enteral administration or parenteral administration. In some instances, the subject is administered the pharmaceutical composition at a frequency of four times a day to one time two months. Alternatively or in addition, the subject is treated concurrently with, prior to, or subsequent to one or more additional therapeutic agents for treating and/or reducing the risk for the neuropsychiatric disorder.

Also within the present disclosure are any of the pharmaceutical compositions described herein for use in treating a neuropsychiatric disorder, and uses of such for manufacturing a medicament for treating the target disease.

The details of one or more embodiments of the disclosure are set forth herein. Other features, objects, and advantages of the disclosure will be apparent from the Detailed Description, the Examples, and the Claims.

Definitions

Definitions of specific functional groups and chemical terms are described in more detail below. The chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987. The disclosure is not intended to be limited in any manner by the exemplary listing of substituents described herein.

"Sodium benzoate" refers to a compound of the formula

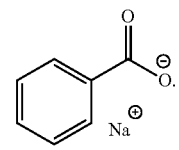

The term "clozapine" refers to the compound with the IAPUC name of 3-chloro-6-(4-methylpiperazin-1-yl)-5H-benzo[b][1,4]benzodiazepine.

The term "commercially available sodium benzoate" refers to sodium benzoate available from commercial source, which may be in amorphous form, may comprise a known single polymorphic form, or may comprise a mixture of amorphous and/or one or more polymorphic forms.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art. For example, Berge et al., describe pharmaceutically acceptable salts in detail in *J. Pharmaceutical Sciences*, 1977, 66, 1-19, incorporated herein by reference.

Pharmaceutically acceptable salts of the compounds described herein include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid, and perchloric acid or with organic acids such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

The term "solvate" refers to forms of the compound that are associated with a solvent, usually by a solvolysis reaction. This physical association may include hydrogen bonding. Conventional solvents include water, methanol, ethanol, acetic acid, dimethyl sulfoxide (DMSO), tetrahydrofuran (THF), diethyl ether, and the like. The compounds described herein may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolatable solvates. Representative solvates include hydrates, ethanolates, and methanolates.

The term "crystalline" or "crystalline form" refers to a solid form substantially exhibiting three-dimensional order. In certain embodiments, a crystalline form of a solid is a solid form that is substantially not amorphous. In certain embodiments, the X-ray powder diffraction (XRPD) pattern of a crystalline form includes one or more sharply defined peaks.

The term "amorphous" or "amorphous form" refers to a form of a solid ("solid form"), the form substantially lacking three-dimensional order. In certain embodiments, an amorphous form of a solid is a solid form that is substantially not crystalline. In certain embodiments, the X-ray powder diffraction (XRPD) pattern of an amorphous form includes a wide scattering band with a peak at $2\theta$ of, e.g., between 20 and 70°, inclusive, using CuK$\alpha$ radiation. In certain embodiments, the XRPD pattern of an amorphous form further includes one or more peaks attributed to crystalline structures. In certain embodiments, the maximum intensity of any one of the one or more peaks attributed to crystalline structures observed at a $2\theta$ of between 20 and 70°, inclusive, is not more than 300-fold, not more than 100-fold, not more than 30-fold, not more than 10-fold, or not more than 3-fold of the maximum intensity of the wide scattering band. In certain embodiments, the XRPD pattern of an amorphous form includes no peaks attributed to crystalline structures.

The term "polymorph" or "polymorphic form" refers to a crystalline form of a compound (or a salt, hydrate, or solvate thereof). All polymorphic forms have the same elemental composition. Different crystalline forms usually have different X-ray diffraction patterns, infrared spectra, melting points, density, hardness, crystal shape, optical and electrical properties, stability, and solubility. Recrystallization solvent, rate of crystallization, storage temperature, and other factors may cause one crystal form to dominate. Various polymorphic forms of a compound can be prepared by crystallization under different conditions.

The terms "inhibition", "inhibiting", "inhibit," or "inhibitor" refer to the ability of a polymorphic form to reduce, slow, halt or prevent activity of a particular biological process in a cell relative to vehicle.

When a polymorphic form, pharmaceutical composition, method, use, or kit is referred to as "selectively," "specifically," or "competitively" binding a first protein, the polymorphic form binds the first protein with a higher binding affinity (e.g., not less than about 2-fold, not less than about 5-fold, not less than about 10-fold, not less than about 30-fold, not less than about 100-fold, not less than about 1,000-fold, or not less than about 10,000-fold) than binding a second protein or that is different from the first protein. When a polymorphic form is referred to as "selectively," "specifically," or "competitively" modulating (e.g., increasing or inhibiting) the activity of a first protein, the polymorphic form modulates the activity of the first protein to a greater extent (e.g., not less than about 2-fold, not less than about 5-fold, not less than about 10-fold, not less than about 30-fold, not less than about 100-fold, not less than about 1,000-fold, or not less than about 10,000-fold) than the activity of at least one protein that is different from the first protein.

The term "aberrant activity" refers to activity deviating from normal activity. The term "increased activity" refers to activity higher than normal activity.

The terms "composition" and "formulation" are used interchangeably.

The terms "solvent" and "anti-solvent" refer to either conventional or non-conventional solvents including but not limited to water, acetone, acetonitrile, butanol, dioxane, ethanol, ethyl acetate, isobutanol, isopropanol, methanol, methyl ethyl ketone, methyl-1-butanol, methyl t-butyl ether, tetrahydrofuran, and toluene. The term "solvent" refers to a substance (e.g., a liquid) added to dissolve a solute (another substance (e.g., a solid)), to form a solution. The term "anti-solvent" refers to a solvent in which a solute is less soluble.

A "subject" to which administration is contemplated refers to a human (i.e., male or female of any age group, e.g., pediatric subject (e.g., infant, child, or adolescent) or adult subject (e.g., young adult, middle-aged adult, or senior adult)) or non-human animal. A "patient" refers to a human subject in need of treatment of a disease. For example, the subject can be a human patient having, suspected of having, or at risk for a target disease as described herein.

The terms "administer," "administering," or "administration" refers to implanting, absorbing, ingesting, injecting, inhaling, or otherwise introducing a polymorphic form of sodium benzoate described herein, or a composition thereof, in or on a subject.

The terms "treatment," "treat," and "treating" refer to reversing, alleviating, delaying the onset of, or inhibiting the progress of a disease described herein. In some embodiments, treatment may be administered after one or more signs or symptoms of the disease have developed or have been observed. In other embodiments, treatment may be administered in the absence of signs or symptoms of the disease. For example, treatment may be administered to a susceptible subject prior to the onset of symptoms (e.g., in light of a history of symptoms and/or in light of exposure to a pathogen) to delay or prevent disease occurrence. Treatment may also be continued after symptoms have resolved, for example, to delay or prevent recurrence.

The terms "condition," "disease," and "disorder" are used interchangeably.

An "effective amount" of any of the active ingredients described herein (e.g. any of the sodium benzoate compounds and/or clozapine) refers to an amount sufficient to elicit the desired biological response, i.e., treating the condition. As will be appreciated by those of ordinary skill in this art, the effective amount of any of the active ingredients described herein may vary depending on such factors as the desired biological endpoint, the pharmacokinetics of the polymorphic form, the condition being treated, the mode of administration, and the age and health of the subject. In certain embodiments, an effective amount is a therapeutically effective amount. In certain embodiments, an effective amount is a prophylactically effective amount. In certain embodiments, an effective amount is the amount of any of the active ingredients described herein in a single dose. In certain embodiments, an effective amount is the combined amounts of the active ingredients described herein in multiple doses.

A "therapeutically effective amount" of any of the active ingredients described herein is an amount sufficient to provide a therapeutic benefit in the treatment of a condition or to delay or minimize one or more symptoms associated with the condition. A therapeutically effective amount of any of the active ingredients means an amount of therapeutic agent, alone or in combination with other therapies, which provides a therapeutic benefit in the treatment of the condition. The term "therapeutically effective amount" can encompass an amount that improves overall therapy, reduces or avoids symptoms, signs, or causes of the condition, and/or enhances the therapeutic efficacy of another therapeutic agent.

A "prophylactically effective amount" of any of the active ingredients described herein is an amount sufficient to prevent a condition, or one or more symptoms associated with the condition or prevent its recurrence. A prophylactically effective amount of any of the active ingredients means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent.

The terms "about" or "approximately," which are used interchangeably herein, means within an acceptable error range for the particular value as determined by one of ordinary skill in the art, which will depend in part on how the value is measured or determined, i.e., the limitations of the measurement system. For example, "about" or "approximately" can mean a range of less than ±10%, preferably less than ±5%, more preferably less than ±1%, more preferably less than ±0.5% of a given value. Where particular values are described in the application and claims, unless otherwise stated, the term "about" is implicit and in this context means within an acceptable error range for the particular value.

The term "neurological disease" refers to any disease of the nervous system, including diseases that involve the central nervous system (brain, brainstem, spinal cord, and cerebellum), the peripheral nervous system (including cranial nerves), and the autonomic nervous system (parts of which are located in both central and peripheral nervous system). Neurodegenerative diseases refer to a type of neurological disease marked by the loss of nerve cells, including, but not limited to, Alzheimer's disease, Parkinson's disease, frontotemporal dementia, multiple sclerosis, amyotrophic lateral sclerosis, tauopathies (including frontotemporal dementia), multiple system atrophy, and Huntington's disease. Examples of neurological diseases include, but are not limited to, headache, stupor and coma, dementia, seizure, sleep disorders, trauma, infections, neoplasms, neuro-ophthalmopathy, movement disorders, demyelinating diseases, spinal cord disorders, and disorders of peripheral nerves, muscle and neuromuscular junctions. Addiction and mental illness, include, but are not limited to, bipolar disorder, depression and schizophrenia, are also included in the definition of CNS diseases. Further examples of neurological diseases include acquired epileptiform aphasia; acute disseminated encephalomyelitis; adrenoleukodystrophy; agenesis of the corpus callosum; agnosia; Aicardi syndrome; Alexander disease; Alpers' disease; alternating hemiplegia; Alzheimer's disease; amyotrophic lateral sclerosis; anencephaly; Angelman syndrome; angiomatosis; anoxia; aphasia; apraxia; arachnoid cysts; arachnoiditis; Arnold-Chiari malformation; arteriovenous malformation; Asperger syndrome; ataxia telangiectasia; attention deficit hyperactivity disorder; autism; autonomic dysfunction; back pain; Batten disease; Behcet's disease; Bell's palsy; benign essential blepharospasm; benign focal amyotrophy; benign intracranial hypertension; Binswanger's disease; blepharospasm; Bloch Sulzberger syndrome; brachial plexus injury; brain abscess; brain injury; brain tumors (including glioblastoma multiforme); spinal cord tumor; Brown-Sequard syndrome; Canavan disease; carpal tunnel syndrome (CTS); causalgia; central pain syndrome; central pontine myelinolysis; cephalic disorder; cerebral aneurysm; cerebral arteriosclerosis; cerebral atrophy; cerebral gigantism; cerebral palsy; Charcot-Marie-Tooth disease; chemotherapy-induced neuropathy and neuropathic pain; Chiari malformation; chorea; chronic inflammatory demyelinating polyneuropathy (CIDP); chronic pain; chronic regional pain syndrome; Coffin Lowry syndrome; coma, including persistent vegetative state; congenital facial diplegia; corticobasal degeneration; cranial arteritis; craniosynostosis; Creutzfeldt-Jakob disease; cumulative trauma disorders; Cushing's syndrome; cytomegalic inclusion body disease (CIBD); cytomegalovirus infection; dancing eyes-dancing feet syndrome; Dandy-Walker syndrome; Dawson disease; De Morsier's syndrome; Dejerine-Klumpke palsy; dementia; dermatomyositis; diabetic neuropathy; diffuse sclerosis; dysautonomia; dysgraphia; dyslexia; dystonias; early infantile epileptic encephalopathy; empty sella syndrome; encephalitis; encephaloceles; encephalotrigeminal angiomatosis; epilepsy; Erb's palsy; essential tremor; Fabry's disease; Fahr's syndrome; fainting; familial spastic paralysis; febrile seizures; Fisher syndrome; Friedreich's ataxia; frontotemporal dementia and other "tauopathies"; Gaucher's disease; Gerstmann's syndrome; giant cell arteritis; giant cell inclusion disease; globoid cell leukodystrophy; Guillain-Barre syndrome; HTLV-1 associated myelopathy; Hallervorden-Spatz disease; head injury; headache; hemifacial spasm; hereditary spastic paraplegia; heredopathia atactica polyneuritiformis; herpes zoster oticus; herpes zoster; Hirayama syndrome; HIV-associated dementia and neuropathy (see also neurological manifestations of AIDS); holoprosencephaly; Huntington's disease and other polyglutamine repeat diseases; hydranencephaly; hydrocephalus; hypercortisolism; hypoxia; immune-mediated encephalomyelitis; inclusion body myositis; incontinentia pigmenti; infantile phytanic acid storage disease; Infantile Refsum disease; infantile spasms; inflammatory myopathy; intracranial cyst; intracranial hypertension; Joubert syndrome; Kearns-Sayre syndrome; Kennedy disease; Kinsbourne syndrome; Klippel Feil syndrome; Krabbe disease; Kugelberg-Welander disease; kuru; Lafora disease; Lambert-Eaton myasthenic syndrome; Landau-Kleffner syndrome; lateral medullary (Wallenberg) syndrome; learning disabilities; Leigh's disease; Lennox-Gastaut syndrome; Lesch-Nyhan syndrome; leukodystrophy; Lewy body dementia; lissencephaly; locked-in syndrome; Lou Gehrig's disease (aka motor neuron disease or amyotrophic lateral sclerosis); lumbar disc disease; lyme disease-neurological sequelae; Machado-Joseph disease; macrencephaly; megalencephaly; Melkersson-Rosenthal syndrome; Menieres disease; meningitis; Menkes disease; metachromatic leukodystrophy; microcephaly; migraine; Miller Fisher syndrome; mini-strokes; mitochondrial myopathies; Mobius syndrome; monomelic amyotrophy; motor neurone disease; moyamoya disease; mucopolysaccharidoses; multi-infarct dementia; multifocal motor neuropathy; multiple sclerosis and other demyelinating disorders; multiple system atrophy with postural hypotension; muscular dystrophy; myasthenia gravis; myelinoclastic diffuse sclerosis; myoclonic encephalopathy of infants; myoclonus; myopathy; myotonia congenital; narcolepsy; neurofibromatosis; neuroleptic malignant syndrome; neurological manifestations of AIDS; neurological sequelae of lupus; neuromyotonia; neuronal ceroid lipofuscinosis; neuronal migration disorders; Niemann-Pick disease; O'Sullivan-McLeod syndrome; occipital neuralgia; occult spinal dysraphism sequence; Ohtahara syndrome; olivopontocerebellar atrophy; opsoclonus myoclonus; optic neuritis; orthostatic hypotension; overuse syndrome; paresthesia; Parkinson's disease; paramyotonia congenita; paraneoplastic diseases; paroxysmal attacks; Parry Romberg syndrome; Pelizaeus-Merzbacher disease; periodic paralyses; peripheral neuropathy; painful neuropathy and neuropathic pain; persistent vegetative state; pervasive developmental disorders; photic sneeze reflex; phytanic acid storage disease; Pick's disease; pinched nerve; pituitary tumors; polymyositis; porencephaly; Post-Polio syndrome; postherpetic neuralgia (PHN); postinfectious encephalomyelitis; postural hypotension; Prader-Willi syndrome; primary lateral sclerosis; prion diseases; progressive; hemifacial atrophy; progressive multifocal leukoencephalopathy; progressive sclerosing poliodystrophy; progressive supranuclear palsy; pseudotumor cerebri; Ramsay-Hunt syndrome (Type I and Type II); Rasmussen's Encephalitis; reflex sympathetic dystrophy syndrome; Refsum disease; repetitive motion disorders; repetitive stress injuries; restless legs syndrome; retrovirus-associated myelopathy; Rett syndrome; Reye's syndrome; Saint Vitus Dance; Sandhoff disease; Schilder's disease; schizencephaly; septo-optic dysplasia; shaken baby syndrome; shingles; Shy-Drager syndrome; Sjogren's syndrome; sleep apnea; Soto's syndrome; spasticity; spina bifida; spinal cord injury; spinal cord tumors; spinal muscular atrophy; stiff-person syndrome; stroke; Sturge-Weber syndrome; subacute sclerosing panencephalitis; subarachnoid hemorrhage; subcortical arteriosclerotic encephalopathy; sydenham chorea; syncope; syringomyelia; tardive dyskinesia; Tay-Sachs disease; temporal arteritis; tethered spinal cord syndrome; Thomsen disease; thoracic outlet syndrome; tic douloureux; Todd's paralysis; Tourette syndrome; transient ischemic attack; transmissible spongiform encephalopathies; transverse myelitis; traumatic brain injury; tremor; trigeminal neuralgia; tropical spastic paraparesis; tuberous sclerosis; vascular dementia (multi-infarct dementia); vasculitis including temporal arteritis; Von Hippel-Lindau Disease (VHL); Wallenberg's syndrome; Werdnig-Hoffman disease; West syndrome; whiplash; Williams syndrome; Wilson's disease; and Zellweger syndrome.

The term "psychiatric disorder" refers to mental disorders and includes diseases and disorders listed in the Diagnostic and Statistical Manual of Mental Disorders—Fourth Edition and Fifth Edition (DSM-IV, DSM-V), published by the American Psychiatric Association, Washington D.C. (1994, 2013). Psychiatric disorders include, but are not limited to, anxiety disorders (e.g., acute stress disorder, agoraphobia, generalized anxiety disorder, obsessive-compulsive disorder, panic disorder, posttraumatic stress disorder, separation anxiety disorder, social phobia, and specific phobia), childhood disorders, (e.g., attention-deficit/hyperactivity disorder, conduct disorder, and oppositional defiant disorder), eating disorders (e.g., anorexia nervosa and bulimia nervosa), mood disorders (e.g., depression, bipolar disorder I and II, cyclothymic disorder, dysthymic disorder, and major depressive disorder), personality disorders (e.g., antisocial personality disorder, avoidant personality disorder, borderline personality disorder, dependent personality disorder, histrionic personality disorder, narcissistic personality disorder, obsessive-compulsive personality disorder, paranoid personality disorder, schizoid personality disorder, and schizotypal personality disorder), psychotic disorders (e.g., brief psychotic disorder, delusional disorder, schizoaffective disorder, schizophreniform disorder, schizophrenia, and shared psychotic disorder), substance-related disorders (e.g., alcohol dependence or abuse, amphetamine dependence or abuse, *Cannabis* dependence or abuse, cocaine dependence or abuse, hallucinogen dependence or abuse, inhalant dependence or abuse, nicotine dependence or abuse, opioid dependence or abuse, phencyclidine dependence or abuse, and sedative dependence or abuse), adjustment disorders, autism, Asperger's disorder, delirium, dementia, multi-infarct dementia, learning and memory disorders (e.g., amnesia and age-related memory loss), tic disorder and Tourette's disorder.

As used herein, the term "personality disorders" refers to mental disorders characterized by enduring maladaptive patterns of behavior, cognition, and inner experience, exhibited across many contexts and deviating markedly from those accepted by the individual's culture. These patterns develop early, are inflexible, and are associated with significant distress or disability. For example, the personality disorders can include, but not limited to, paranoid, schizoid, schizotypal, antisocial, borderline, histrionic, narcissistic, avoidant, dependent, and obsessive-compulsive personality disorder.

The term "neuropsychiatric disorder," including either neurological diseases or psychiatric disorders or central nervous system disorders (CNS disorders), refers to a disorder that involves either psychiatric symptoms or syndromes caused by organic central nervous system disorders. The main characteristics of neuropsychiatric symptoms include occurrence of the various psychiatric symptoms, cognitive impairment, neurological symptoms or the possibility of early cerebral development symptoms.

The terms "health food" or "health food product" refers to any kind of liquid and solid/semi-solid materials that are used for nourishing humans and animals, for improving basic behavioral functioning, hyperactivity, mood, anxiety, depression, sensory perception, sensorimotor gating, pain threshold, memory and/or cognitive functioning, body weight, or for facilitating treatment of any of the target diseases noted herein. The term "nutraceutical composition" refers to compositions containing components from food sources and conferring extra health benefits in addition to the basic nutritional value found in foods.

The term "medical food product" refers to a food product formulated to be consumed or administered enterally, including a food product that is usually used under the supervision of a physician for the specific dietary management of a target disease, such as those described herein. A "medical food product" composition may refer to a composition that is specially formulated and processed (as opposed to a naturally occurring foodstuff used in a natural state) for a patient in need of the treatment (e.g., human patients who suffer from illness or who requires use of the product as a major active agent for alleviating a disease or condition via specific dietary management).

DETAILED DESCRIPTION

The present disclosure provides novel polymorphic forms of sodium benzoate. The polymorphic forms are more stable than the amorphous and the known polymorphic forms and are useful in treating and/or reducing the risk for various diseases and disorders, including neuropsychiatric disorders, in a subject. Thus, also provided herein are methods of preparing the polymorphic forms, compositions, kits, and methods of using the polymorphic forms of sodium benzoate described herein for treating and/or reducing the risk for any of the target diseases described herein.

Further, the present disclosure provides a pharmaceutical composition comprises an effective amount of a sodium benzoate compound and an effective amount of clozapine. The crystalline sodium benzoate of the invention (i.e. the polymorphic form of sodium benzoate) is more stable than the amorphous and the other known polymorphic forms of sodium benzoate or their combinations. Additionally, the excipients comprised in the pharmaceutical composition described herein improve the stability of the combination of the sodium benzoate compound and clozapine. The pharmaceutical composition described herein is useful in preventing, treating and/or reducing the risk for various diseases and disorders, including neuropsychiatric disorders, in a subject. Thus, also provided herein is a method for preventing, treating and/or reducing the risk for any of the target diseases described herein by administering the pharmaceutical composition described herein.

Novel Polymorphic Forms of Sodium Benzoate

One aspect of the present disclosure relates to the polymorphic forms of sodium benzoate as described herein. These polymorphic forms are useful in treating and/or reducing the risk for neuropsychiatric disorders in a subject.

Figure 1:
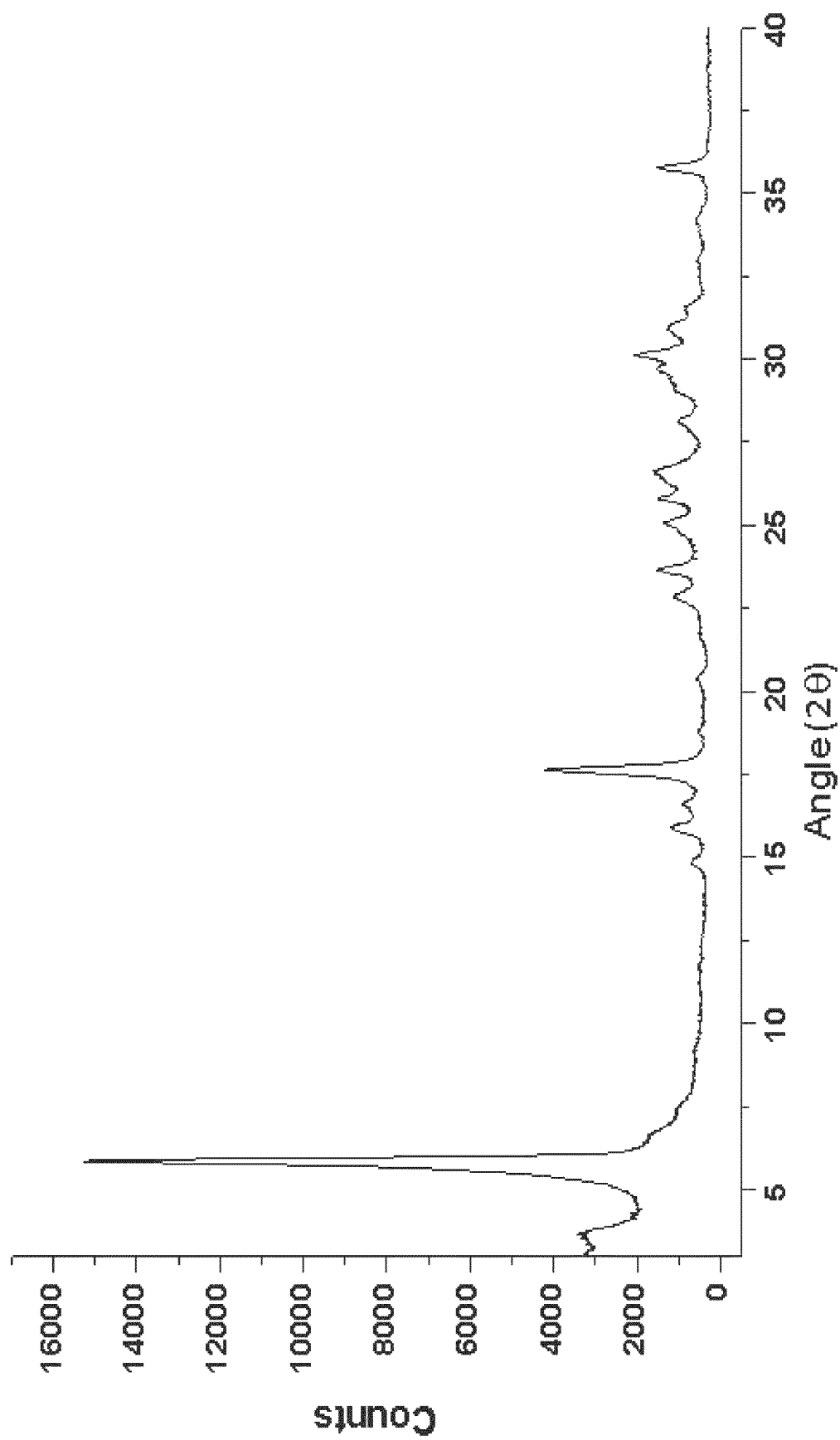
FIG. 1 shows the X-ray powder diffraction (XRPD) of polymorphic form #1 of sodium benzoate from Example 1, with peaks (°) of: 3.6, 5.9, 7.2, 7.5, 14.9, 15.9, 16.6, 17.6, 18.8, 20.4, 22.9, 23.7, 25.1, 25.8, 26.6, 28.1, 29.1, 29.4, 29.7, 30.2, 31.2, 31.5, 32.9, 34.2, and 35.7.
Figure 2:
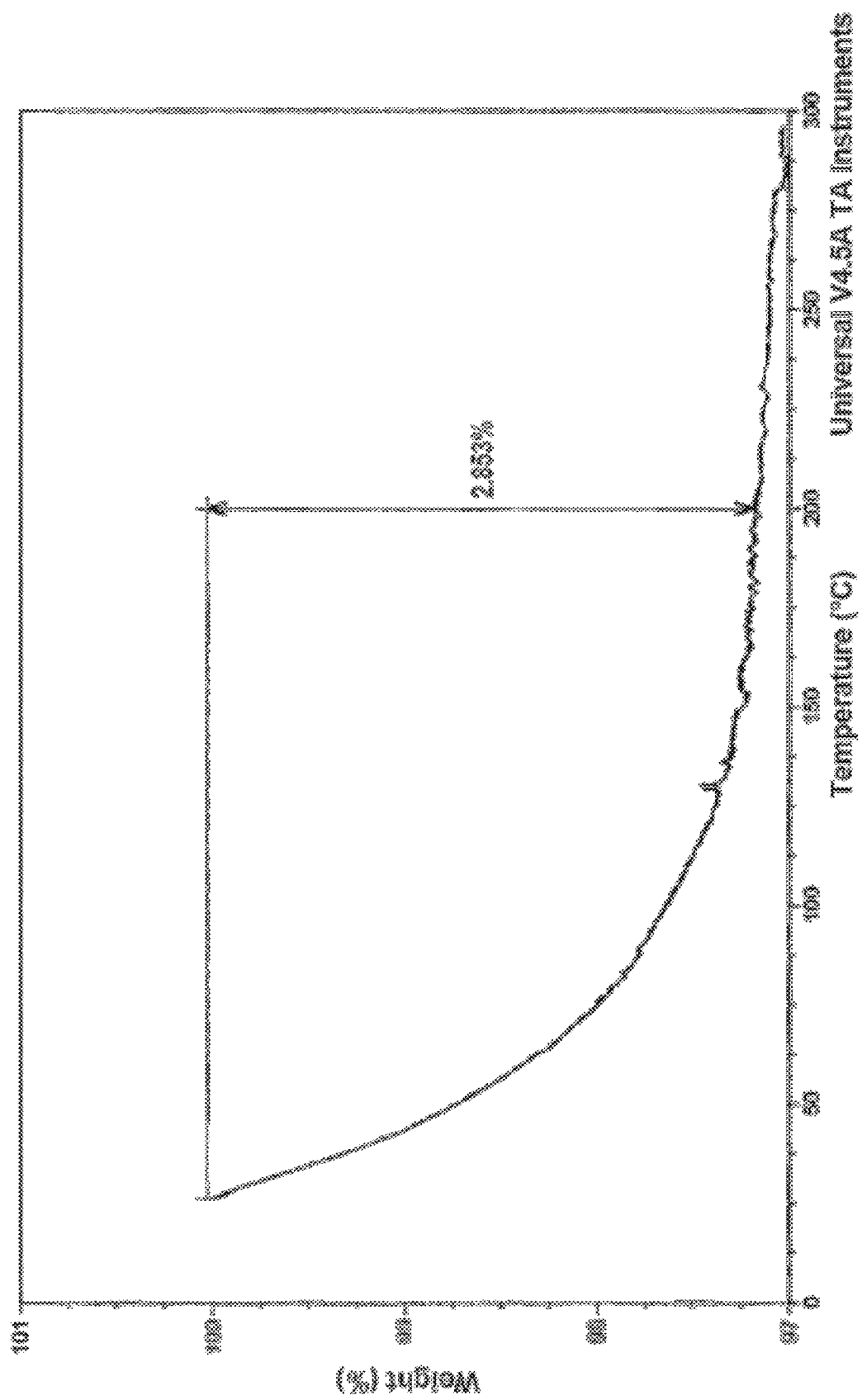
FIG. 2 shows the Thermogravimetric Analysis (TGA) of polymorphic form #1 of sodium benzoate from Example 1.
Figure 3:
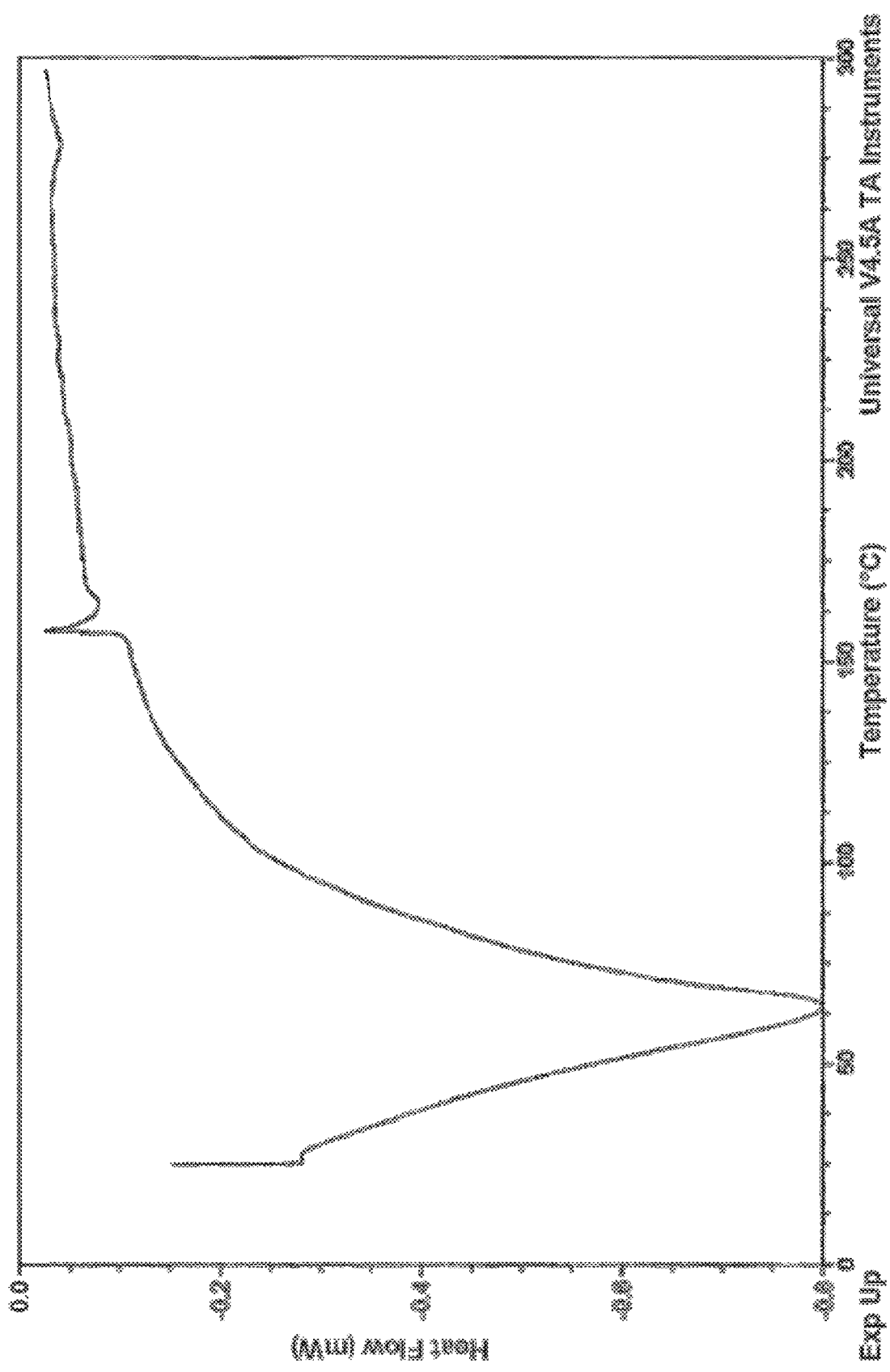
FIG. 3 shows the profile determined by the differential scanning calorimeter method (DSC), of polymorphic form #1 of sodium benzoate from Example 1.

In one aspect, the polymorphic form of sodium benzoate has a X-ray powder diffraction pattern comprising characteristic peaks at a reflection angle 2θ of approximately 5.9, 30.2, and 31.2 degrees. In some embodiments, the X-ray diffraction pattern can be determined by a period of a scan speed of about 0.1 to 0.3 seconds per step. In some embodiments, the polymorphic form of sodium benzoate has a X-ray powder diffraction pattern at a reflection angle 2θ further comprising characteristic peaks at approximately 3.6, 7.2, 7.5, 14.9, 15.9, 16.6, 17.6, 18.8, 20.4, 22.9, 23.7, 25.1, 25.8, 26.6, 28.1, 29.1, 29.4, 29.7, 31.5, 32.9, 34.2, and 35.7 degrees. In some embodiments, the X-ray diffraction pattern can be determined by a period of a scan speed of about 0.1 to 0.3 seconds per step. In some embodiments, the polymorphic form has a X-ray powder diffraction pattern substantially as depicted in FIG. 1. In some embodiments, the X-ray diffraction pattern can be determined by a period of a scan speed of about 0.1 to 0.3 seconds per step. In some embodiments, the polymorphic form has a TGA pattern substantially as depicted in FIG. 2. In some embodiments, the polymorphic form has a DSC pattern substantially as depicted in FIG. 3. In some embodiments, the polymorphic form has an X-ray powder diffraction pattern substantially as depicted in FIG. 1, a TGA pattern substantially as depicted in FIG. 2, and a DSC pattern substantially as depicted in FIG. 3.

In one aspect, the polymorphic form of sodium benzoate has a X-ray powder diffraction pattern comprising characteristic peaks at a reflection angle 2θ of approximately 3.6, 7.5, 26.6, and 29.4 degrees; wherein the X-ray diffraction pattern is determined by a period of a scan speed of about 1.0 second per step. In one aspect, the polymorphic form of sodium benzoate has a X-ray powder diffraction pattern further comprising characteristic peaks at a reflection angle 2θ of approximately 5.9, 6.8, 17.6, 27.6, 30.2, 30.9, and 32.3 degrees; wherein the X-ray diffraction pattern is determined by a period of a scan speed of about 1.0 second per step. In one aspect, the polymorphic form of sodium benzoate has a X-ray powder diffraction pattern further comprising characteristic peaks at a reflection angle 2θ of approximately 11.1, 14.9, 26.2, 32.9, and 35.7 degrees; wherein the X-ray diffraction pattern is determined by a period of a scan speed of about 1.0 second per step. In one aspect, the polymorphic form of sodium benzoate has a X-ray powder diffraction pattern further comprising characteristic peaks at a reflection angle 2θ of approximately 12.4 and 22.9 degrees; wherein the X-ray diffraction pattern is determined by a period of a scan speed of about 1.0 second per step.

Figure 25:
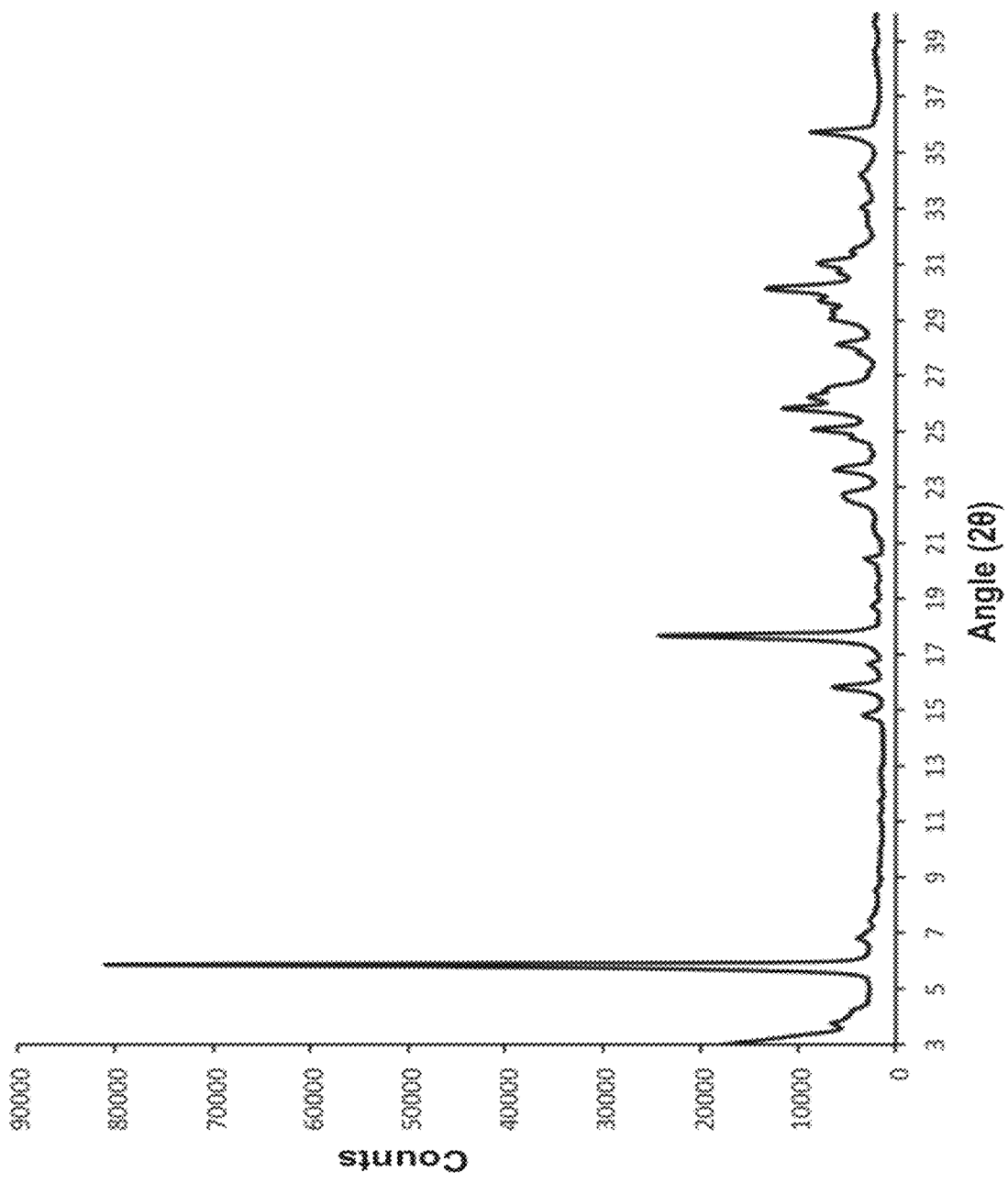
FIG. 25 shows the X-ray powder diffraction (XRPD) of polymorphic form #1 of sodium benzoate from Example 1, with peaks (°) of: 3.6, 4.2, 5.9, 6.8, 7.5, 8.5, 9.2, 11.1, 11.7, 12.4, 14.9, 15.9, 16.6, 17.6, 18.8, 19.4, 20.4, 21.6, 22.9, 23.7, 24.7, 25.1, 25.8, 26.1, 26.6, 27.7, 28.1, 29.1, 29.4, 29.7, 30.2, 30.6, 30.9, 31.5, 32.4, 32.9, 33.6, 34.2, 35.7, 38.6, and 39.6; wherein the X-ray diffraction pattern is determined by a period of a scan speed of about 1.0 second per step.

In one aspect, the polymorphic form of sodium benzoate has a X-ray powder diffraction pattern comprising characteristic peaks at a reflection angle 2θ of approximately 3.6, 7.5, 26.6, and 29.4 degrees; wherein the X-ray diffraction pattern is determined by a period of a scan speed of about 1.0 second per step. In some embodiments, the polymorphic form of sodium benzoate has a X-ray powder diffraction pattern at a reflection angle 2θ further comprising characteristic peaks at approximately 4.2, 8.5, 9.2, 11.1, 11.7, 12.4, 14.9, 15.9, 16.6, 18.8, 19.4, 20.4, 21.6, 22.9, 23.7, 24.7, 25.1, 25.8, 26.1, 28.1, 29.1, 29.7, 30.6, 31.5, 32.9, 33.6, 34.2, 35.7, 38.6, and 39.6 degrees; wherein the X-ray diffraction pattern is determined by a period of a scan speed of about 1.0 second per step. In some embodiments, the polymorphic form has a X-ray powder diffraction pattern substantially as depicted in FIG. 25; wherein the X-ray diffraction pattern is determined by a period of a scan speed of about 1.0 seconds per step. In some embodiments, the polymorphic form has a TGA pattern substantially as depicted in FIG. 2. In some embodiments, the polymorphic form has a DSC pattern substantially as depicted in FIG. 3. In some embodiments, the polymorphic form has an X-ray powder diffraction pattern substantially as depicted in FIG. 25, a TGA pattern substantially as depicted in FIG. 2, and a DSC pattern substantially as depicted in FIG. 3.

Figure 4:
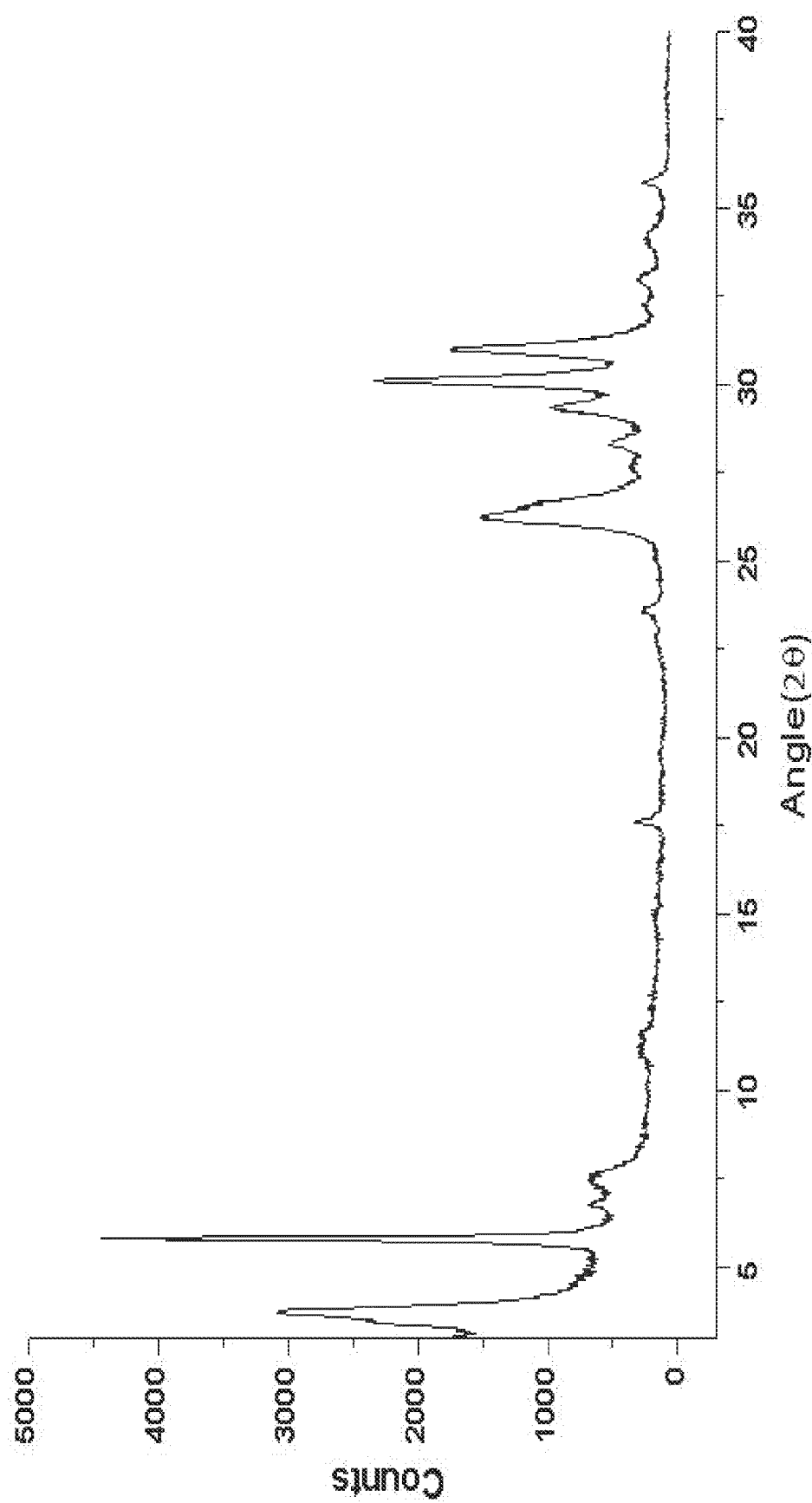
FIG. 4 shows the X-ray powder diffraction (XRPD) of polymorphic form #2 of sodium benzoate from Example 2, with peaks (°) of: 3.7, 5.9, 6.8, 7.5, 11.3, 11.6, 17.6, 22.7, 23.5, 26.2, 27.6, 28.3, 29.3; 30.2, 31.2, 32.2, 32.9, 34.0, and 35.7.
Figure 5:
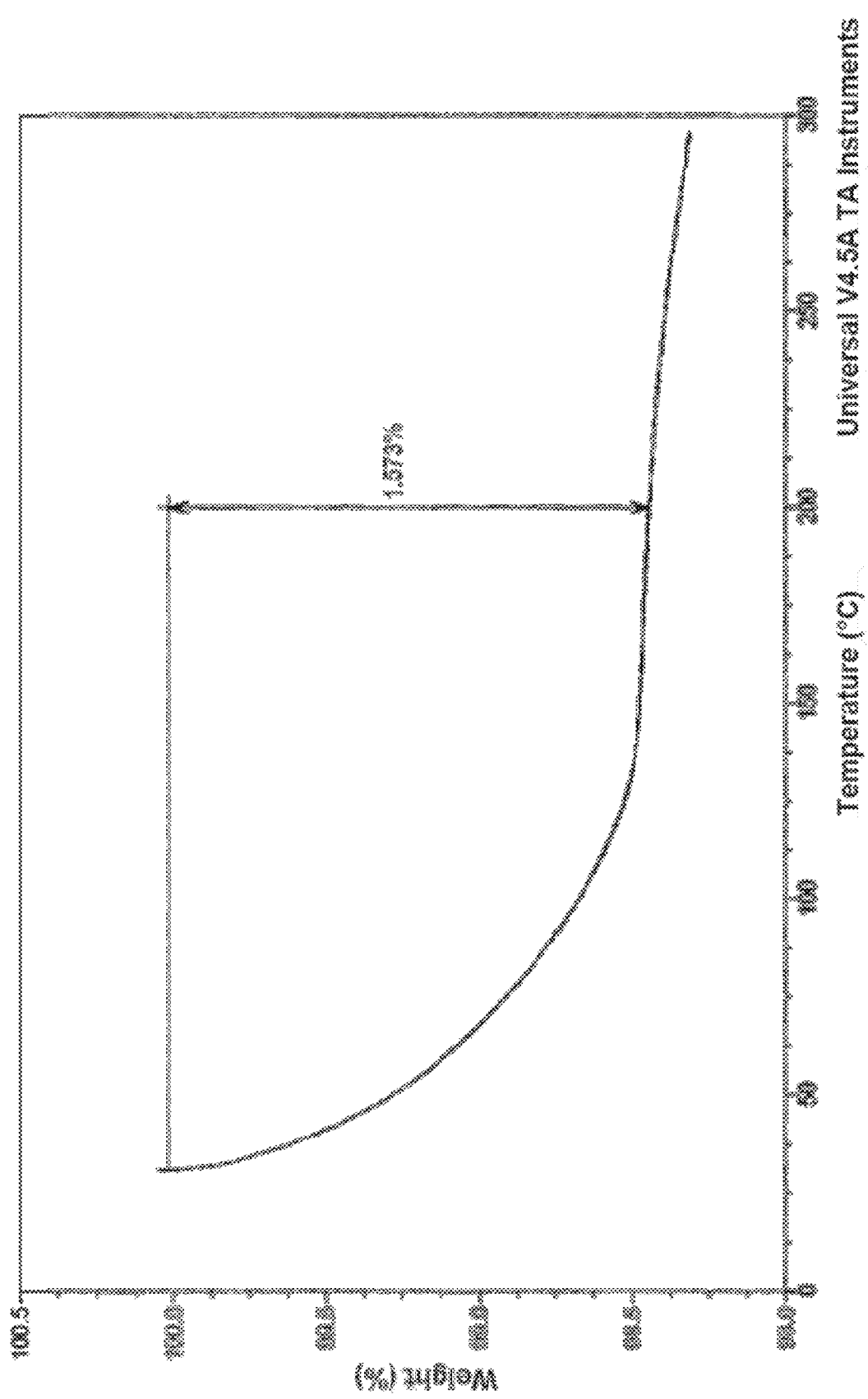
FIG. 5 shows the Thermogravimetric Analysis (TGA) of polymorphic form #2 of sodium benzoate from Example 2.
Figure 6:
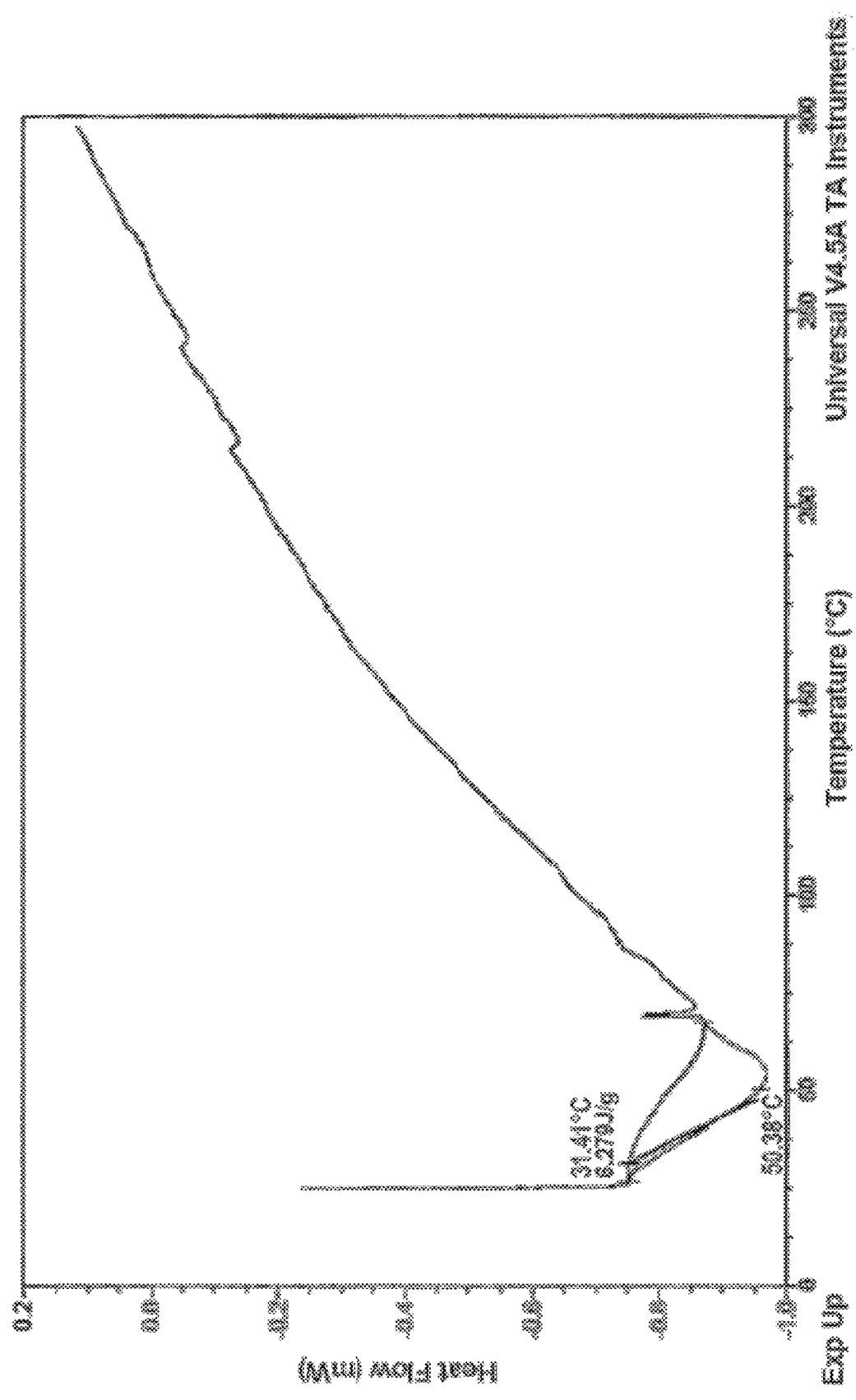
FIG. 6 shows the profile determined by the differential scanning calorimeter method (DSC), of polymorphic form #2 of sodium benzoate from Example 2.

In some embodiments, the polymorphic form of sodium benzoate has a X-ray powder diffraction pattern at a reflection angle 2θ further comprising characteristic peaks at approximately 3.7, 6.8, 7.5, 11.3, 11.6, 17.6, 22.7, 23.5, 26.2, 27.6, 28.3, 29.3, 32.2, 32.9, 34.0, and 35.7 degrees. In some embodiments, the X-ray diffraction pattern can be determined by a period of a scan speed of about 0.1 to 0.3 seconds per step. In some embodiments, the polymorphic form has an X-ray powder diffraction pattern substantially as depicted in FIG. 4. In some embodiments, the X-ray diffraction pattern can be determined by a period of a scan speed of about 0.1 to 0.3 seconds per step. In some embodiments, the polymorphic form has a TGA pattern substantially as depicted in FIG. 5. In some embodiments, the polymorphic form has a DSC pattern substantially as depicted in FIG. 6. In some embodiments, the polymorphic form has an X-ray powder diffraction pattern substantially as depicted in FIG. 4, a TGA pattern substantially as depicted in FIG. 5, and a DSC pattern substantially as depicted in FIG. 6.

Figure 26:
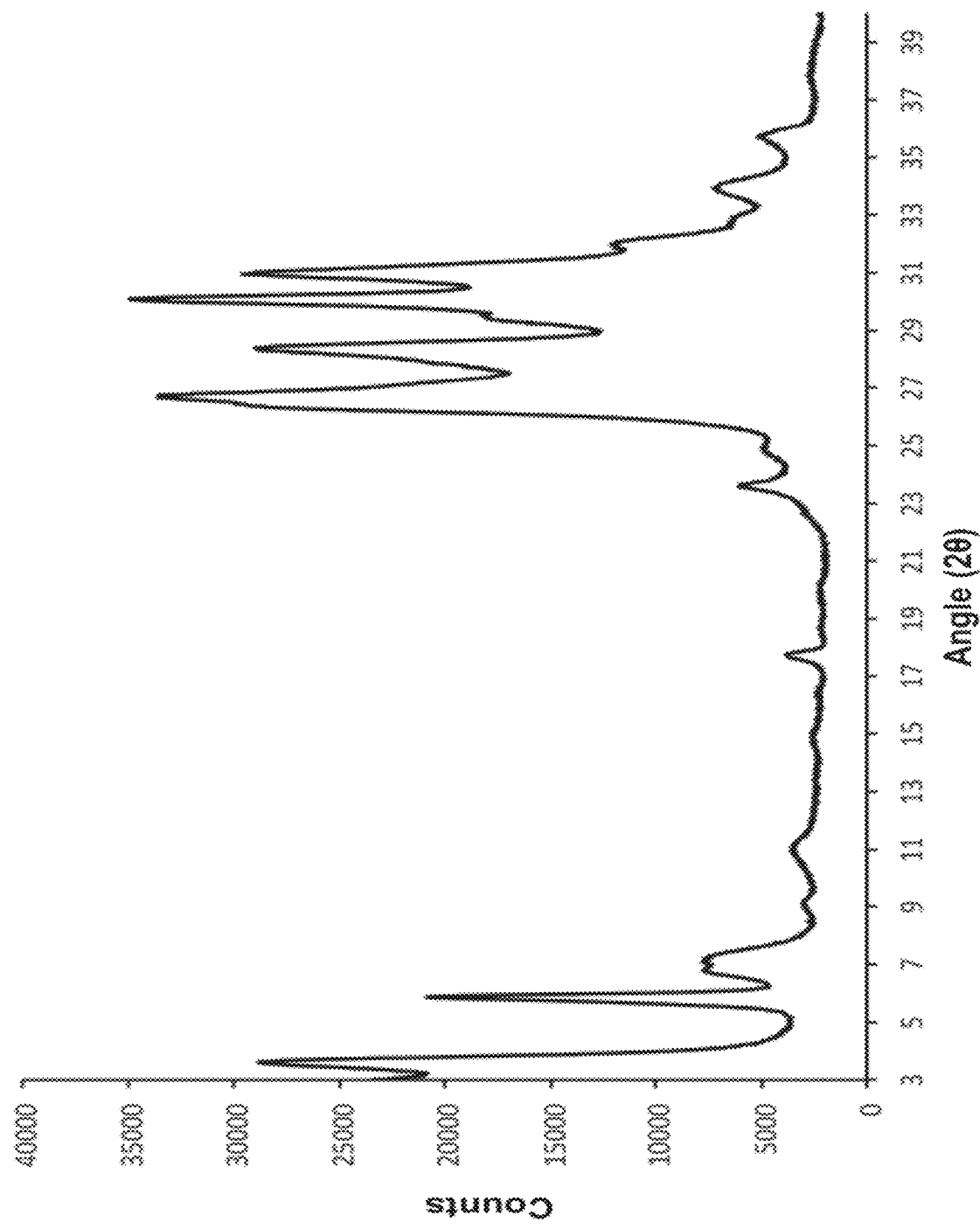
FIG. 26 shows the X-ray powder diffraction (XRPD) of polymorphic form #2 of sodium benzoate from Example 2, with peaks (°) of: 3.7, 5.9, 6.8, 7.5, 8.9, 11.1, 14.9, 17.6, 22.7, 23.5, 24.8, 26.2, 26.6, 27.6, 28.3, 29.3, 30.2, 30.9, 32.2, 32.9, 34.0, 35.7, and 37.8; wherein the X-ray diffraction pattern is determined by a period of a scan speed of about 1.0 second per step.

In some embodiments, the polymorphic form of sodium benzoate has a X-ray powder diffraction pattern at a reflection angle 2θ further comprising characteristic peaks at approximately 8.9, 11.1, 14.9, 22.7, 23.5, 24.8, 26.2, 28.3, 32.9, 34.0, 35.7, and 37.8 degrees; wherein the X-ray diffraction pattern is determined by a period of a scan speed of about 1.0 second per step. In some embodiments, the polymorphic form has an X-ray powder diffraction pattern substantially as depicted in FIG. 26; wherein the X-ray diffraction pattern is determined by a period of a scan speed of about 1.0 second per step. In some embodiments, the polymorphic form has a TGA pattern substantially as depicted in FIG. 5. In some embodiments, the polymorphic form has a DSC pattern substantially as depicted in FIG. 6. In some embodiments, the polymorphic form has an X-ray powder diffraction pattern substantially as depicted in FIG. 26, a TGA pattern substantially as depicted in FIG. 5, and a DSC pattern substantially as depicted in FIG. 6.

Figure 7:
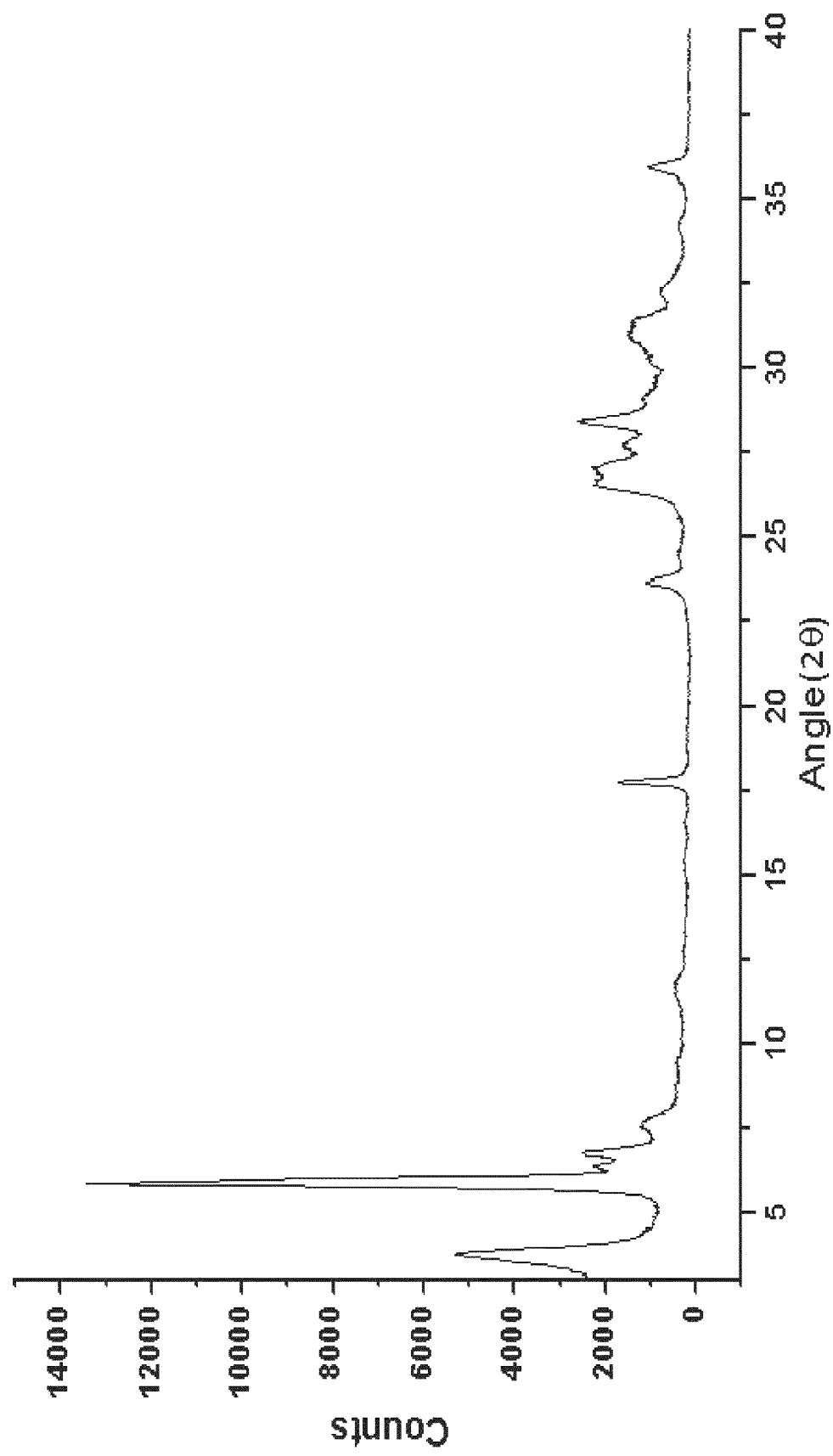
FIG. 7 shows the X-ray powder diffraction (XRPD) of polymorphic form #3 of sodium benzoate from Example 3, with peaks (°) of: 3.7, 5.9, 6.3, 6.8, 7.5, 11.7, 17.7, 23.6, 24.5, 26.5, 27.0, 27.7, 28.4, 29.0, 30.2; 31.0, 31.2, 32.3, 34.2, and 35.9.
Figure 8:
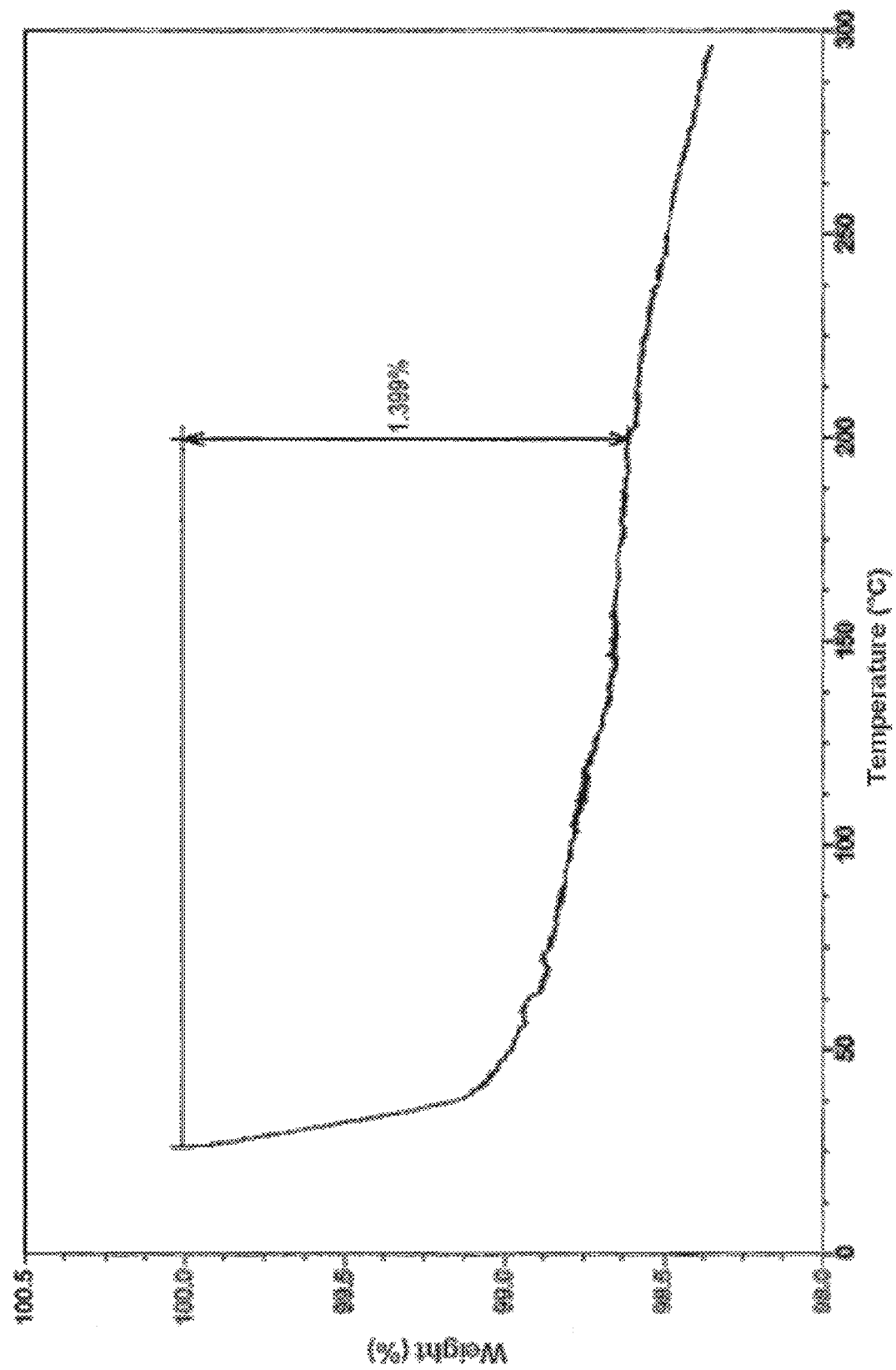
FIG. 8 shows the Thermogravimetric Analysis (TGA) of polymorphic form #3 of sodium benzoate from Example 3.
Figure 9:
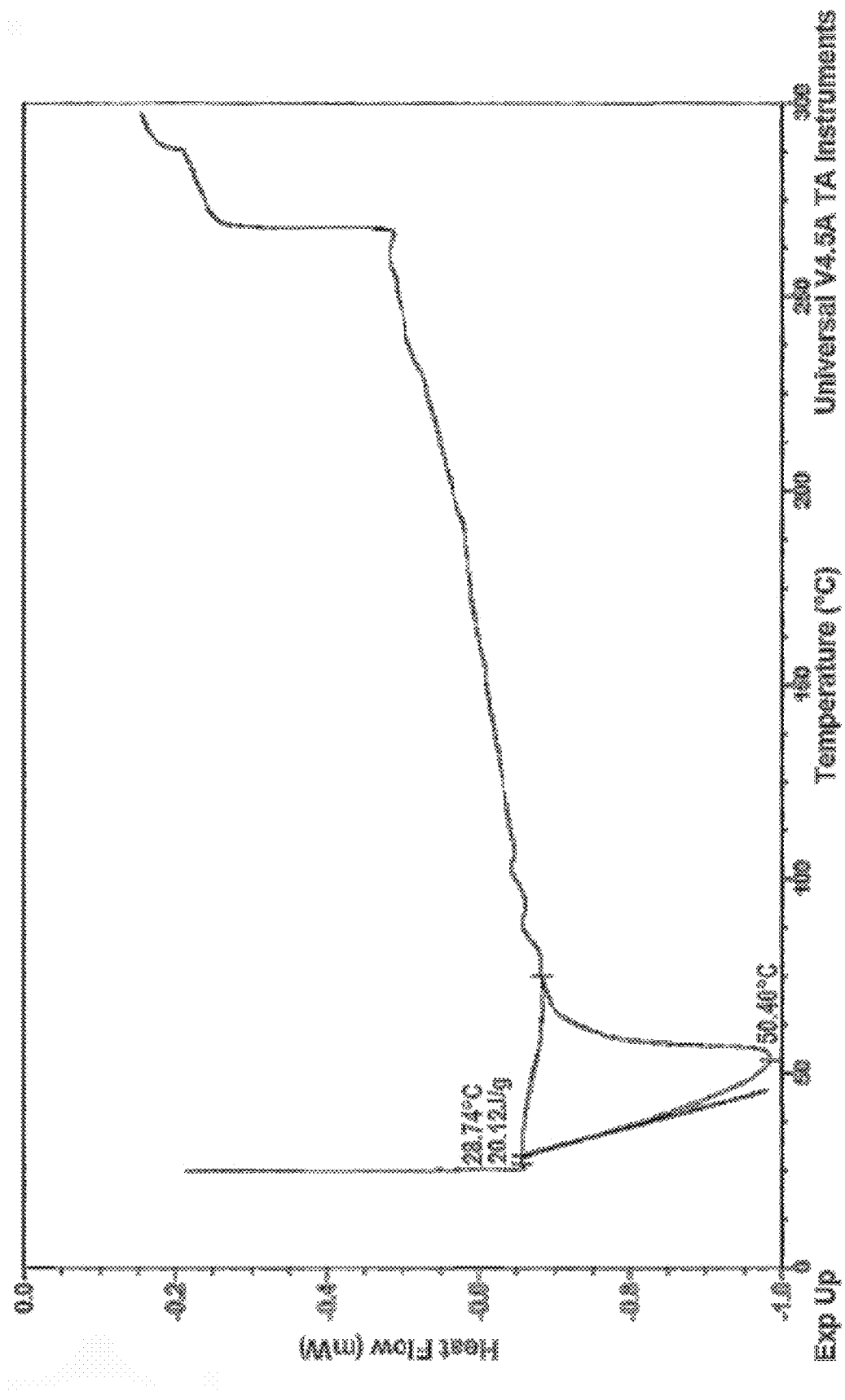
FIG. 9 shows the profile determined by the differential scanning calorimeter method (DSC), of polymorphic form #3 of sodium benzoate from Example 3.

In some embodiments, the polymorphic form of sodium benzoate has a X-ray powder diffraction pattern at a reflection angle 2θ further comprising characteristic peaks at approximately 3.7, 6.3, 6.8, 7.5, 11.7, 17.7, 23.6, 24.5, 26.5, 27.0, 27.7, 28.4, 29.0, 30.2, 31.0, 31.2, 32.3, 34.2, and 35.9 degrees. In some embodiments, the X-ray diffraction pattern can be determined by a period of a scan speed of about 0.1 to 0.3 seconds per step. In some embodiments, the polymorphic form has an X-ray powder diffraction pattern substantially as depicted in FIG. 7. In some embodiments, the X-ray diffraction pattern can be determined by a period of a scan speed of about 0.1 to 0.3 seconds per step. In some embodiments, the polymorphic form has a TGA pattern substantially as depicted in FIG. 8. In some embodiments, the polymorphic form has a DSC pattern substantially as depicted in FIG. 9. In some embodiments, the polymorphic form has an X-ray powder diffraction pattern substantially as depicted in FIG. 7, a TGA pattern substantially as depicted in FIG. 8, and a DSC pattern substantially as depicted in FIG. 9.

Figure 27:
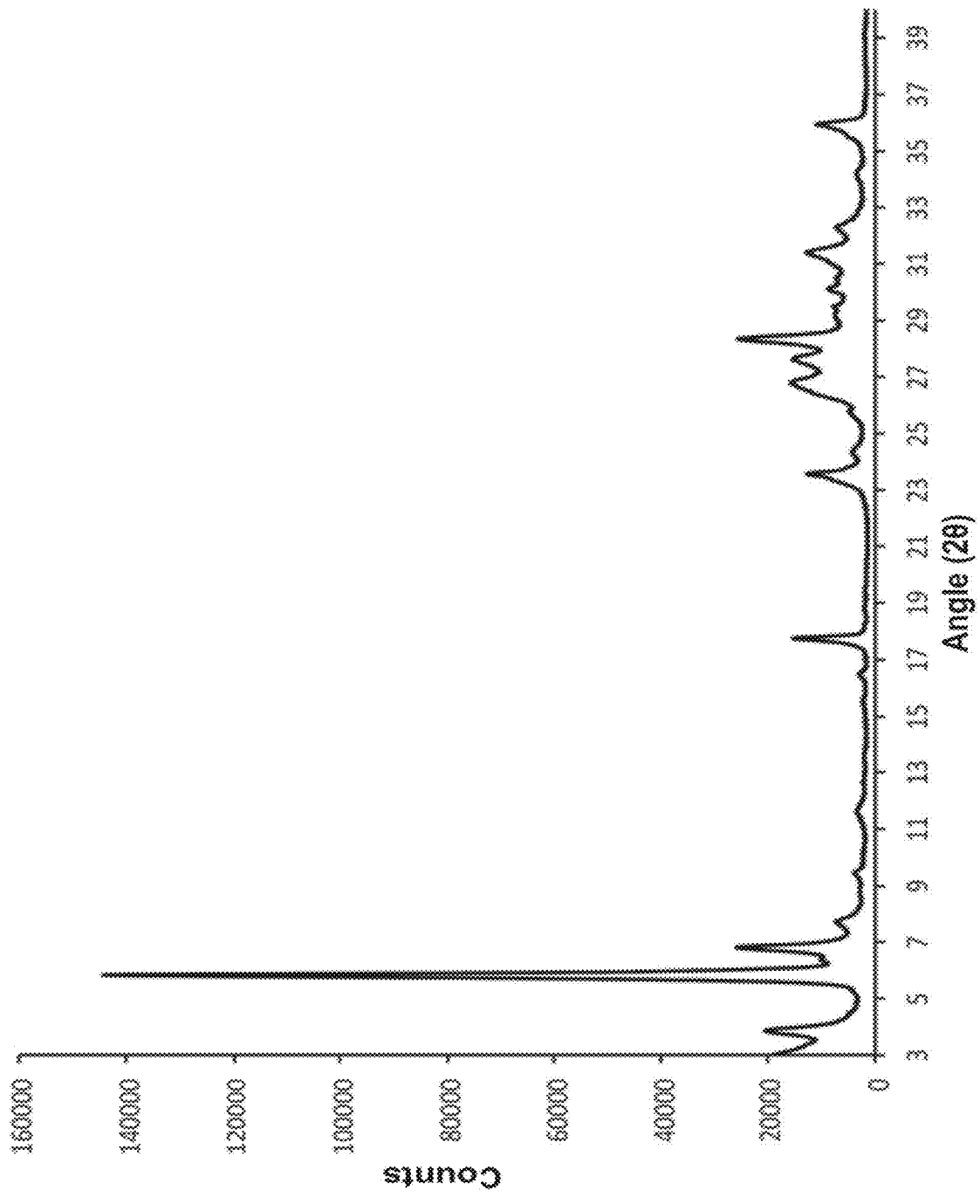
FIG. 27 shows the X-ray powder diffraction (XRPD) of polymorphic form #3 of sodium benzoate from Example 3, with peaks (°) of: 3.7, 5.9, 6.3, 6.8, 7.5, 9.4, 11.7, 16.4, 17.7, 23.6, 24.5, 25.7, 26.7, 27.7, 28.4, 29.0, 29.4, 30.2, 30.4, 31.0, 31.2, 32.3, 34.2, 35.4, and 35.9; wherein the X-ray diffraction pattern is determined by a period of a scan speed of about 1.0 second per step.

In some embodiments, the polymorphic form of sodium benzoate has a X-ray powder diffraction pattern at a reflection angle 2θ further comprising characteristic peaks at approximately 6.3, 9.4, 11.7, 16.4, 23.6, 24.5, 25.7, 28.4, 29.0, 30.4, 31.0, 31.2, 34.2, 35.4, and 35.9 degrees; wherein the X-ray diffraction pattern is determined by a period of a scan speed of about 1.0 second per step. In some embodiments, the polymorphic form has an X-ray powder diffraction pattern substantially as depicted in FIG. 27; wherein the X-ray diffraction pattern is determined by a period of a scan speed of about 1.0 second per step. In some embodiments, the polymorphic form has a TGA pattern substantially as depicted in FIG. 8. In some embodiments, the polymorphic form has a DSC pattern substantially as depicted in FIG. 9. In some embodiments, the polymorphic form has an X-ray powder diffraction pattern substantially as depicted in FIG. 27, a TGA pattern substantially as depicted in FIG. 8, and a DSC pattern substantially as depicted in FIG. 9.

Figure 10:
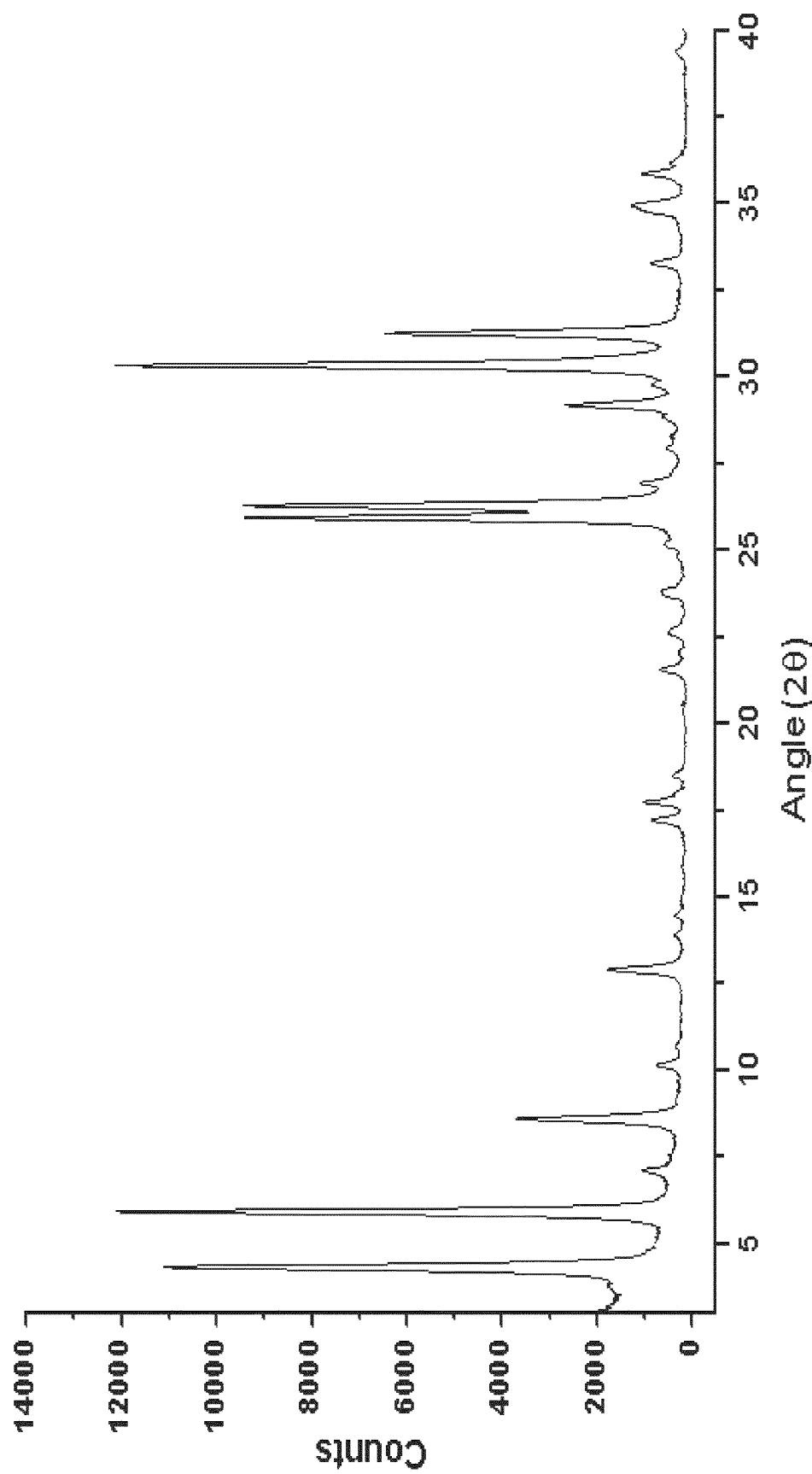
FIG. 10 shows the X-ray powder diffraction (XRPD) of polymorphic form #4 of sodium benzoate from Example 4, with peaks (°) of: 4.3, 5.9, 7.1, 8.6, 10.1, 10.7, 12.9, 13.8, 14.4, 17.2, 17.7, 18.5, 21.5, 22.0, 22.6, 23.7, 25.1, 25.9, 26.2, 26.9, 27.9, 28.2, 28.8, 29.1, 29.7, 30.2, 31.2, 33.2, 34.9, 35.8, 36.1, and 39.3.
Figure 11:
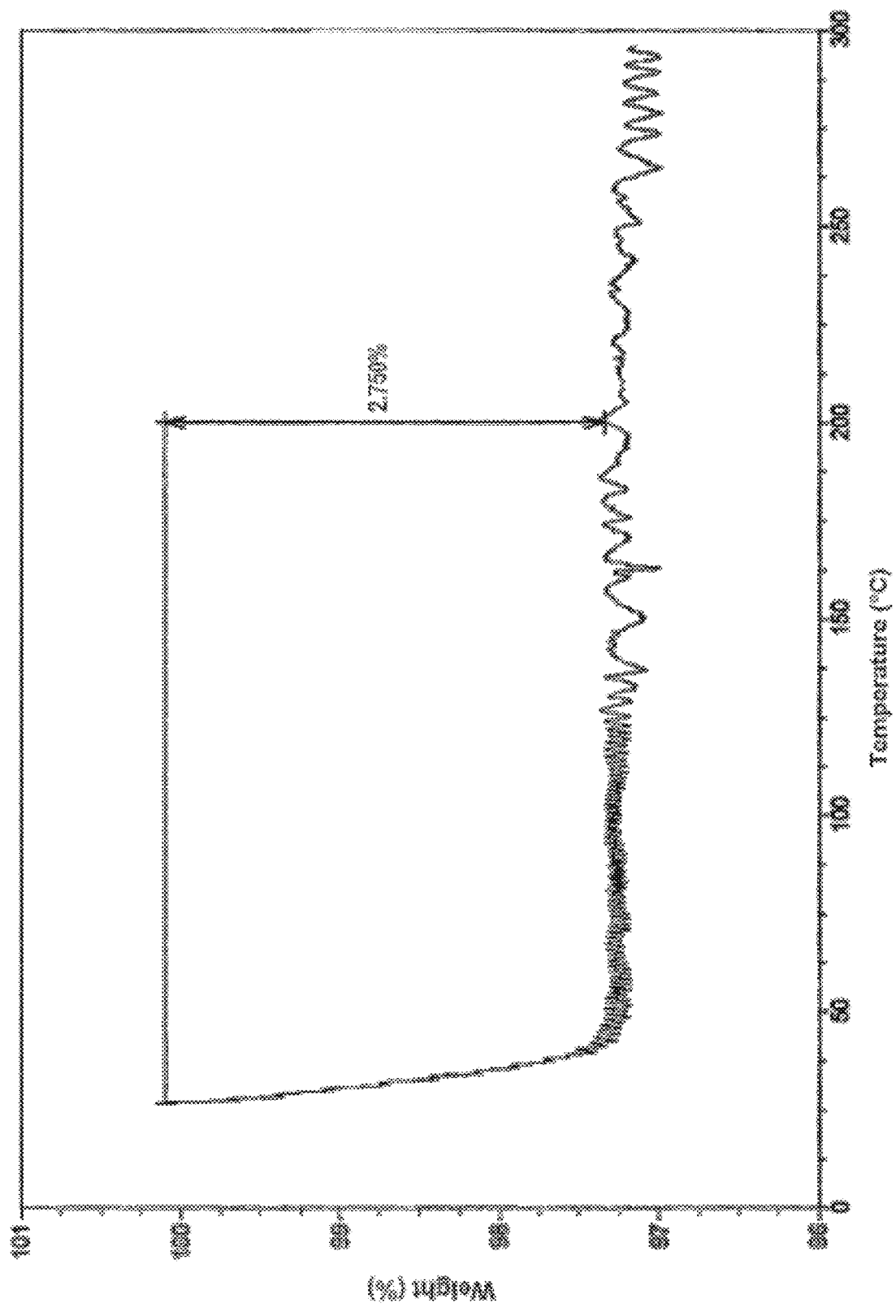
FIG. 11 shows the Thermogravimetric Analysis (TGA) of polymorphic form #4 of sodium benzoate from Example 4.
Figure 12:
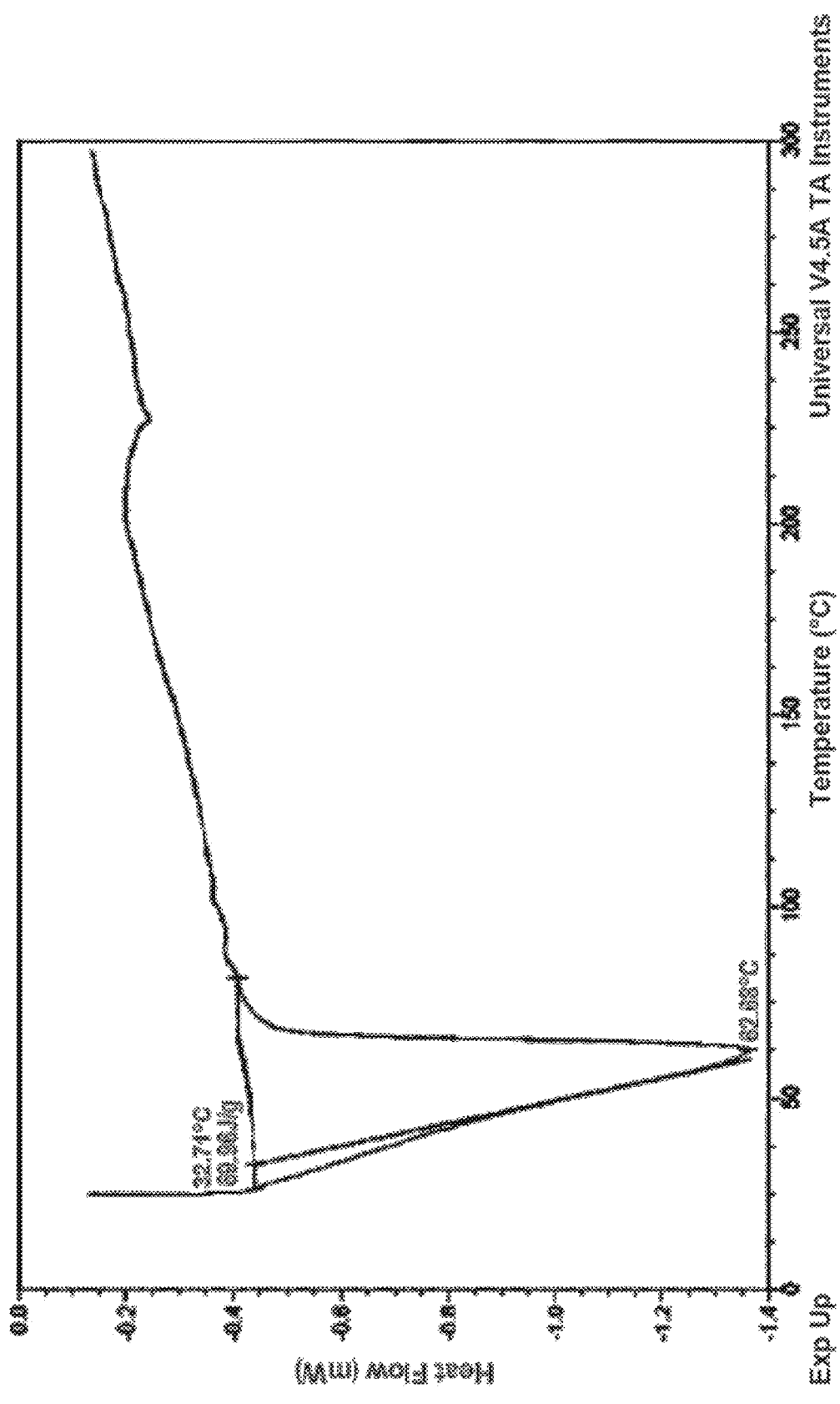
FIG. 12 shows the profile determined by the differential scanning calorimeter method (DSC), of polymorphic form #4 of sodium benzoate from Example 4.

In some embodiments, the polymorphic form of sodium benzoate has a X-ray powder diffraction pattern at a reflection angle 2θ further comprising characteristic peaks at approximately 4.3, 7.1, 8.6, 10.1, 10.7, 12.9, 13.8, 14.4, 17.2, 17.7, 18.5, 21.5, 22.0, 22.6, 23.7, 25.1, 25.9, 26.2, 26.9, 27.9, 28.2, 28.8, 29.1, 29.7, 33.2, 34.9, 35.8, 36.1, and 39.3 degrees. In some embodiments, the X-ray diffraction pattern can be determined by a period of a scan speed of about 0.1 to 0.3 seconds per step. In some embodiments, the polymorphic form has an X-ray powder diffraction pattern substantially as depicted in FIG. 10. In some embodiments, the X-ray diffraction pattern can be determined by a period of a scan speed of about 0.1 to 0.3 seconds per step. In some embodiments, the polymorphic form has a TGA pattern substantially as depicted in FIG. 11. In some embodiments, the polymorphic form has a DSC pattern substantially as depicted in FIG. 12. In some embodiments, the polymorphic form has a X-ray powder diffraction pattern substantially as depicted in FIG. 10, a TGA pattern substantially as depicted in FIG. 11, and a DSC pattern substantially as depicted in FIG. 12.

Figure 13:
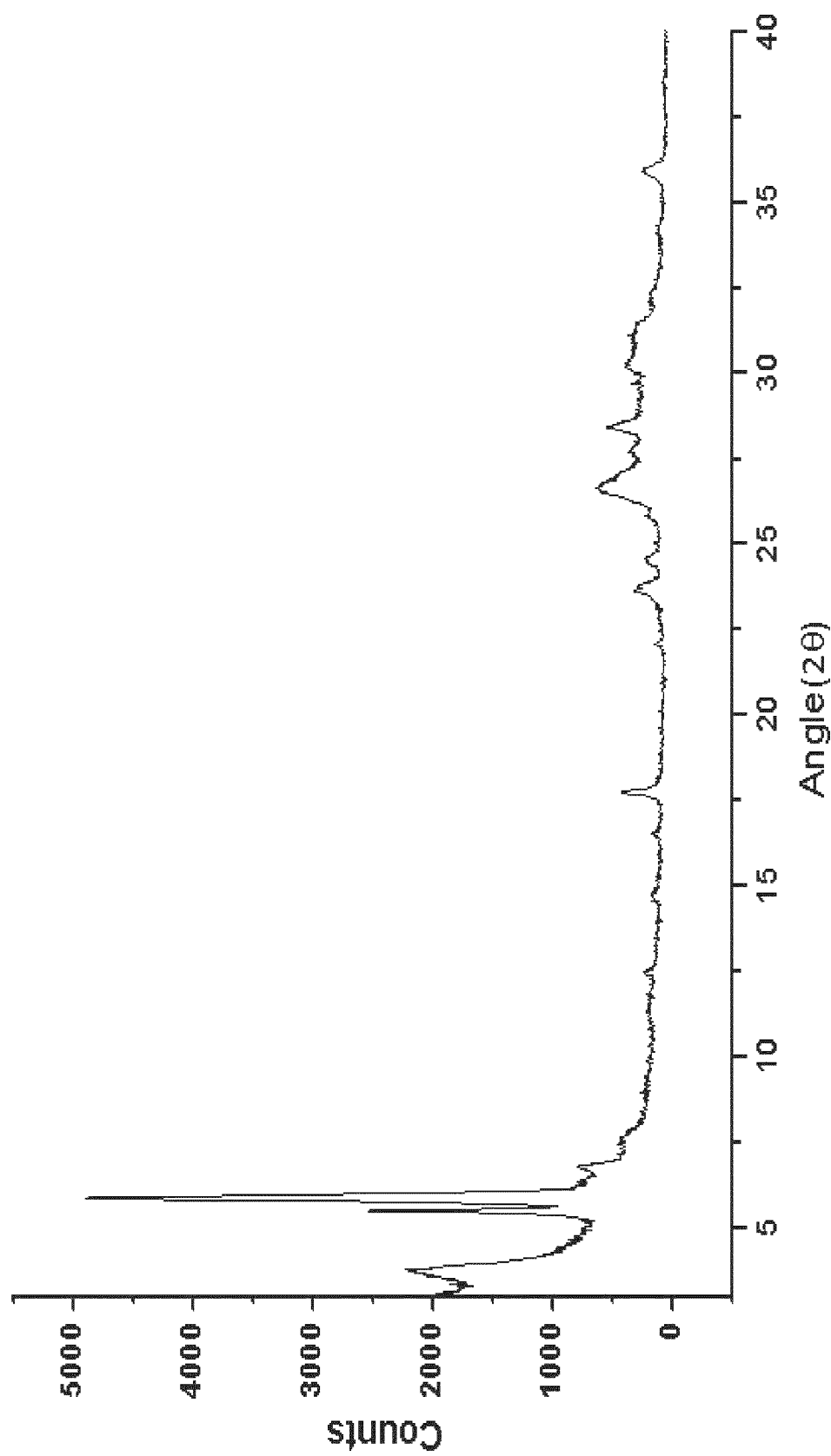
FIG. 13 shows the X-ray powder diffraction (XRPD) of polymorphic form #5 of sodium benzoate from Example 5, with peaks (°) of: 3.7, 5.5, 5.9, 6.7, 7.4, 12.5, 14.7, 16.5, 17.7, 22.0, 23.6, 24.6, 25.8, 26.6, 27.6, 28.4, 30.2, 31.1, 32.3, 34.3, and 35.9.
Figure 14:
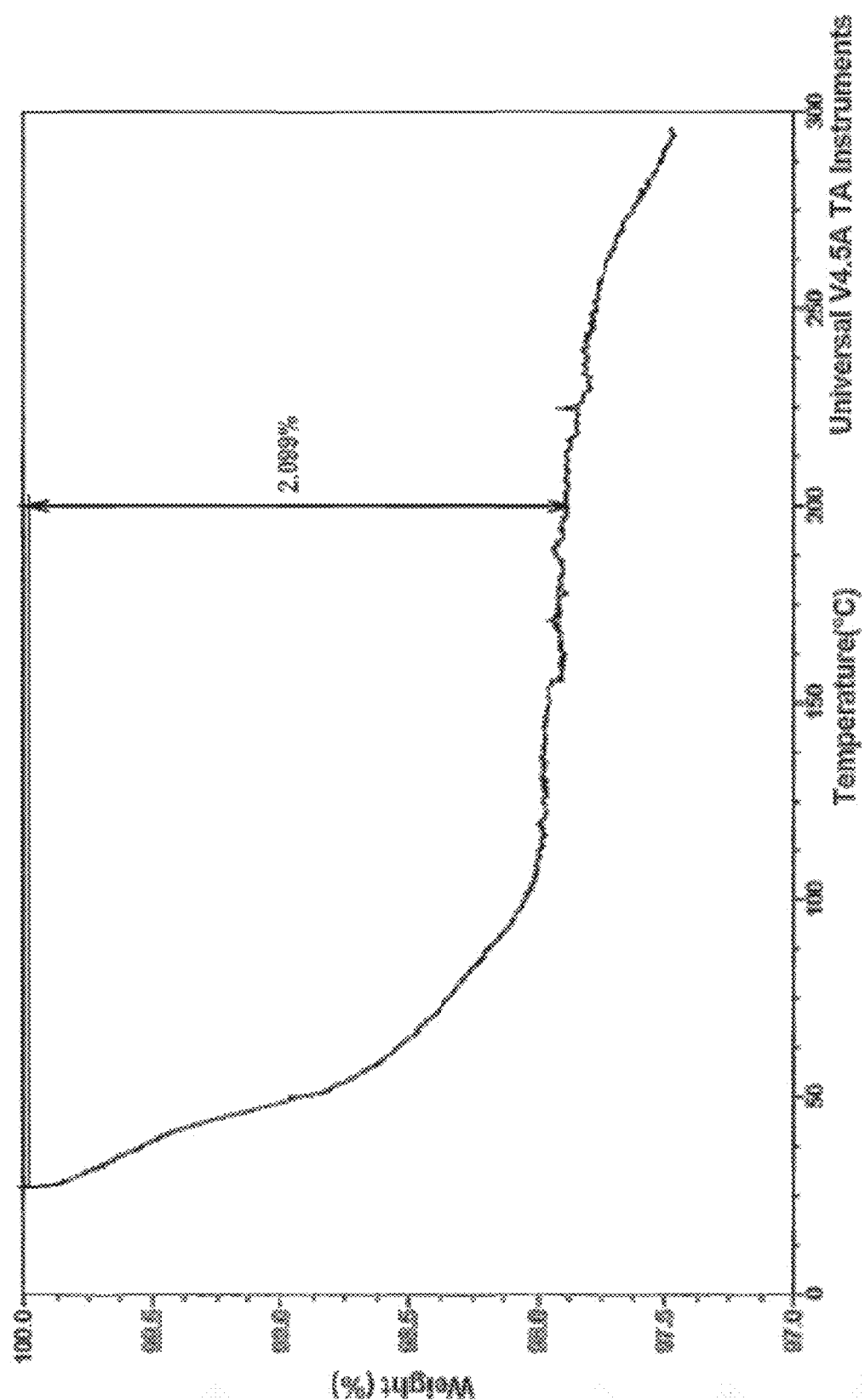
FIG. 14 shows the Thermogravimetric Analysis (TGA) of polymorphic form #5 of sodium benzoate from Example 5.
Figure 15:
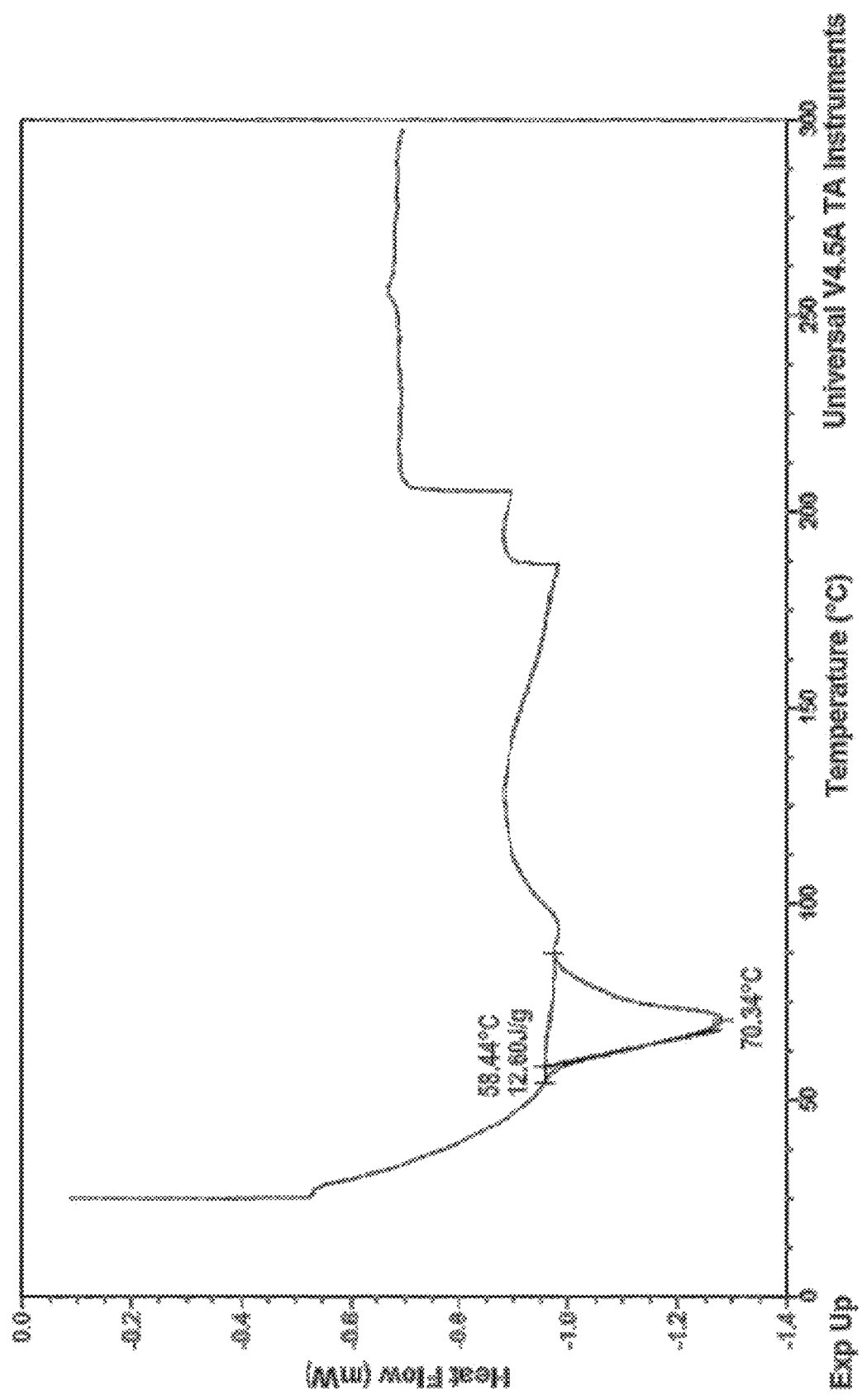
FIG. 15 shows the melting point, as determined by the differential scanning calorimeter method (DSC), of polymorphic form #5 of sodium benzoate from Example 5.

In another aspect, the polymorphic form of sodium benzoate which has an X-ray diffraction pattern comprising characteristic peaks at a reflection angle 2θ of approximately 3.7, 5.9, and 26.6 degrees. In some embodiments, the X-ray diffraction pattern can be determined by a period of a scan speed of about 0.1 to 0.3 seconds per step. In some embodiments, the polymorphic form of sodium benzoate has an X-ray powder diffraction pattern at a reflection angle 2θ further comprising characteristic peaks at approximately 5.5, 6.7, 7.4, 12.5, 14.7, 16.5, 17.7, 22.0, 23.6, 24.6, 25.8, 27.6, 28.4, 30.2, 31.1, 32.3, 34.3, and 35.9 degrees. In some embodiments, the X-ray diffraction pattern can be determined by a period of a scan speed of about 0.1 to 0.3 seconds per step. In some embodiments, the polymorphic form has an X-ray powder diffraction pattern substantially as depicted in FIG. 13. In some embodiments, the X-ray diffraction pattern can be determined by a period of a scan speed of about 0.1 to 0.3 seconds per step. In some embodiments, the polymorphic form has a TGA pattern substantially as depicted in FIG. 14. In some embodiments, the polymorphic form has a DSC pattern substantially as depicted in FIG. 15. In some embodiments, the polymorphic form has an X-ray powder diffraction pattern substantially as depicted in FIG. 13, a TGA pattern substantially as depicted in FIG. 14, and a DSC pattern substantially as depicted in FIG. 15.

Figure 16:
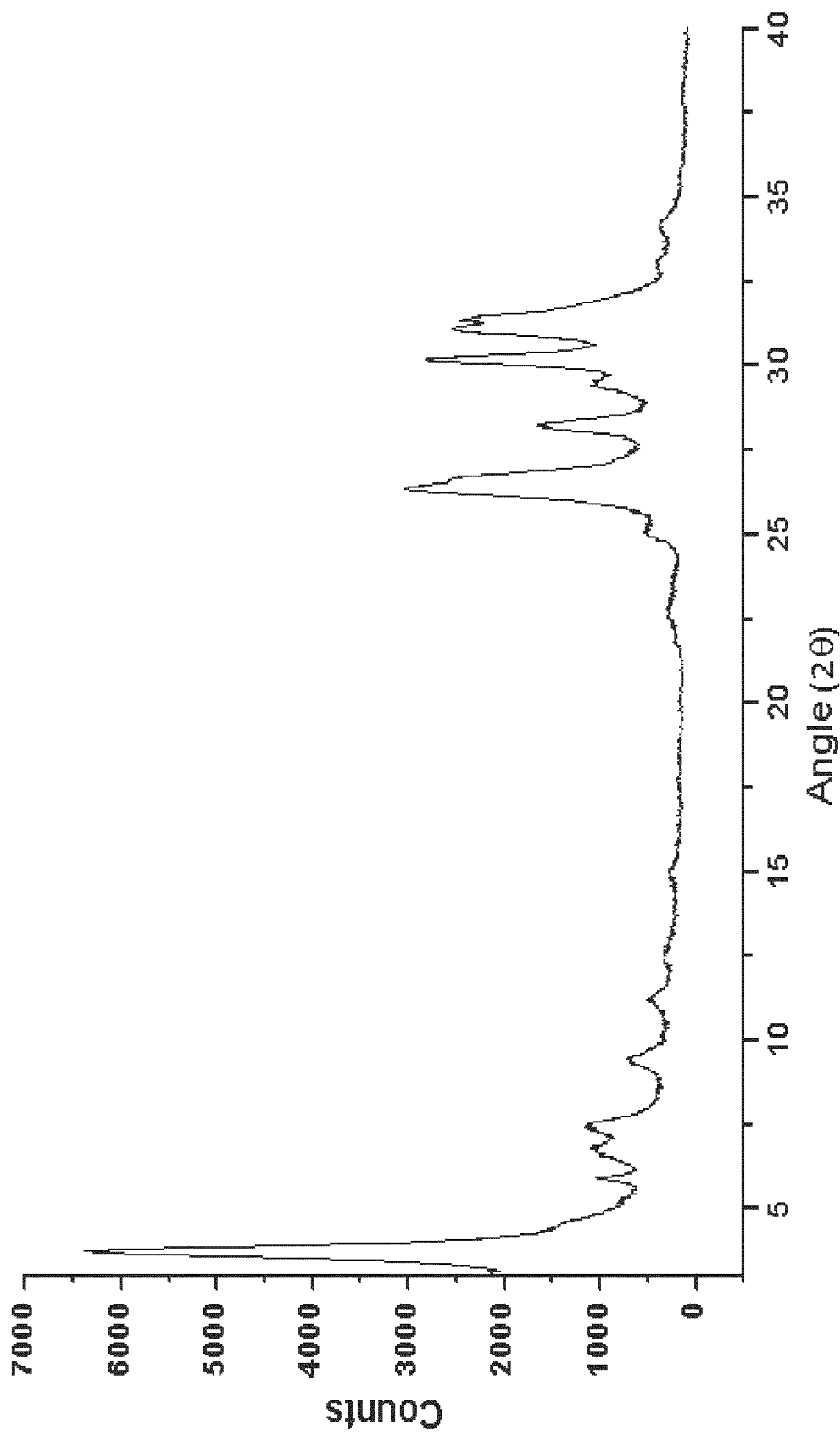
FIG. 16 shows the X-ray powder diffraction (XRPD) of polymorphic form #6 of sodium benzoate from Example 6, with peaks (°) of: 3.7, 5.9, 6.6, 7.4, 9.4, 11.2, 12.5, 22.8, 25.1, 26.3, 28.2, 29.5, 30.2, 31.1, 31.2, 33.0, and 34.0.
Figure 17:
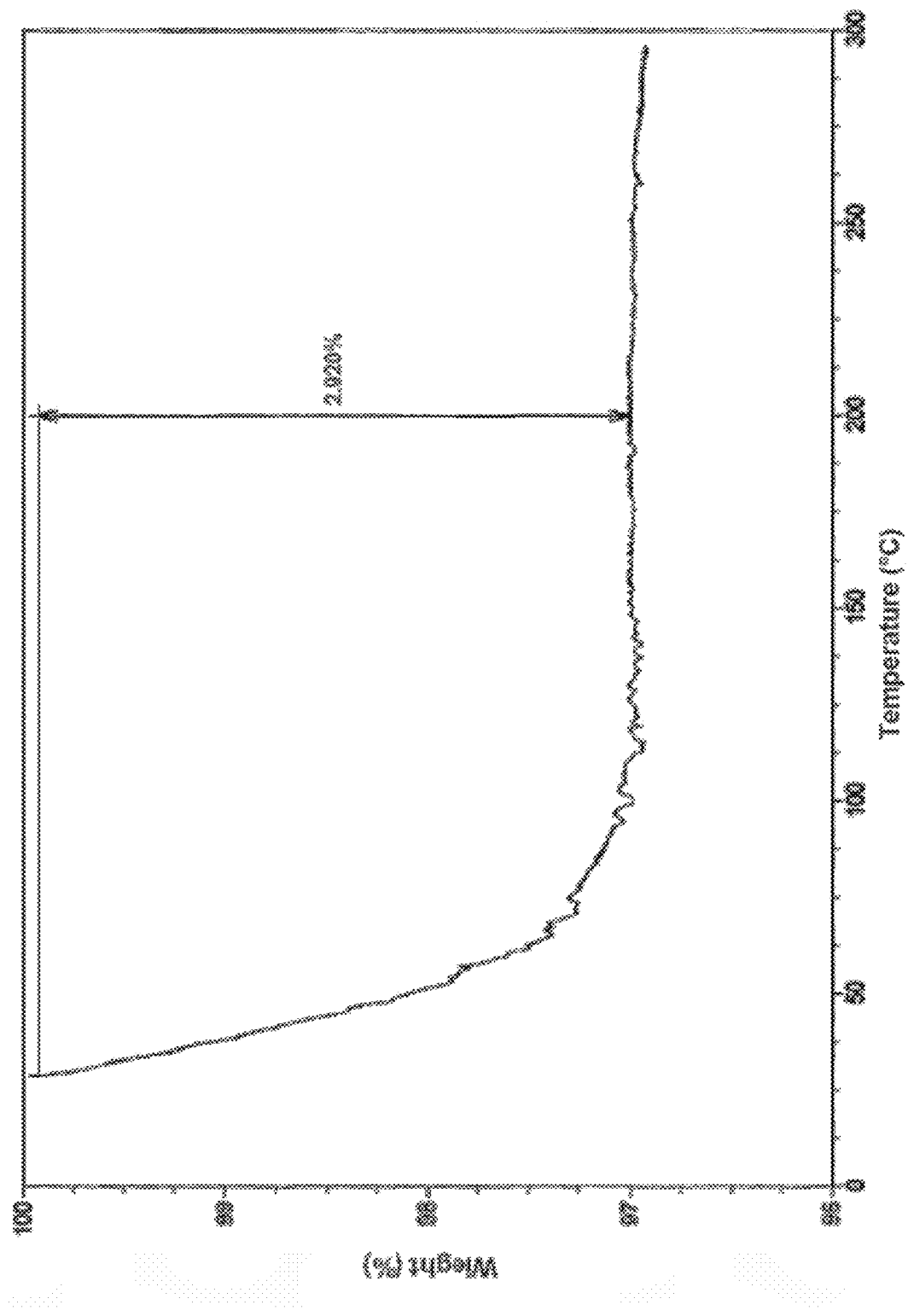
FIG. 17 shows the Thermogravimetric Analysis (TGA) of polymorphic form #6 of sodium benzoate from Example 6.
Figure 18:
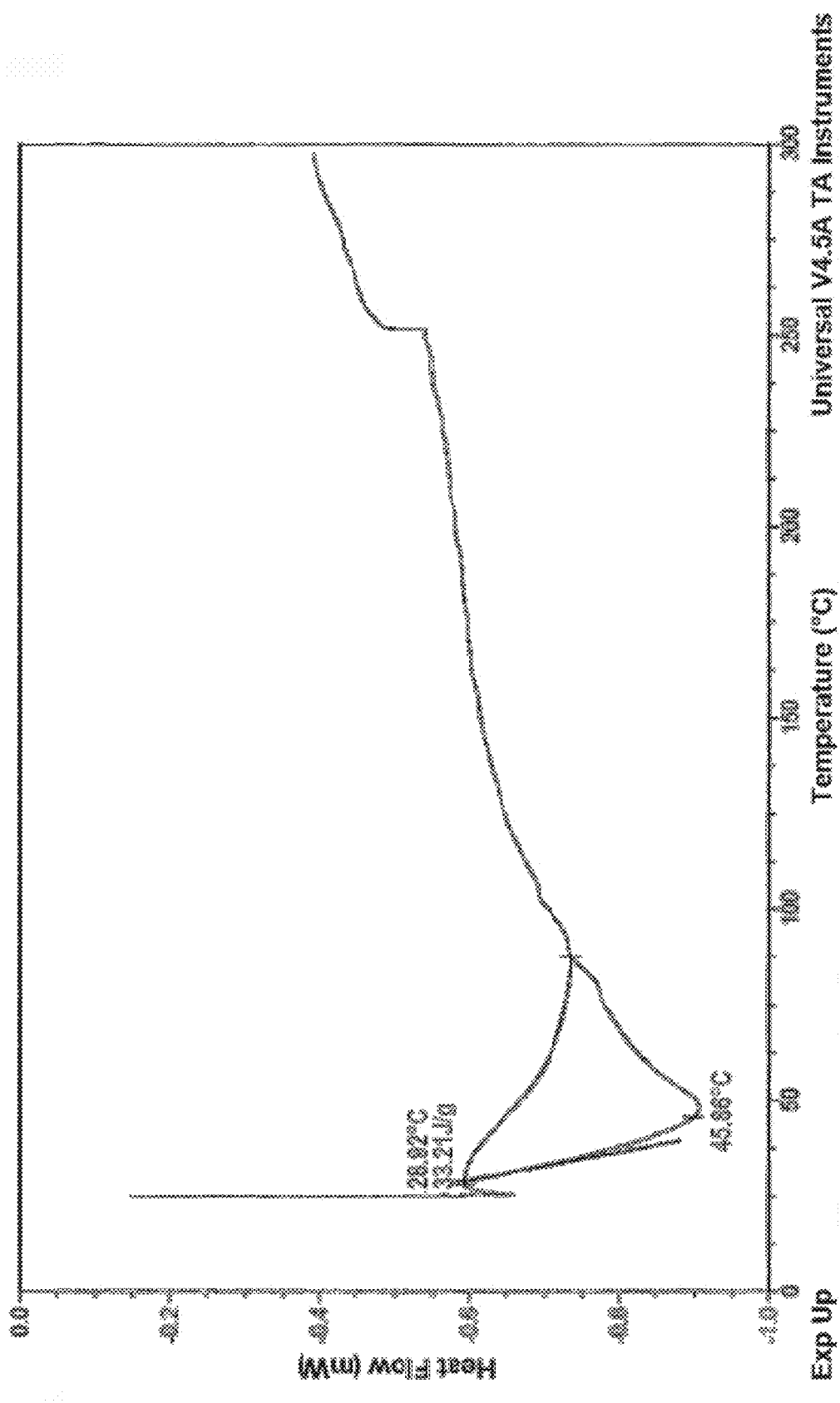
FIG. 18 shows the melting point, as determined by the differential scanning calorimeter method (DSC), of polymorphic form #6 of sodium benzoate from Example 6.

In some embodiments, the polymorphic form of sodium benzoate has an X-ray powder diffraction pattern at a reflection angle 2θ further comprising characteristic peaks at approximately 6.6, 7.4, 9.4, 11.2, 12.5, 22.8, 25.1, 26.3, 28.2, 29.5, 30.2, 31.1, 31.2, 33.0, and 34.0 degrees. In some embodiments, the X-ray diffraction pattern can be determined by a period of a scan speed of about 0.1 to 0.3 seconds per step. In some embodiments, the polymorphic form has a X-ray powder diffraction pattern substantially as depicted in FIG. 16. In some embodiments, the X-ray diffraction pattern can be determined by a period of a scan speed of about 0.1 to 0.3 seconds per step. In some embodiments, the polymorphic form has a TGA pattern substantially as depicted in FIG. 17. In some embodiments, the polymorphic form has a DSC pattern substantially as depicted in FIG. 18. In some embodiments, the polymorphic form has an X-ray powder diffraction pattern substantially as depicted in FIG. 16, a TGA pattern substantially as depicted in FIG. 17, and a DSC pattern substantially as depicted in FIG. 18.

Figure 28:
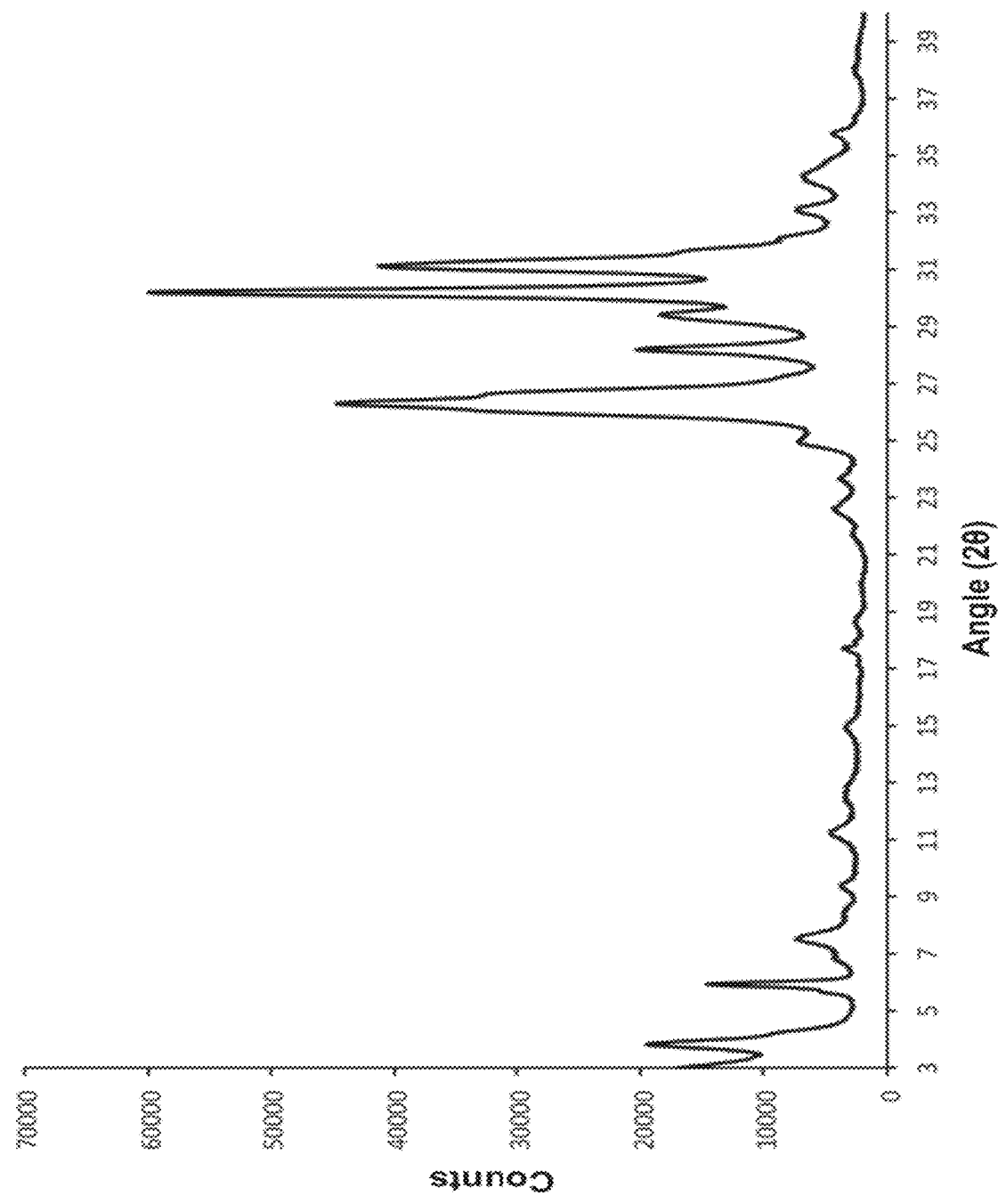
FIG. 28 shows the X-ray powder diffraction (XRPD) of polymorphic form #6 of sodium benzoate from Example 6, with peaks (°) of: 3.7, 4.2, 5.6, 5.9, 6.6, 7.4, 8.4, 9.4, 11.2, 12.5, 14.8, 17.6, 18.6, 21.6, 22.8, 23.6, 25.1, 26.3, 26.5, 27.1, 28.2, 29.5, 30.2, 31.1, 31.3, 32.0, 33.0, 34.0, 35.7, and 38.0; wherein the X-ray diffraction pattern is determined by a period of a scan speed of about 1.0 second per step.

In some embodiments, the polymorphic form of sodium benzoate has an X-ray powder diffraction pattern at a reflection angle 2θ further comprising characteristic peaks at approximately 4.2, 5.6, 5.9, 6.6, 8.4, 9.4, 12.5, 17.6, 18.6, 21.6, 22.8, 23.6, 25.1, 27.1, 28.2, 30.2, 31.1, 31.3, 32.0, 34.0, and 38.0 degrees; wherein the X-ray diffraction pattern is determined by a period of a scan speed of about 1.0 second per step. In some embodiments, the polymorphic form has a X-ray powder diffraction pattern substantially as depicted in FIG. 28; wherein the X-ray diffraction pattern is determined by a period of a scan speed of about 1.0 second per step. In some embodiments, the polymorphic form has a TGA pattern substantially as depicted in FIG. 17. In some embodiments, the polymorphic form has a DSC pattern substantially as depicted in FIG. 18. In some embodiments, the polymorphic form has an X-ray powder diffraction pattern substantially as depicted in FIG. 28, a TGA pattern substantially as depicted in FIG. 17, and a DSC pattern substantially as depicted in FIG. 18.

In some embodiments, the polymorphic form of sodium benzoate is prepared by a process comprising (i) dissolving sodium benzoate in a polar solvent, to form a slurry, and (ii) stirring the slurry for approximately 10 minutes to approximately 6 days to produce the polymorphic form of sodium benzoate, and (iii) filtering and collecting the solid thus formed. In some embodiments, the process further comprises adding acetonitrile after the sodium benzoate is dissolved in the solvent in step (i). In some embodiments, the process further comprises adding acetonitrile after the sodium benzoate is dissolved in methanol. In some embodiments, in step (i) of the process, the solvent comprises methanol and the process further comprises adding acetonitrile after the sodium benzoate is dissolved in the solvent in step (i). In some embodiments, the polar solvent comprises methanol, acetonitrile, or isobutanol, or a combination thereof. In some embodiments, the polar solvent comprises water. In some embodiments, the polar solvent does not comprise water. In some embodiments, the polar solvent comprises methanol, acetonitrile, or isobutanol, or a combination thereof, and no water.

In some embodiments, in step (i), the solvent comprises methanol. In some embodiments, the sodium benzoate is dissolved in methanol in step (i) and wherein in step (ii) the stirring of the slurry is for approximately 10 minutes, or for approximately 2 days to approximately 6 days. In some embodiments, the sodium benzoate is dissolved in methanol in step (i) and wherein in step (ii) the stirring of the slurry is for approximately 10 minutes, or for approximately 2 days to approximately 4 days. In some embodiments, the sodium benzoate is dissolved in methanol in step (i) and wherein in step (ii) the stirring of the slurry is for approximately 10 minutes. In some embodiments, in step (i), the solvent comprises acetonitrile. In some embodiments, the sodium benzoate is dissolved in acetonitrile in step (i) and wherein in step (ii) the stirring of the slurry is for approximately 2 days. In some embodiments, the sodium benzoate is dissolved in acetonitrile in step (i) and wherein in step (ii) the stirring of the slurry is for approximately 2 days to approximately 4 days. In some embodiments, in step (i), the solvent comprises isobutanol. In some embodiments, the sodium benzoate is dissolved in isobutanol in step (i) and wherein in step (ii) the stirring of the slurry is for approximately 2 days to approximately 6 days. In some embodiments, the sodium benzoate is dissolved in isobutanol in step (i) and wherein in step (ii) the stirring of the slurry is for approximately 4 days to approximately 6 days. In some embodiments, the sodium benzoate is dissolved in isobutanol in step (i) and wherein in step (ii) the stirring of the slurry is for approximately 6 days. In some embodiments, wherein the sodium benzoate is dissolved in methanol in step (i), wherein step (ii) comprises further adding the acetonitrile after the sodium benzoate is dissolved in methanol, and wherein in step (ii) the stirring of the slurry is for approximately 2 days. In some embodiments, wherein the sodium benzoate is dissolved in methanol in step (i), wherein step (ii) comprises further adding the acetonitrile after the sodium benzoate is dissolved in methanol, and wherein in step (ii) the stirring of the slurry is for approximately 2 days to approximately 6 days. In some embodiments, in the process, the sodium benzoate is dissolved in methanol in step (i), the process further comprises adding acetonitrile after the sodium benzoate is dissolved in methanol in step (i), and wherein in step (ii) the stirring of the slurry is for approximately 2 days to approximately 4 days.

Any of the polymorphic forms of sodium benzoate described herein has a chemical purity of about 95%, 97%, 98%, 99%, 99.5%, 99.9% or higher, which can be determined by a conventional method, for example, HPLC or $^1$H Nuclear Magnetic Resonance ($^1$H-NMR) spectroscopy. In some embodiments, the polymorphic form of sodium benzoate described herein contains less than 10%, preferably less than 5%, preferably less than 1%, preferably less than 0.5%, and most preferably less than 0.1% of sodium benzoate in other polymorphic or amorphous forms (as measured by XRPD or DSC).

Compositions

The present disclosure provides a pharmaceutical composition comprising an effective amount of a sodium benzoate compound and an effective amount of clozapine. In certain embodiments, the pharmaceutical composition comprises 50 to 1000 mg of sodium benzoate compound (e.g., 100 to 800 mg, 200 to 600 mg, or 300 to 500 mg) and 25 to 300 mg of clozapine (e.g., 50 to 250 mg, 100 to 200 mg, or 150-300 mg). In certain embodiments, the pharmaceutical composition comprises 500 mg of sodium benzoate compound and 200 to 300 mg of clozapine.

In some embodiments, the sodium benzoate compound (e.g., sodium benzoate) can be in amorphous form, or in one or more polymorphic forms. In some examples, the sodium benzoate can be mixture of amorphous form and one or more polymorphic forms. In one example, the sodium benzoate compound can be a commercially available sodium benzoate, which may include amorphous and a variety of polymorphic forms of sodium benzoate (e.g. purchased from Merck, Formosa, Sigma Aldrich, and the like), and the purified polymorphic form of sodium benzoate of the invention. In some embodiments, the sodium benzoate compound comprises a polymorphic form of sodium benzoate as described herein.

The present disclosure also provides compositions comprising a polymorphic form of sodium benzoate described herein, and a carrier, excipient, diluent, binder, additive, filler, and lubricant, or a mixture thereof. In certain embodiments, the composition comprises a polymorphic form of sodium benzoate described herein and a pharmaceutically acceptable carrier. In certain embodiments, the composition comprises a polymorphic form of sodium benzoate described herein and a pharmaceutically acceptable excipient. In certain embodiments, the composition comprises a polymorphic form of sodium benzoate described herein and a pharmaceutically acceptable diluent. In certain embodiments, the composition comprises a polymorphic form of sodium benzoate described herein and a pharmaceutically acceptable binder. In certain embodiments, the composition comprises a polymorphic form of sodium benzoate described herein and a pharmaceutically acceptable additive. In certain embodiments, the composition comprises a polymorphic form of sodium benzoate described herein and a pharmaceutically acceptable filler. In certain embodiments, the composition comprises a polymorphic form of sodium benzoate described herein and a pharmaceutically acceptable lubricant.

In certain embodiments, the pharmaceutical composition described herein further comprises one or more pharmaceutically acceptable excipients. In certain embodiments, the pharmaceutical composition comprises 50 to 1000 mg of sodium benzoate compound, 25 to 300 mg of clozapine, and one or more pharmaceutically acceptable excipients. In certain embodiments, the pharmaceutical composition comprises 500 mg of sodium benzoate compound, 200 to 300 mg of clozapine, and one or more pharmaceutically acceptable excipients.

In certain embodiments, the ratio of the sodium benzoate compound to clozapine is about 1:10 to about 1000:1, about 1:10 to about 900:1, about 1:10 to about 800:1, about 1:10 to about 600:1, about 1:10 to about 500:1, about 1:10 to about 400:1, about 1:10 to about 200:1, about 1:10 to about 100:1, about 1:10 to about 75:1, about 1:10 to about 50:1, about 1:10 to about 25:1, about 1:10 to about 10:1, about 1:10 to about 5:1, about 1:10 to about 1:2, about 1:10 to about 1:5, or about 1:10 to about 1:8 by weight. In certain embodiments, the ratio of the sodium benzoate compound to clozapine is about 20:1, about 5:1, about 2.5:1, or about 1.67:1 by weight.

In certain embodiments, the sodium benzoate compound described herein is provided in an effective amount in the pharmaceutical composition. In certain embodiments, clozapine is provided in an effective amount in the pharmaceutical composition. In certain embodiments, the effective amount is a therapeutically effective amount (e.g., amount effective for treating and/or reducing the risk for a neuropsychiatric disorder in a subject in need thereof). In certain embodiments, the effective amount is a prophylactically effective amount (e.g., amount effective for preventing a neuropsychiatric disorder in a subject in need thereof).

In certain embodiments, the pharmaceutical composition disclosed herein comprises 50 to 1000 mg of sodium benzoate (e.g., 100 to 800 mg, 200 to 600 mg, or 300 to 500 mg), 25-300 mg of clozapine (e.g., 50 to 200 mg, 100 to 150 mg, or 150 to 300 mg), 50-500 mg of sodium alginate (e.g., 100 to 400 mg, 200 to 300 mg, or 250 to 400 mg), 50-400 mg of sodium citrate (e.g., 100-300 mg, 150-250 mg, or 200-300 mg), 5-100 mg of magnesium stearate (e.g., 10-80 mg, 25-70 mg, 40-60 mg, or 50-100 mg), and 80-200 mg of sodium starch glycolate (e.g., 100-150 mg). In certain embodiments, the pharmaceutical composition disclosed herein comprises 125 to 500 mg of sodium benzoate, 25-300 mg of clozapine, 50-500 mg of sodium alginate, 50-400 mg of sodium citrate, 5-100 mg of magnesium stearate, and 80-200 mg of sodium starch glycolate.

In certain embodiments, the pharmaceutical composition disclosed herein comprises 50 to 1000 mg of sodium benzoate, 25-300 mg of clozapine, 50-200 mg of sodium alginate, 50-400 mg of sodium citrate, 5-100 mg of magnesium stearate, and 80-200 mg of sodium starch glycolate. In certain embodiments, the pharmaceutical composition disclosed herein comprises 125 to 500 mg of sodium benzoate, 25-300 mg of clozapine, 50-200 mg of sodium alginate, 50-400 mg of sodium citrate, 5-100 mg of magnesium stearate, and 80-200 mg of sodium starch glycolate.

In certain embodiments, the pharmaceutical composition disclosed herein comprises 50 to 1000 mg of sodium benzoate, 25-300 mg of clozapine, 50-70 mg of sodium alginate, 50-70 mg of sodium citrate, 5-15 mg of magnesium stearate, and 80-100 mg of sodium starch glycolate. In certain embodiments, the pharmaceutical composition disclosed herein comprises 125 to 500 mg of sodium benzoate, 25-300 mg of clozapine, 50-70 mg of sodium alginate, 50-70 mg of sodium citrate, 5-15 mg of magnesium stearate, and 80-100 mg of sodium starch glycolate.

In certain embodiments, the composition further comprises a neuropharmaceutical. In certain embodiments, the neuropharmaceutical is selected from the group consisting of butyrophenone, phenothiazine, fluphenazine, perphenazine, prochlorperazine, thioridazine, trifluoperazine, mesoridazine, promazine, triflupromazine, levomepromazine, promethazine, thioxanthene, chlorprothixene, flupenthixol, thiothixene, zuclopenthixol, clozapine, olanzapine, risperidone, quetiapine, ziprasidone, amisulpride, asenapine, paliperidone, aripiprazole, cariprazine, brexpiprazole, lamotrigine, tetrabenazine, cannabidiol, LY2140023, droperidol, pimozide, butaperazine, carphenazine, eemoxipride, piperacetazine, sulpiride, acamprosate, tetrabenazine, vilazodone, levomilnacipran, and vortioxetine, fluoxetine, paroxetine, escitalopram, citalopram, sertraline, fluvoxamine, venlafaxine, milnacipram, duloxetine, mirtazapine, mianserin, reboxetine, bupropion, amitriptyline, nortriptiline, protriptyline, desipramine, trimipramine, amoxapine, clomipramine, desipramine, doxepin, isocarboxazid, tranylcypromine, trazodone, nefazodone, lamatrogine, lithium, topiramate, gabapentin, carbamazepine, oxacarbazepine, valporate, maprotiline, mirtazapine, brofaromine, gepirone, moclobemide, isoniazid, iproniazid, phenelzine, selegiline, a statin, an amphetamine, modafinil, desoxyn, methamphetamine, cocaine, arecoline, dexmethylphenidate, dextroamphetamine, methylphenidate, lisdexamfetamine dimesylate, mixed salts amphetamine, atomoxetine, clonidine hydrochloride, guanfacine hydrochloride, arecoline, pemoline, donepezil, tacrine, rivastigmine, memantine, physostigmine, lithium salts, nicotine, arecoline, huperzine alpha, riluzole, sarcosine, vitamin C, vitamin E, carotenoids, tannic acid, and *Ginkgo biloba* extract. The compositions described herein are useful in treating and/or reducing the risk for a neuropsychiatric disorder. In certain embodiments, the ratio of the polymorphic form of sodium benzoate to the neuropharmaceutical is about 1:10 to about 1000:1, about 1:10 to about 900:1, about 1:10 to about 800:1, about 1:10 to about 600:1, about 1:10 to about 500:1, about 1:10 to about 400:1, about 1:10 to about 200:1, about 1:10 to about 100:1, about 1:10 to about 75:1, about 1:10 to about 50:1, about 1:10 to about 25:1, about 1:10 to about 10:1, about 1:10 to about 5:1, about 1:10 to about 1:2, about 1:10 to about 1:5, or about 1:10 to about 1:8 by weight.

In certain embodiments, the composition is a pharmaceutical composition. In certain embodiments, the composition is a nutraceutical composition. In certain embodiments, the composition is a health food. In some embodiments, the compositions described herein can be a health food or health food product, which can be any kinds of liquid and solid/semi-solid materials that are used for nourishing humans and animals, for improving basic behavioral functioning, hyperactivity, mood, anxiety, depression, perception, sensorimotor gating, pain threshold, memory and/or cognitive functioning, or for facilitating treatment of any of the target diseases noted herein (e.g., a neuropsychiatric disorder, including those described herein). The health food product may be a food product (e.g., tea-based beverages, juice, soft drinks, coffee, milk, jelly, cookies, cereals, chocolates, snack bars, herbal extracts, dairy products (e.g., ice cream, and yogurt)), a food/dietary supplement, or a nutraceutical formulation.

The health food product described herein, may comprise one or more edible carriers, which confer one or more of the benefits to the product as described herein. Examples of edible carriers include starch, cyclodextrin, maltodextrin, methylcellulose, carbonmethoxy cellulose, xanthan gum, and aqueous solutions thereof. Other examples include solvents, dispersion media, coatings, surfactants, antioxidants, preservatives (e.g., antibacterial agents, antifungal agents), isotonic agents, absorption delaying agents, stabilizers, gels, binders, excipients, disintegration agents, lubricants, sweetening agents, flavoring agents, dyes, such like materials and combinations thereof, as would be known to one of ordinary skill in the art. In some examples, the health food products described herein may further include neuroprotective foods, such as fish oil, flax seed oil, and/or benzoate.

In some examples, the health food product is a nutraceutical composition, which refers to compositions containing components from food sources and conferring extra health benefits in addition to the basic nutritional value found in foods. A nutraceutical composition as described herein comprises the polymorphic form described herein (e.g., the sodium benzoate compound and polymorphic form as described herein) and additional ingredients and supplements that promote good health and/or enhance stability and bioactivity of the polymorphic forms.

The actions of nutraceutical compositions may be fast or/and short-term or may help achieve long-term health objectives as those described herein, e.g., improving basic behavioral functioning, hyperactivity, mood, anxiety, depression, perception, sensorimotor gating, pain threshold, memory and/or cognitive functioning in, e.g., human subjects who have or are at risk for a neuropsychiatric disorder. The nutraceutical compositions may be contained in an edible material, for example, as a dietary supplement or a pharmaceutical formulation. As a dietary supplement, additional nutrients, such as vitamins, minerals or amino acids may be included. The composition can also be a drink or a food product, e.g., tea, soft drink, juice, milk, coffee, cookie, cereal, chocolate, and snack bar. If desired, the composition can be sweetened by adding a sweetener such as sorbitol, maltitol, hydrogenated glucose syrup and hydrogenated starch hydrolyzate, high fructose corn syrup, cane sugar, beet sugar, pectin, or sucralose.

The nutraceutical composition disclosed herein can be in the form of a solution. For example, the nutraceutical formulation can be provided in a medium, such as a buffer, a solvent, a diluent, an inert carrier, an oil, or a creme. In some examples, the formulation is present in an aqueous solution that optionally contains a non-aqueous co-solvent, such as an alcohol. The nutraceutical composition can also be in the form of powder, paste, jelly, capsule, or tablet. Lactose and corn starch are commonly used as diluents for capsules and as carriers for tablets. Lubricating agents, such as magnesium stearate, are typically added to form tablets.

The health food products may be formulated for a suitable administration route, for example, oral administration. For oral administration, the composition can take the form of, for example, tablets or capsules, prepared by conventional means with acceptable excipients such as binding agents (for example, pregelatinised maize starch, polyvinylpyrrolidone or hydroxypropyl methylcellulose); fillers (for example, lactose, microcrystalline cellulose or calcium hydrogen phosphate); lubricants (for example, magnesium stearate, talc or silica); disintegrants (for example, potato starch or sodium starch glycolate); or wetting agents (for example, sodium lauryl sulphate). The tablets can be coated by methods well known in the art. Also included are bars and other chewable formulations.

In some examples, the health food product can be in a liquid form and the one or more edible carriers can be a solvent or dispersion medium comprising but not limited to, ethanol, polyol (e.g., glycerol, propylene glycol, liquid polyethylene glycol), lipids (e.g., triglycerides, vegetable oils, liposomes) or combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof. In many cases, it will be advisable to include an isotonic agent, such as, for example, sugars, sodium chloride or combinations thereof.

Liquid preparations for oral administration can take the form of, for example, solutions, syrups or suspensions, or they can be presented as a dry product for constitution with water or other suitable vehicle before use. In one embodiment, the liquid preparations can be formulated for administration with fruit juice. Such liquid preparations can be prepared by conventional means with pharmaceutically acceptable additives such as suspending agents (for example, sorbitol syrup, cellulose derivatives or hydrogenated edible fats); emulsifying agents (for example, lecithin or acacia); non-aqueous vehicles (for example, almond oil, oily esters, ethyl alcohol or fractionated vegetable oils); and preservatives (for example, methyl or propyl-p-hydroxybenzoates, benzoate or sorbate).

In certain embodiments, the composition is a medical food. A medical food product is a food product formulated to be consumed or administered enterally. Such a food product is usually used under the supervision of a physician for the specific dietary management of a target disease, such as those described herein. In some instances, such a medical food composition is specially formulated and processed (as opposed to a naturally occurring foodstuff used in a natural state) for a patient in need of the treatment (e.g., human patients who suffer from illness or who requires use of the product as a major active agent for alleviating a disease or condition via specific dietary management). In some examples, a medical food composition described herein is not one of those that would be simply recommended by a physician as part of an overall diet to manage the symptoms or reduce the risk of a disease or condition.

Any of the medical food compositions described herein, comprising a polymorphic form of sodium benzoate and at least one carrier (e.g., those described herein), can be in the form of a liquid solution; powder, bar, wafer, a suspension in an appropriate liquid or in a suitable emulsion, as detailed below. The at least one carrier, which can be either naturally-occurring or synthetic (non-naturally occurring), would confer one or more benefits to the sodium benzoate and co-former in the composition, for example, stability, bioavailability, and/or bioactivity. Any of the carriers described herein may be used for making the medical food composition. In some embodiments, the medical food composition may further comprise one or more additional ingredients selected from the group including, but not limited to natural flavors, artificial flavors, major trace and ultra-trace minerals, minerals, vitamins, oats, nuts, spices, milk, egg, salt, flour, lecithin, xanthan gum and/or sweetening agents. The medical food composition may be placed in a suitable container, which may further comprise at least an additional therapeutic agent such as those described herein.

In certain embodiments, the polymorph described herein is provided in an effective amount in the pharmaceutical composition. In certain embodiments, the effective amount is a therapeutically effective amount (e.g., amount effective for treating and/or reducing the risk for a neuropsychiatric disorder in a subject in need thereof). In certain embodiments, the neuropsychiatric disorder is a neurological disorder, e.g., Alzheimer's disease. In certain embodiments, the effective amount is a prophylactically effective amount (e.g., amount effective for preventing a neuropsychiatric disorder in a subject in need thereof).

Pharmaceutical compositions described herein can be prepared by any method known in the art of pharmacology. In general, such preparatory methods include bringing the polymorphic form of sodium benzoate described herein (i.e., the "active ingredient") into association with a carrier or excipient, and/or one or more other accessory ingredients, and then, if necessary and/or desirable, shaping, and/or packaging the product into a desired single- or multi-dose unit.

Pharmaceutical compositions can be prepared, packaged, and/or sold in bulk, as a single unit dose, and/or as a plurality of single unit doses. A "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage, such as one-half or one-third of such a dosage.

Relative amounts of the active ingredient, the pharmaceutically acceptable excipient, and/or any additional ingredients in a pharmaceutical composition described herein will vary, depending upon the identity, size, and/or condition of the subject treated and further depending upon the route by which the composition is to be administered. The composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates described herein are mixed with solubilizing agents such as Cremophor®, alcohols, oils, modified oils, glycols, polysorbates, cyclodextrins, polymers, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension, or emulsion in a nontoxic parenterally acceptable diluent or solvent, for example, as a solution in 1,3-butanediol. Among the acceptable vehicles and solvents that can be employed are water, Ringer's solution, U.S.P., and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form may be accomplished by dissolving or suspending the drug in an oil vehicle.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar, calcium carbonate, potato or tapioca starch, alginic acid, certain silicates, sodium starch glycolate (SSG), croscarmellose, crospovidone, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as colloidal silicon dioxide, talc, calcium stearate, magnesium stearate, solid polyethylene glycols, sodium lauryl sulfate, and mixtures thereof. In the case of capsules, tablets, and pills, the dosage form may include a buffering agent such as sodium citrate, and chitosan. In addition, the pharmaceutically acceptable excipient described herein can be single species or a mixture of multiple species of tannic acid, or a pharmaceutically acceptable salt thereof.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the art of pharmacology. They may optionally comprise opacifying agents and can be of a composition that they release the active ingredient(s)

only, or preferentially, in a certain part of the digestive tract, optionally, in a delayed manner. Examples of encapsulating compositions which can be used include polymeric substances and waxes. Solid compositions of a similar type can be employed as fillers in soft and hard-filled gelatin capsules using such excipients as lactose or milk sugar as well as high molecular weight polyethylene glycols and the like.

The active ingredient can be in a micro-encapsulated form with one or more excipients as noted above. The solid dosage forms of tablets, dragees, capsules, pills, and granules can be prepared with coatings and shells such as enteric coatings, release controlling coatings, and other coatings well known in the pharmaceutical formulating art. In such solid dosage forms the active ingredient can be admixed with at least one inert diluent such as sucrose, lactose, or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the digestive tract, optionally, in a delayed manner. Examples of encapsulating agents which can be used include, but are not limited to, polymeric substances and waxes.

Although the descriptions of pharmaceutical compositions provided herein are mainly directed to pharmaceutical compositions which are suitable for administration to humans, such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

The polymorphic forms provided herein are typically formulated in dosage unit form for ease of administration and uniformity of dosage. It will be understood, however, that the total daily usage of the compositions described herein will be decided by a physician within the scope of sound medical judgment. The specific therapeutically effective dose level for any particular subject or organism will depend upon a variety of factors including the disease being treated and the severity of the disorder; the activity of the specific active ingredient employed; the specific composition employed; the age, body weight, general health, sex, and diet of the subject; the time of administration, route of administration, and rate of excretion of the specific active ingredient employed; the duration of the treatment; drugs used in combination or coincidental with the specific active ingredient employed; and like factors well known in the medical arts.

Also encompassed by the disclosure are kits (e.g., pharmaceutical packs). The kits provided may comprise a pharmaceutical composition or polymorphic form of sodium benzoate described herein and a container (e.g., a vial, ampule, bottle, syringe, and/or dispenser package, or other suitable container). In some embodiments, provided kits may optionally further include a second container comprising a pharmaceutical excipient for dilution or suspension of a pharmaceutical composition or polymorphic form of sodium benzoate described herein. In some embodiments, the pharmaceutical composition or polymorphic form of sodium benzoate described herein provided in the first container and the second container are combined to form one unit dosage form.

In certain embodiments, a kit described herein includes a first container comprising a polymorphic form or composition described herein. In certain embodiments, a kit described herein is useful in treating and/or reducing the risk for a neuropsychiatric disorder in a subject in need thereof.

In certain embodiments, a kit described herein further includes instructions for using the polymorphic form or composition included in the kit. A kit described herein may also include information as required by a regulatory agency such as the U.S. Food and Drug Administration (FDA). In certain embodiments, the information included in the kits is prescribing information. In certain embodiments, the kits and instructions provide for treating and/or reducing the risk for a neuropsychiatric disorder in a subject in need thereof. A kit described herein may include one or more additional pharmaceutical agents described herein as a separate composition.

Method of Synthesis

Described herein are a number of exemplary methods for preparing the polymorphic forms of sodium benzoate described herein:

General Method 1: Crystallization Via Evaporation in Saturated Solution.

Crystallization was carried out by evaporation in a saturated solution. Excess amount of sodium benzoate was dissolved in a solvent. The solution was filtered and the filtrate was evaporated to dryness to afford a new polymorphic form of sodium benzoate.

In one aspect, the synthesis of a polymorphic form of sodium benzoate includes a first step of dissolving an excess amount of sodium benzoate in a single or mixed suitable solvent to form a saturated solution at ambient pressure and temperature. The saturated solution may then be filtrated using a filter having a pore size ranging from 5 to 100 m to remove insoluble components. The solution thus obtained can be evaporated for a suitable period of time under suitable conditions to allow for formation of a polymorphic form of sodium benzoate (e.g., polymorphic form No. 1 as described in Example 1 below). In certain embodiments, the solution is evaporated at ambient or reduced pressure and/or at an elevated temperature, e.g., approximately 40-110° C. In certain embodiments, the elevated temperature can range from approximately 40-90° C., approximately 40-80° C., approximately 40-70° C., or approximately 40-60° C. The polymorphic form of sodium benzoate formed from the evaporated solution can then be collected.

Suitable solvents for use in the synthesis methods described herein include, but are not limited to, polar protic solvents (e.g., methanol, ethanol, isopropanol, water), polar aprotic solvents (e.g., acetonitrile, ethyl acetate), or a mixture thereof. In certain embodiments, the solvent is methanol, ethanol, isopropanol, acetonitrile, ethyl acetate, water, or mixtures thereof.

A polar solvent refers to a solvent having a large dipole moment (e.g, approximately 1.6 D and higher). For example, polar solvents include, but are not limited to, methanol, ethanol, isobutanol, n-butanol, isopropanol, dimethyl sulfoxide (DMSO), dimethylformamide (DMF), water, acetonitrile, ethyl acetate, pyridine, or acetone.

General Method 2: Crystallization Via Cooling in Saturation Solution.

To sodium benzoate was added a single or mixed solvent at elevated temperature (50-110° C.) while stirring. The addition of solvent was halted immediately when the solution became clear. The solution was allowed to cool down while stirring. The suspension was filtered and the crystals were harvested to afford a new polymorphic form of sodium benzoate.

For example, the synthesis of a polymorphic form of sodium benzoate includes a first step of dissolving sodium benzoate in a single or mixed suitable solvent at a temperature ranging from about 50-110° C. to form a solution. Suitable solvents for use in the synthesis methods described herein include, but are not limited to, polar protic solvents (e.g., methanol, ethanol, isopropanol, water), polar aprotic solvents (e.g., acetonitrile, ethyl acetate), or a mixture thereof. In certain embodiments, the solvent is methanol, ethanol, isopropanol, acetonitrile, ethyl acetate, water, or mixtures thereof. In certain embodiments, the synthesis of a polymorphic form of sodium benzoate includes a first step of dissolving sodium benzoate in a single or mixed solvent at a temperature of 50-110° C., 50-100° C., 50-90° C., 50-80° C., 50-70° C., or 60-70° C. to form a solution. In certain embodiments, the synthesis of a polymorphic form of sodium benzoate includes a first step of dissolving sodium benzoate in a single or mixed solvent at a temperature of 50° C., 60° C., 70° C., 80° C., 90° C., 100° C., or 110° C. to form a solution.

In certain embodiments, the heated solution of dissolved sodium benzoate is then cooled to ambient temperature (e.g., about 20 to 25° C.) while stirring. In certain embodiments, the cooled solution is then placed at ambient temperature to allow formation of a polymorphic form of sodium benzoate. In certain embodiments, the polymorphic form of sodium benzoate formed by placement at ambient temperature in the third step is collected. In certain embodiments, the polymorphic form of sodium benzoate formed by placement at ambient temperature is collected by filtration using a filter having a pore size ranging from 5 to 100 μm.

General Method 3: Transformation in High Humidity Conditions

Sodium benzoate was stored in conditions with greater than 90% RH (relative humidity) to afford a new polymorphic form of sodium benzoate.

For example, the synthesis of a polymorphic form of sodium benzoate includes a first step of placing sodium benzoate at a relative humidity (RH) greater than about 90% for about 1 to 10 days, during which a polymorphic form of sodium benzoate forms. In certain embodiments, the first step includes placing sodium benzoate at a RH of about 90%, about 91%, about 92%, about 93%, about 94%, about 95%, about 96%, about 97%, about 98%, about 99%, or about 100%. In certain embodiments, the first step includes placing sodium benzoate at a relative humidity (RH) greater than about 90% for about 1 to 10 days, about 1 to 9 days, about 1 to 8 days, about 1 to 7 days, about 1 to 6 days, about 1 to 5 days, about 1 to 4 days, about 1 to 3 days, or about 1 to 2 days. The polymorphic form of sodium benzoate formed in the first step may then be collected.

General Method 4: Transformation in Slurry Solution

The slurry solution of sodium benzoate in a solvent was mixed for a certain period of time to afford a new polymorphic form of sodium benzoate.

For example, the synthesis of a polymorphic form of sodium benzoate includes a first step of preparing a slurry of a first polymorphic form of sodium benzoate in a single or mixed solvent. Suitable solvents for use in the synthesis methods described herein include, but are not limited to, polar protic solvents (e.g., methanol, ethanol, isopropanol, butanol, isobutanol, methyl-1-butanol, or water), polar aprotic solvents (e.g., acetonitrile, ethyl acetate, dioxane, methyl ethyl ketone, methyl t-butyl ether, toluene, or tetrahydrofuran), or a mixture thereof. In certain embodiments, the solvent is methanol, ethanol, isopropanol, butanol, acetonitrile, ethyl acetate, methyl ethyl ketone, tetrahydrofunan, water, or mixtures thereof. In certain embodiments, the synthesis of a polymorphic form of sodium benzoate includes a second step of stirring the slurry for 6 hours to 10 days, 6 hours to 9 days, 6 hours to 8 days, 6 hours to 7 days, 6 hours to 6 days, 6 hours to 5 days, 6 hours to 4 days, 6 hours to 3 days, 6 hours to 2 days, 6 hours to 1 day, 6 hours to 20 hours, 6 hours to 15 hours, 6 hours to 10 hours, or 6 hours to 8 hours, during which a polymorphic form of sodium benzoate forms. In certain embodiments, in the second step, the slurry is stirred for 6 hours, 7 hours, 8 hours, 9 hours, 10 hours, 12 hours, 14 hours, 15 hours, 18 hours, 20 hours, 22 hours, 1 day, 2 days, 3 days, 4 days, 5 days, 6 days, 7 days, 8 days, or 9 days. In certain embodiments, the synthesis of a polymorphic form of sodium benzoate includes a third step of collecting the polymorphic form of sodium benzoate formed in the second step. The polymorphic form of sodium benzoate may be collected by filtration using a filter having a pore size ranging from 5 to 100 μm.

General Method 5: Crystallization Via Precipitation by Anti-Solvent

Sodium benzoate was fully dissolved in a solvent, followed by the gradual addition of an anti-solvent. The slurry was stirred for a certain period of time and the crystals were harvested to afford a new polymorphic form of sodium benzoate.

For example, the synthesis of a polymorphic form of sodium benzoate includes a first step of dissolving sodium benzoate in a single or mixed solvent to form a solution. Suitable solvents for use in the synthesis methods described herein include, but are not limited to, polar protic solvents (e.g., methanol, ethanol, isopropanol, water), polar aprotic solvents (e.g., acetonitrile, ethyl acetate), or a mixture thereof. In certain embodiments, the solvent is methanol, ethanol, isopropanol, acetonitrile, ethyl acetate, water, or mixtures thereof. The solution of dissolved sodium benzoate may then be mixed with an anti-solvent to form a slurry, wherein the volume ratio between the anti-solvent and the solution in the first step is about 4:1 to 15:1. Suitable solvents for use in the synthesis methods described herein include, but are not limited to, polar protic solvents (e.g., methanol, ethanol, isopropanol, butanol, water), polar aprotic solvents (e.g., acetonitrile, acetone, ethyl acetate, tetrahydrofuran, methyl ethyl ketone), nonpolar solvents (toluene, tetrahydrofuran, methyl t-butyl ether), or a mixture thereof. In certain embodiments, the anti-solvent is acetone, acetonitrile, butanol, dimethylformamide, dimethyl sulfoxide, dioxane, ethyl acetate, isobutanol, isopropanol, methyl ethyl ketone, methyl-1-butanol, methyl t-butyl ether, tetrahydrofuran, toluene, or mixtures thereof. In certain embodiments, in the second step of mixing dissolved sodium benzoate solution with anti-solvent to form a slurry, the volume ratio between the anti-solvent and the solution in the first step is about 4:1 to 15:1, about 4:1 to 13:1, about 4:1 to 11:1, about 4:1 to 9:1, about 4:1 to 7:1, or about 4:1 to 5:1. In certain embodiments, in the second step, the volume ratio between the anti-solvent and the solution in the first step is about 4:1, about 5:1, about 6:1, about 7:1, about 8:1, about 9:1, or about 10:1.

In certain embodiments, the slurry may be then stirred at ambient pressure and temperature for about 2-10 days, during which a polymorphic form of sodium benzoate forms. In certain embodiments, the slurry is stirred at ambient pressure and temperature for about 2-8 days, about 2-7 days, about 2-6 days, about 2-5 days, about 2-4 days, or about 2-3 days. In certain embodiments, the slurry is stirred at ambient pressure and temperature for about 2 days, about 3 days, about 4 days, about 5 days, about 6 days, about 7 days, about 8 days, about 9 days, or about 10 days. The polymorphic form of sodium benzoate formed in the third step by stirring the slurry of sodium benzoate solution is then collected. In certain embodiments, the polymorphic form of sodium benzoate is collected by filtration using a filter having a pore size ranging from 5 to 100 am.

Alternatively, the synthesis of a polymorphic form of sodium benzoate includes a first step of preparing a slurry of the polymorphic form of sodium benzoate in a single or mixed solvent in the presence of about 2-10% of water by volume. Suitable solvents for use in the synthesis methods described herein include, but are not limited to, polar protic solvents (e.g., methanol, ethanol, isopropanol, or butanol), polar aprotic solvents (e.g., acetonitrile, ethyl acetate, dioxane, methyl ethyl ketone, methyl t-butyl ether, toluene, or tetrahydrofuran), or a mixture thereof. In certain embodiments, the solvent is methanol, ethanol, isopropanol, acetonitrile, ethyl acetate, or mixtures thereof. In certain embodiments, the first step comprises preparing a slurry of the polymorphic form of sodium benzoate in the presence of less than about 10%, less than about 9%, less than about 8%, less than about 7%, less than about 6%, less than about 5%, less than about 4%, less than about 3%, or less than about 2%, of water by volume. In certain embodiments, the synthesis of a polymorphic form of sodium benzoate includes a second step of stirring the slurry at ambient pressure and temperature for about 2 to 10 days, during which a polymorphic form of sodium benzoate forms. In certain embodiments, the second step comprises stirring the slurry at ambient pressure and temperature for about 2 to 10 days, about 2-8 days, about 2-7 days, about 2-6 days, about 2-5 days, about 2-4 days, or about 2-3 days. In certain embodiments, the second step comprises stirring the slurry at ambient pressure and temperature for about 2 days, about 3 days, about 4 days, about 5 days, about 6 days, about 7 days, about 8 days, about 9 days, or about 10 days. In certain embodiments, the synthesis of a polymorphic form of sodium benzoate includes a third step of collecting the polymorphic form of sodium benzoate formed by stirring the slurry of sodium benzoate. In certain embodiments, the polymorphic form of sodium benzoate is collected by filtration using a filter having a pore size ranging from 5 to 100 µm.

Exemplary methods for preparing the polymorphic forms of sodium benzoate described herein are provided in the Examples below.

Methods of Treatment

The present disclosure provides methods of treating and/or reducing the risk for a neuropsychiatric disorder, in a subject in need thereof, the methods comprising administering to the subject an effective amount (e.g., therapeutically effective amount) of a polymorph, or any of the compositions described herein (e.g., comprising a polymorph of sodium benzoate or a combination of sodium benzoate and clozapine).

Another aspect of the present disclosure relates to methods of preventing a neuropsychiatric disorder in a subject in need thereof, the methods comprising administering to the subject an effective amount (e.g., prophylactically effective amount) of a polymorph, or composition thereof, described herein.

The polymorphic forms and compositions described herein are useful in treating and/or preventing neuropsychiatric disorders. In certain embodiments, the neuropsychiatric disorder is schizophrenia. In certain embodiments, the neuropsychiatric disorder is a psychotic disorder. In certain embodiments, the neuropsychiatric disorder is Alzheimer's disease. In certain embodiments, the neuropsychiatric disorder is dementia including frontotemporal dementia. In certain embodiments, the neuropsychiatric disorder is mild cognitive impairment. In certain embodiments, the neuropsychiatric disorder is benign forgetfulness. In certain embodiments, the neuropsychiatric disorder is closed head injury. In certain embodiments, the neuropsychiatric disorder is autistic spectrum disorder including Asperger's disorder. In certain embodiments, the neuropsychiatric disorder is an attention deficit hyperactivity disorder. In certain embodiments, the neuropsychiatric disorder is obsessive compulsive disorder. In certain embodiments, the neuropsychiatric disorder is a tic disorder. In certain embodiments, the neuropsychiatric disorder is a childhood learning disorder. In certain embodiments, the neuropsychiatric disorder is premenstrual syndrome. In certain embodiments, the neuropsychiatric disorder is depression, including dysthymia and bereavement. In certain embodiments, the neuropsychiatric disorder is bipolar disorder including bipolar I and II disorders. In certain embodiments, the neuropsychiatric disorder is an anxiety disorder including panic and phobic disorders. In certain embodiments, the neuropsychiatric disorder is post-traumatic stress disorder. In certain embodiments, the neuropsychiatric disorder is chronic pain. In certain embodiments, the neuropsychiatric disorder is an eating disorder including bulimia and anorexia. In certain embodiments, the neuropsychiatric disorder is an addiction disorder including substance dependence or abuse. In certain embodiments, the neuropsychiatric disorder is a personality disorder. In certain embodiments, the neuropsychiatric disorder is Parkinson's disorder. In certain embodiments, the neuropsychiatric disorder is Huntington's disorder. In certain embodiments, the neuropsychiatric disorder is multiple sclerosis. In certain embodiments, the neuropsychiatric disorder is amyotrophic lateral sclerosis.

In certain embodiments, the method described herein further includes administering to the subject an additional pharmaceutical agent. In certain embodiments, the method described herein further includes contacting the biological sample with an additional pharmaceutical agent. In certain embodiments, the method described herein further includes contacting the tissue with an additional pharmaceutical agent. In certain embodiments, the method described herein further includes contacting the cell with an additional pharmaceutical agent.

The polymorphic forms and compositions provided herein can be administered by any route, including enteral (e.g., oral), parenteral, intravenous, intramuscular, intraarterial, intramedullary, intrathecal, subcutaneous, intraventricular, transdermal, interdermal, subcutaneous, intradermal, rectal, intravaginal, intraperitoneal, topical (as by powders, ointments, creams, and/or drops). Specifically contemplated routes are oral administration, intravenous administration (e.g., systemic intravenous injection), regional administration via blood and/or lymph supply, and/or direct administration to an affected site. In general, the most appropriate route of administration will depend upon a variety of factors including the nature of the agent (e.g., its stability in the environment of the gastrointestinal tract), and/or the condition of the subject (e.g., whether the subject is able to tolerate oral administration).

The exact amount of a polymorphic form required to achieve an effective amount will vary from subject to subject, depending, for example, on species, age, and general condition of a subject, severity of the side effects or disorder, identity of the particular polymorph, mode of administration, and the like. An effective amount may be included in a single dose (e.g., single oral dose) or multiple doses (e.g., multiple oral doses). In certain embodiments, when multiple doses are administered to a subject or applied to a biological sample, tissue, or cell, any two doses of the multiple doses include different or substantially the same amounts of a polymorphic form of sodium benzoate described herein. In certain embodiments, when multiple doses are administered to a subject or applied to a biological sample, tissue, or cell, the frequency of administering the multiple doses to the subject or applying the multiple doses to the tissue or cell is three doses a day, two doses a day, one dose a day, one dose every other day, one dose every third day, one dose every week, one dose every other week, one dose monthly or one dose every other month. In certain embodiments, the frequency of administering the multiple doses to the subject or applying the multiple doses to the tissue or cell is one dose per day. In certain embodiments, the frequency of administering the multiple doses to the subject or applying the multiple doses to the tissue or cell is two doses per day. In certain embodiments, when multiple doses are administered to a subject or applied to a biological sample, tissue, or cell, the duration between the first dose and last dose of the multiple doses is one day, two days, four days, one week, two weeks, three weeks, one month, two months, three months, four months, six months, nine months, one year, two years, three years, four years, five years, seven years, ten years, fifteen years, twenty years, or the lifetime of the subject, biological sample, tissue, or cell. In certain embodiments, the duration between the first dose and last dose of the multiple doses is three months, six months, or one year. In certain embodiments, the duration between the first dose and last dose of the multiple doses is the lifetime of the subject, biological sample, tissue, or cell. In certain embodiments, a dose (e.g., a single dose, or any dose of multiple doses) described herein includes independently between 1 mg and 3 mg, between 3 mg and 10 mg, between 10 mg and 30 mg, between 30 mg and 100 mg, between 100 mg and 300 mg, between 300 mg and 1,000 mg, or between 1 g and 10 g, inclusive, of a polymorphic form of sodium benzoate described herein. In certain embodiments, a dose described herein includes independently between 3 mg and 10 mg, inclusive, of a polymorphic form of sodium benzoate described herein. In certain embodiments, a dose described herein includes independently between 10 mg and 30 mg, inclusive, of a polymorphic form of sodium benzoate described herein. In certain embodiments, a dose described herein includes independently between 30 mg and 100 mg, inclusive, of a polymorphic form of sodium benzoate described herein. In certain embodiments, a dose described herein includes independently between 100 mg and 300 mg, inclusive, of a polymorphic form as described herein. In certain embodiments, a dose described herein includes independently between 300 mg and 1000 mg, inclusive, of a polymorphic form of sodium benzoate described herein.

Dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

A polymorphic form or composition, as described herein, can be administered in combination with one or more additional pharmaceutical agents (e.g., therapeutically and/or prophylactically active agents) useful in treating and/or reducing the risk for a neuropsychiatric disorder. The polymorphic forms or compositions can be administered in combination with additional pharmaceutical agents that improve their activity (e.g., activity (e.g., potency and/or efficacy) in treating and/or reducing the risk for a neuropsychiatric disorder in a subject in need thereof), improve bioavailability, improve safety, reduce drug resistance, reduce and/or modify metabolism, inhibit excretion, and/or modify distribution in a subject, biological sample, tissue, or cell. It will also be appreciated that the therapy employed may achieve a desired effect for the same disorder, and/or it may achieve different effects. In certain embodiments, a pharmaceutical composition described herein including a polymorphic form of sodium benzoate described herein and an additional pharmaceutical agent shows a synergistic effect that is absent in a pharmaceutical composition including one of the polymorph and the additional pharmaceutical agent, but not both.

The polymorph or composition can be administered concurrently with, prior to, or subsequent to one or more additional pharmaceutical agents, which may be useful as, e.g., combination therapies in treating and/or reducing the risk for a neuropsychiatric disorder in a subject. Pharmaceutical agents include therapeutically active agents. Pharmaceutical agents also include prophylactically active agents. Pharmaceutical agents include small organic molecules such as drug compounds or polymorphic forms thereof (e.g., compounds approved for human or veterinary use by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, antibodies, small molecules linked to proteins such as antibodies, glycoproteins, steroids, nucleic acids, DNAs, RNAs, nucleotides, nucleosides, oligonucleotides, antisense oligonucleotides, lipids, hormones, vitamins, and cells. In certain embodiments, the additional pharmaceutical agent is a pharmaceutical agent useful in treating and/or reducing the risk for a neuropsychiatric disorder in a subject. In certain embodiments, the additional pharmaceutical agent is a pharmaceutical agent approved by a regulatory agency (e.g., the US FDA, EMA, China FDA) for treating and/or reducing the risk for a neuropsychiatric disorder in a subject. In certain embodiments, the additional pharmaceutical agent is a neuropharmaceutical selected from the group consisting of cariprazine, brexpiprazole, iloperidone, pimavanserin, luradisone, butyrophenone, phenothiazine, fluphenazine, perphenazine, prochlorperazine, thioridazine, trifluoperazine, mesoridazine, promazine, triflupromazine, levomepromazine, promethazine, thioxanthene, chlorprothixene, flupenthixol, thiothixene, zuclopenthixol, clozapine, olanzapine, risperidone, quetiapine, ziprasidone, amisulpride, asenapine, paliperidone, aripiprazole, lamotrigine, tetrabenazine, cannabidiol, LY2140023, droperidol, pimozide, butaperazine, carphenazine, eemoxipride, piperacetazine, sulpiride, acamprosate, tetrabenazine, vilazodone, levomilnacipran, vortioxetine fluoxetine, paroxetine, escitalopram, citalopram, sertraline, fluvoxamine, venlafaxine, milnacipram, duloxetine, mirtazapine, mianserin, reboxetine, bupropion, amitriptyline, nortriptiline, protriptyline, desipramine, trimipramine, amoxapine, clomipramine, desipramine, doxepin, isocarboxazid, tranylcypromine, selegiline, trazodone, nefazodone, phenelzine, lamatrogine, lithium, topiramate, gabapentin, carbamazepine, oxacarbazepine, valporate, maprotiline, mirtazapine, brofaromine, gepirone, moclobemide, isoniazid, iproniazid, a statin, an amphetamine, modafinil, desoxyn, methamphetamine, cocaine, arecoline, dexmethylphenidate, dextroamphetamine, methylphenidate, lisdexamfetamine dimesylate, mixed salts amphetamine, atomoxetine, clonidine hydrochloride, guanfacine hydrochloride, arecoline, pemoline, donepezil, tacrine, rivastigmine, memantine, physostigmine, lithium salts, nicotine, arecoline, huperzine alpha, riluzole, vitamin C, vitamin E, carotenoids, tannic acid, and *Ginkgo biloba* extract.

Each additional pharmaceutical agent may be administered at a dose and/or on a time schedule determined for that pharmaceutical agent. The additional pharmaceutical agents may also be administered together with each other and/or with the polymorph or composition described herein in a single dose or administered separately in different doses. The particular combination to employ in a regimen will take into account compatibility of the polymorph described herein with the additional pharmaceutical agent(s) and/or the desired therapeutic and/or prophylactic effect to be achieved. In general, it is expected that the additional pharmaceutical agent(s) in combination be utilized at levels that do not exceed the levels at which they are utilized individually. In some embodiments, the levels utilized in combination will be lower than those utilized individually.

In certain embodiments, the additional pharmaceutical agent is an agent for treating and/or reducing the risk for a neuropsychiatric disorder. In certain embodiments, the polymorphic forms of sodium benzoate described herein or pharmaceutical compositions can be administered in combination with a therapy for treating and/or reducing the risk for a neuropsychiatric disorder.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

In order that the present disclosure may be more fully understood, the following examples are set forth. The synthetic and biological examples described in this application are offered to illustrate the polymorphic forms, compounds, compositions, and methods provided herein and are not to be construed in any way as limiting their scope.

Example 1: Preparation of Polymorphic Form #1 of Sodium Benzoate 199.93 mg of sodium benzoate was placed in a flask and 4 mL of methanol was added to dissolve the sodium benzoate. Unless otherwise indicated, commercially available sodium benzoate was purchased from Merck, Formosa Laboratories Inc., or Sigma Aldrich, and solvents were purchased from vendors such as Acros, Merck, and Sigma Aldrich. The solution thus formed was kept stirring for 10 min and then filtered to remove any insoluble ingredients. The filtrate was evaporated by rotary evaporation to form solid sodium benzoate in a polymorphic form. The solid obtained was analyzed by XRPD, TGA, and DSC as described below.

Thermogravimetric Analysis (TGA).

Total weight loss was obtained on a TA Instrument TGA Model Q500. The sample was heated in an opened aluminum pan at the heating rate of 10° C./min up to the final temperature.

Differential Scanning Calorimetry.

Thermal analysis was performed using a TA Instrument DSC Model Q200. The sample was heated in an aluminum pan at the heating rate of 10° C./min with 50 mL/min nitrogen purge up to the final temperature.

X-Ray Powder Diffractometry.

The solid samples were determined by X-ray powder diffractometer (Bruker D8 advance) equipped with LynxEye detector. The instrument parameters were listed below. Scan: 3° (2θ) to 40° (2θ); Increment: 0.02° (2θ); Scan speed: 0.1-0.3 sec/step (FIGS. 1-24); or scan speed: approximately 1 sec/step (FIGS. 25-28); Voltage: 40 KV; Current: 40 mA; Rotation: On; Sample hold: Zero-background sample holder.

The results obtained from the TGA, DSC and X-ray powder diffractometry assays are provided in FIGS. 1-28.

Example 2: Preparation of Polymorphic Form #2

2.005 mg of commercially available sodium benzoate was placed in a round bottom flask followed by the addition of 150 mL of acetonitrile. The suspension thus formed was kept stirring for 2 days and filtered to collect solid sodium benzoate thus formed. The solid sodium benzoate, in a polymorphic form, was also analyzed by XRPD, TGA, and DSC and the results are shown in FIGS. 4-6.

Example 3: Preparation of Polymorphic Form #3

2.006 g of commercially available sodium benzoate was placed in a round bottom flask and 150 mL of isobutanol was added. The suspension thus formed was kept stirring for 6 days and filtered afterwards. The solid sodium benzoate thus formed was collected and analyzed by XRPD, TGA, and DSC. The results are shown in FIGS. 7-9.

Example 4: Preparation of Polymorphic Form #4

2.182 g of commercially available sodium benzoate was placed in a round bottom flask followed by the addition of 4 mL of water. 20 mL of isopropyl alcohol was then added gradually and the resulting suspension was kept stirring for 3 days and filtered to collect the solid thus formed. The solid collected was analyzed by XRPD, TGA, and DSC. The results are shown in FIGS. 10-12.

Example 5: Preparation of Polymorphic Form #5

106.6 mg commercially available sodium benzoate was placed in a round bottom flask and 70 mL of a mixed solvent containing ethanol and ethyl acetate (1:1) was added at 70° C. The resulting solution was kept stirring for 10 min, then cooled to ambient temperature and stirred overnight to allow for formation of solid sodium benzoate in a polymorphic form, which was collected by filtration and analyzed by XRPD, TGA, and DSC. The results are shown in FIGS. 13-15.

Example 6: Preparation of Polymorphic Form #6

2.006 g of commercially available sodium benzoate was placed in a round bottom flask and 40 mL of methanol was added to dissolve the sodium benzoate. 120 mL of acetonitrile was added gradually and the suspension thus formed was kept stirring. After 2 days, the suspension was filtered and solid obtained was analyzed by XRPD, TGA, and DSC. The results are shown in FIGS. 16-18.

Example 7: Alternative Preparation of Polymorphic Form #4

1-2 mg of either one of the new polymorphic forms #1-3, 5, or 6 disclosed herein was slurried in 0.5 mL of acetonitrile with approximately 6% of water to allow formation of the new polymorphic form #4. It was thus demonstrated that among all new polymorphic forms afforded, polymorphic form #4 was the most thermodynamically stable.

Example 8: Scale-Up Preparation of Polymorphic Form #4

50 g of commercially available sodium benzoate (purchased from Merck) was placed in a round bottom flask followed by the addition of 92 mL of water. 688 mL of isopropyl alcohol was slowly added and the resulting suspension was kept stirring with an overhead stirrer for 4 days and filtered to collect 22.3 g of the solid.

Figure 19:
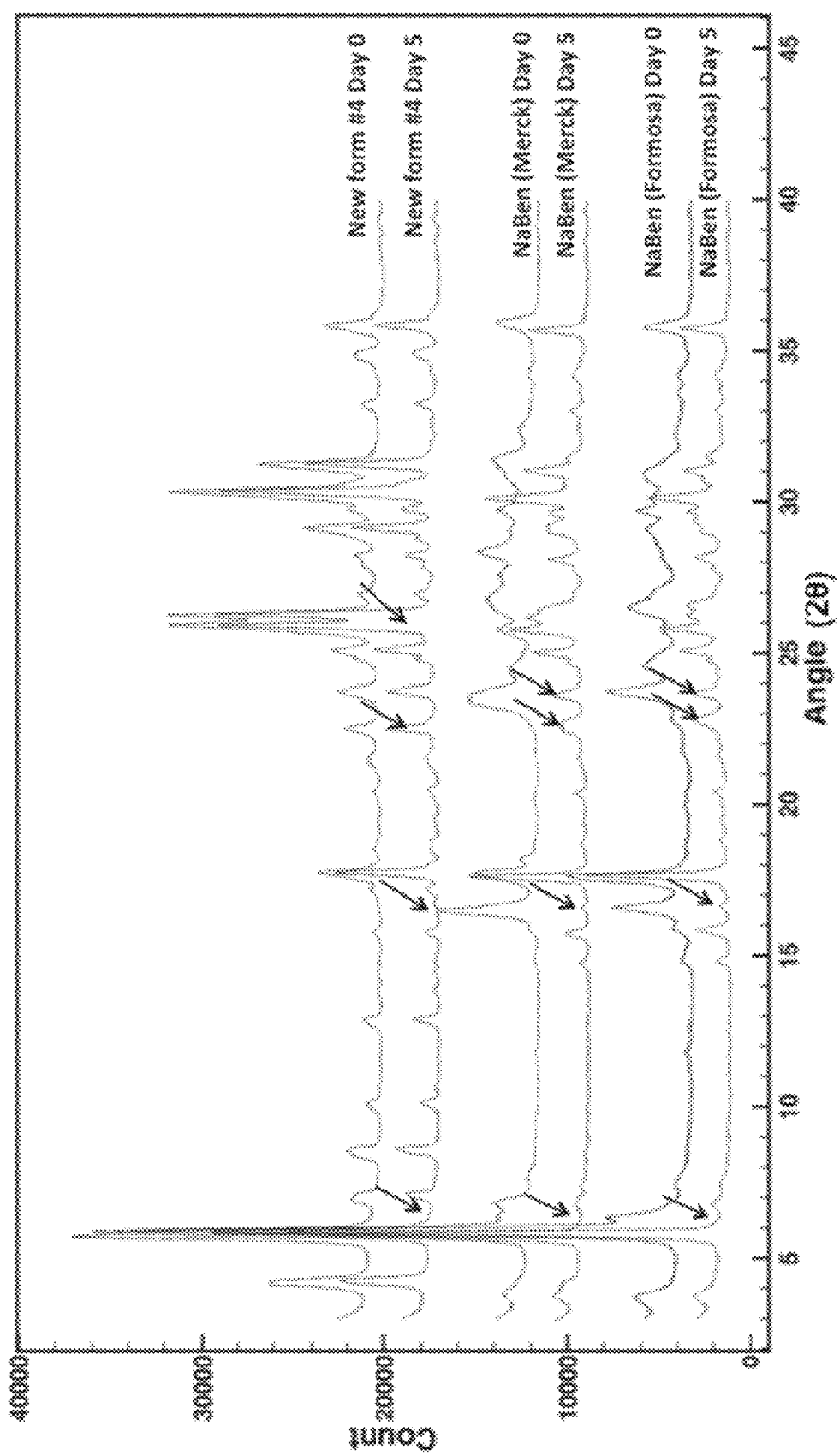
FIG. 19 shows the X-ray powder diffraction (XRPD) of sodium benzoate (NaBen) from Merck, Formosa Laboratories, and new polymorphic form #4 under high humidity conditions of over 90% relative humidity for 5 days. The XRPD of the sodium benzoate from Merck and Formosa Laboratories show changes in XRPD under these high humidity conditions, but the XRPD of polymorphic form #4 of sodium benzoate from Example 7 does not show such changes in XRPD.

Example 9: Stability Test of Polymorphic Form #4 Under High Humidity Condition 500 mg of each of sodium benzoate from Merck and Formosa Laboratories, and polymorphic form #4 was stored under high humidity condition (>90% RH) for 5 days and analyzed by XRPD. The results indicated that, after 5 days, there were significant changes to the XRPD patterns with peaks at a reflection angle 2θ of approximately 6.2, 16.5, and 24.5 degrees and the appearance of a new peak at 22.9 degrees of sodium benzoate from Merck and Formosa Laboratories, while no change to the XRPD pattern of new polymorphic form #4 was observed. The results are shown in FIG. 19. It was thus shown that polymorphic #4 was more stable than the tested commercial sodium benzoate products under high humidity conditions.

Figure 20:
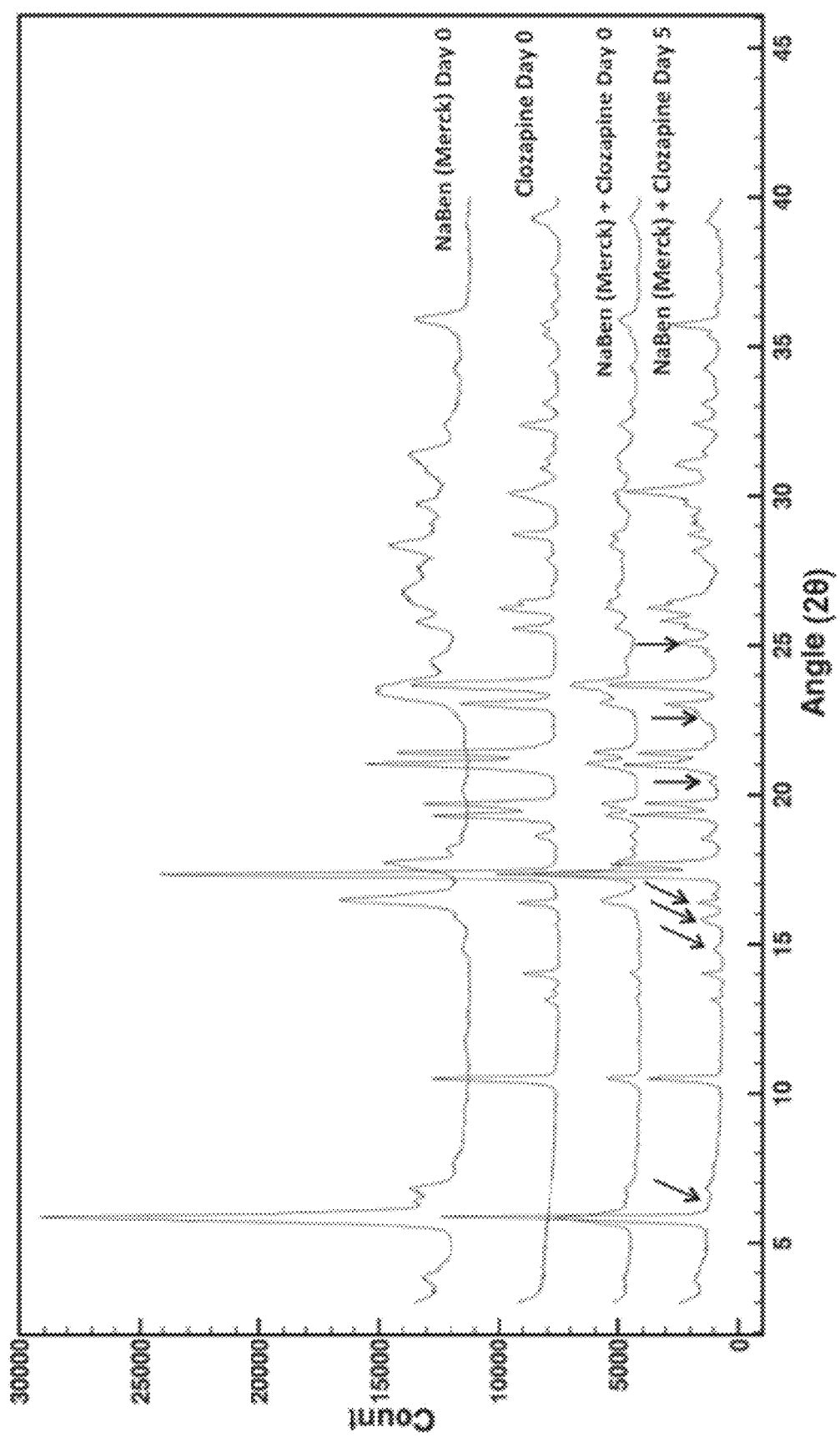
FIG. 20 shows the changes of X-ray powder diffraction (XRPD) of sodium benzoate (NaBen) from Merck combined with clozapine (300 mg) under high humidity conditions (of over 90% relative humidity) for 5 days.
Figure 21:
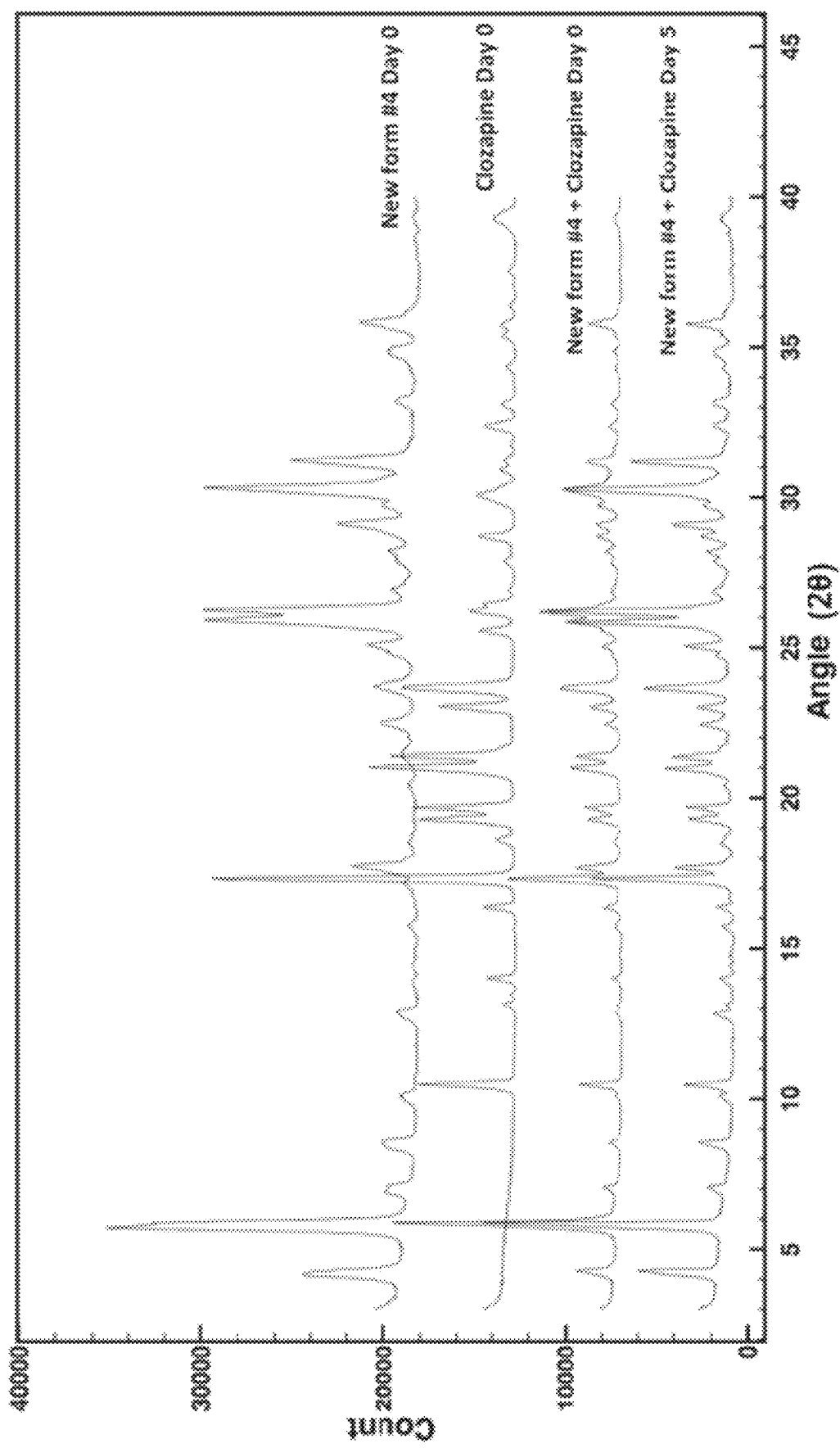
FIG. 21 shows no change of the X-ray powder diffraction (XRPD) of new polymorphic form #4 combined with clozapine (300 mg) under high humidity conditions (of over 90% relative humidity) for 5 days.

Example 10: Stability Test of Polymorphic Form #4 Combined with Clozapine Under High Humidity Conditions 500 mg of each of sodium benzoate from Merck and new polymorphic form #4 combined with 300 mg of clozapine was stored under high humidity condition (>90% RH) for 5 days and analyzed by XRPD. The results revealed that, after 5 days, there were significant changes to the XRPD pattern with peaks at a reflection angle 2θ of approximately 6.2, 14.9, 15.9, 16.5, 20.5, 22.6, and 25.1 degrees and the appearance of a new peak at 22.9 degrees of sodium benzoate from Merck combined with clozapine. No change to the XRPD pattern of new polymorphic form #4 combined with clozapine was observed. The results are shown in FIGS. 20-21. It was thus illustrated that, when combined with a second therapeutic agent, the use of polymorphic form #4 was more suitable than the tested commercial sodium benzoate products.

Figure 22:
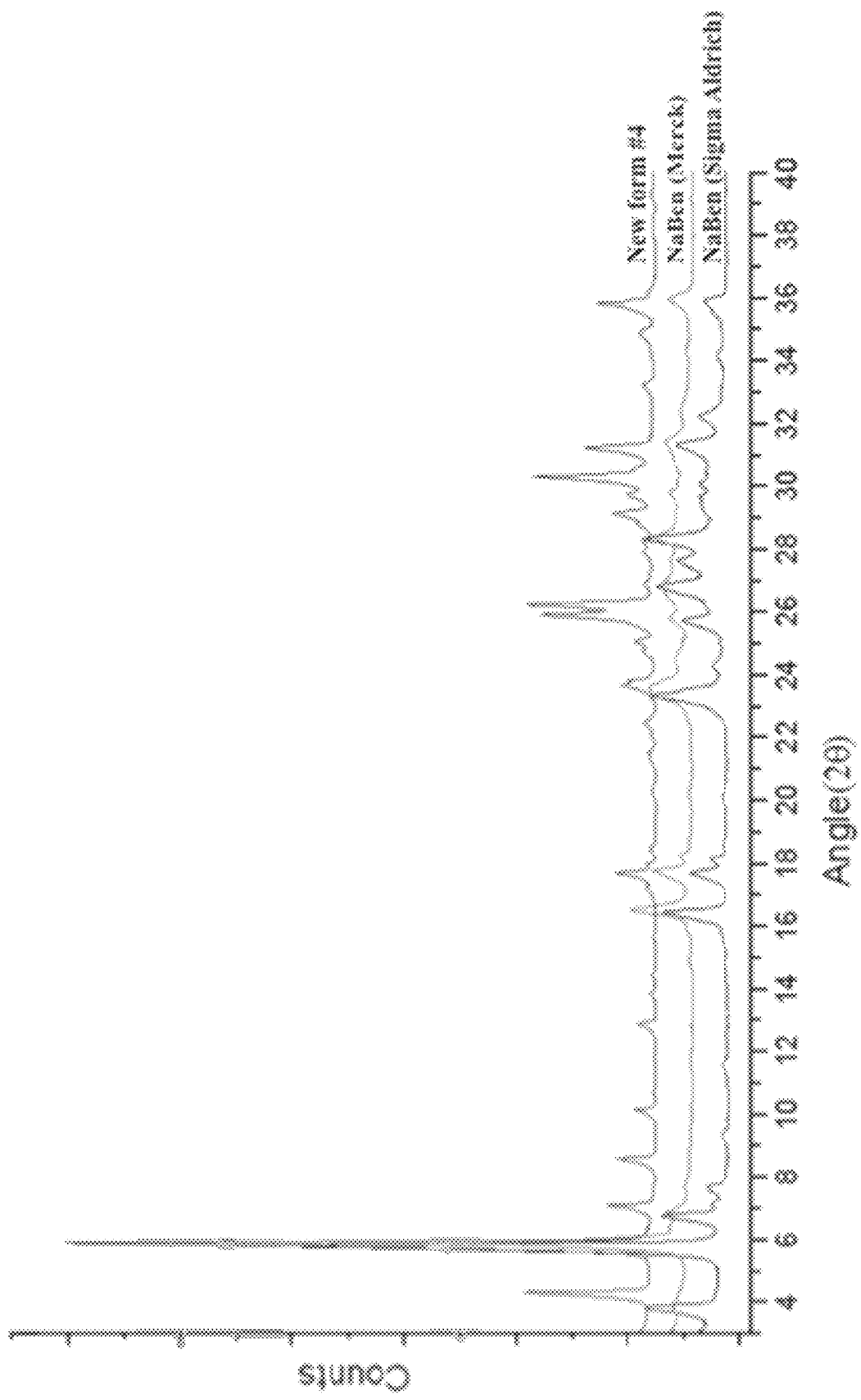
FIG. 22 shows the X-ray powder diffraction (XRPD) of new polymorphic form #4, sodium benzoate (NaBen) from Merck, and sodium benzoate (NaBen) from Sigma Aldrich.
Figure 23:
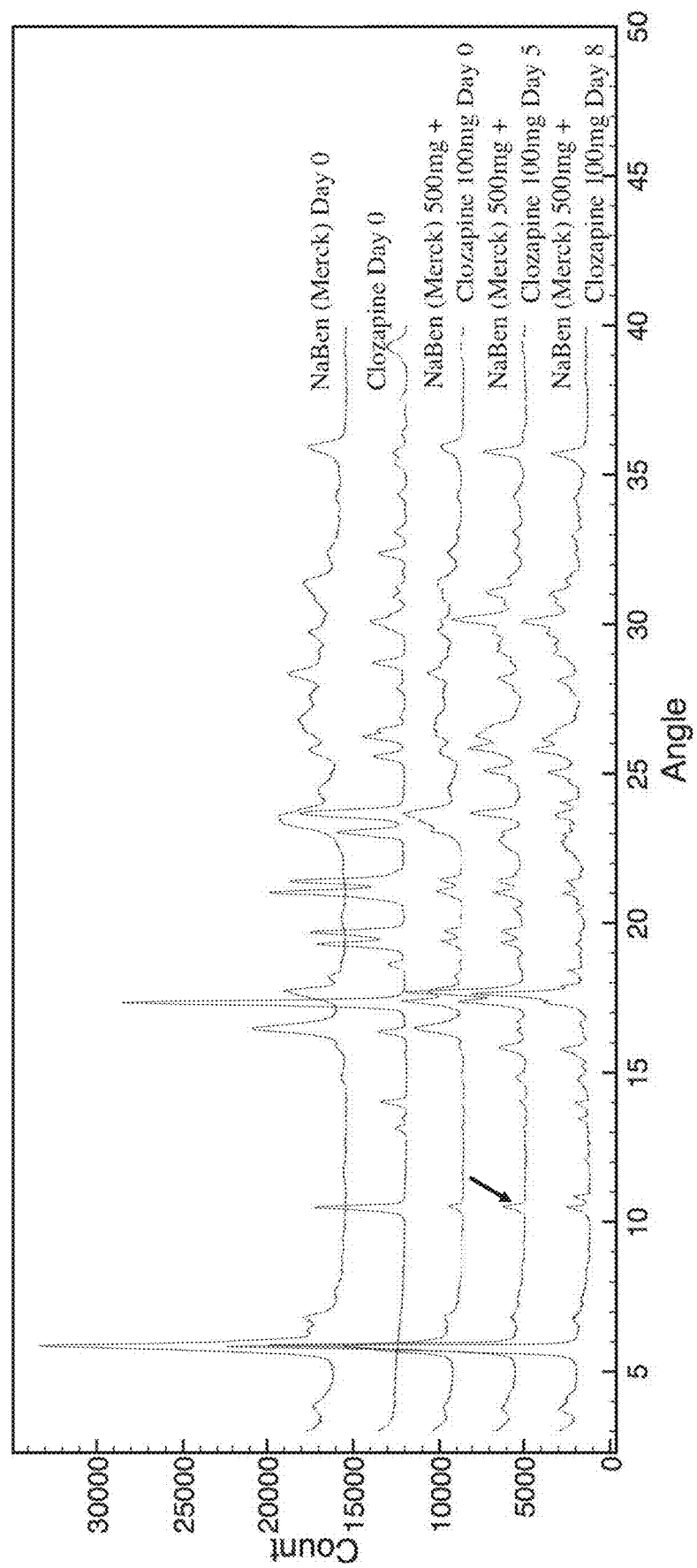
FIG. 23 shows the changes of X-ray powder diffraction (XRPD) of sodium benzoate (NaBen) from Merck combined with clozapine (100 mg) under high humidity conditions (>90% RH, room temperature) for 8 days.
Figure 24:
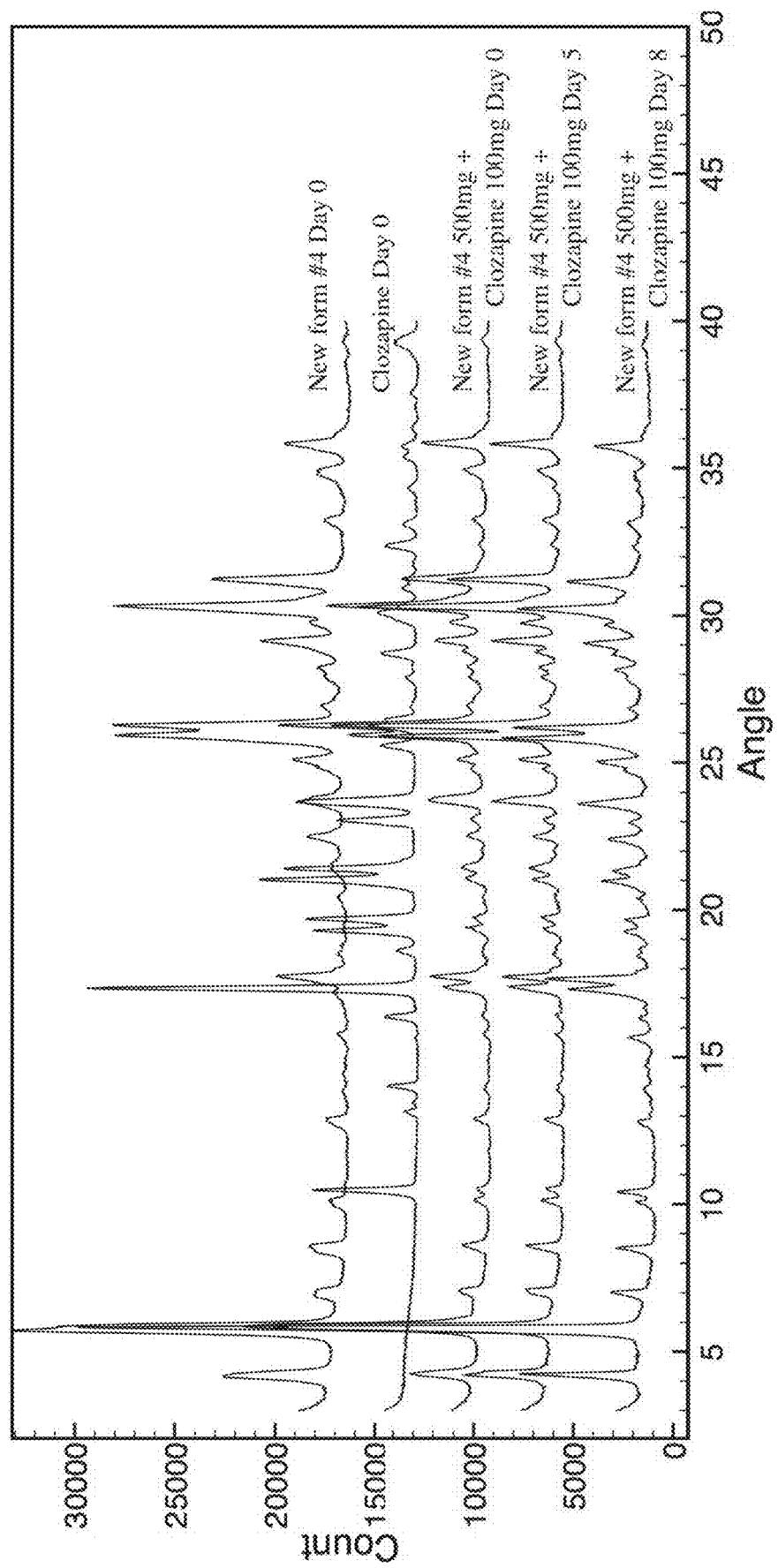
FIG. 24 shows no change of the X-ray powder diffraction (XRPD) of polymorphic form #4 of sodium benzoate combined with clozapine (100 mg) under high humidity conditions (>90% RH, room temperature) for 8 days.

Example 11: Further Comparison of Polymorphic Form #4 with Sodium Benzoate from Merck and Sigma Aldrich New polymorphic form #4, sodium benzoate from Merck, and sodium benzoate from Sigma Aldrich were analyzed and compared by XRPD. The results, as shown in FIG. 22, indicated that the XRPD patterns of these two commercial sodium benzoate samples from Merck and Sigma Aldrich much overlapped with each other. New polymorphic form #4 was found to be the most thermodynamically stable polymorphic form of sodium benzoate, compared to the less thermodynamically stable polymorphic form from the commercially available sodium benzoate (Merck, Formosa Laboratories, and Sigma Aldrich).

Example 12: Solubility of Polymorphic Form #4 in Water

To around 1 g of each of new polymorphic form #4, sodium benzoate from Merck, and sodium benzoate from Sigma Aldrich in a vial was added water till maximum solubility was reached. The results showed that the maximum water solubility of new polymorphic form #4 (666 mg/ml) was higher than that of sodium benzoate from Merck (500 mg/ml) and Sigma Aldrich (454 mg/ml). Therefore, the solubility of the polymorphic form #4 of sodium benzoate of the invention is about 1.3 to 1.5 times higher than the commercially available sodium benzoate products.

Example 13: Stability Tests of Commercially Available Sodium Benzoate and Polymorphic Form #4 of Sodium Benzoate 1. Stress Testing Under High Humidity Conditions Another stability test was held with 500 mg of commercially available sodium benzoate from Merck or the polymorphic form #4 of sodium benzoate of the invention independently combined with 100 mg of clozapine, stored under high humidity condition (>90% RH), at room temperature for 8 days. On day 8, the XRPD pattern of the combination of commercially available sodium benzoate and clozapine showed an additional new peak at 11°, as shown by an arrow in FIG. 23-24. However, the additional peak at 11° was not found in the XRPD pattern of the combination of the polymorphic form #4 of sodium benzoate of the invention and clozapine. In the following experiments, the appearance of the peak at 11° was deemed as deterioration of clozapine polymorph in the combination of clozapine and commercially available sodium benzoate.

2. Stability of Combination of Polymorphic Form #4 of Sodium Benzoate of the Invention and Clozapine, and Other Excipients Since humidity is a stability issue for the combination of sodium benzoate compound and clozapine, several excipients were chosen to test their influences on the stability under high humidity condition (>90% RH, room temperature). The results are shown in the Tables 1 and 2.

Comparing with boric acid, sodium alginate has a better effect in stabilizing the combination of sodium benzoate (purchased from Merck) and clozapine (see Table 1). In addition, the 11° peak, which indicates the deterioration of the combination of sodium benzoate (purchased from Merck) and clozapine, does not appear until day 30 when high dose of chitosan (60 mg) or sodium citrate (60 mg) further added in the composition (see Table 2).

TABLE 1

Stability test results under high humidity condition (>90% RH, room temperature) of sodium benzoate and clozapine mixed with different excipients

| | Sample | | | |
|---|---|---|---|---|
| | 1 | 2 | 3 | 4 |
| Sodium benzoate (Merck) (mg) | 500 | 500 | 500 | 500 |
| Clozapine (mg) | 300 | 300 | 300 | 300 |
| Boric acid (mg) | 20 | 40 | — | — |
| Sodium alginate (mg) | — | — | 20 | 40 |
| TOTAL (mg) | 820 | 840 | 820 | 840 |
| Appearance of peak at 11° | Day 5 | Day 5 | Day 11 | Day 11 |

TABLE 2

Stability test results under high humidity condition (>90% RH, room temperature) of sodium benzoate and clozapine mixed with different excipients

| | Sample | | | | | | | | | |
|---|---|---|---|---|---|---|---|---|---|---|
| | 5 | 6 | 7 | 8 | 9 | 10 | 11 | 12 | 13 | 14 |
| Sodium benzoate (Merck) (mg) | 500 | 500 | 500 | 500 | 500 | 500 | 500 | 500 | 500 | 500 |
| Clozapine (mg) | 300 | 300 | 300 | 300 | 300 | 300 | 300 | 300 | 300 | 300 |
| Sodium alginate (mg) | 40 | 40 | 40 | 40 | 40 | 40 | 40 | 40 | 40 | 40 |
| Chitosan (mg) | 30 | 60 | — | — | — | — | — | — | — | — |
| Sodium hyaluronate (mg) | — | — | 7.5 | 15 | — | — | — | — | — | — |
| Sodium stearyl fumarate (mg) | — | — | — | — | 7.5 | 15 | — | — | — | — |
| Sodium citrate (mg) | — | — | — | — | — | — | 30 | 60 | — | — |
| Sodium starch glycolate (mg) | — | — | — | — | — | — | — | — | 30 | 60 |
| TOTAL (mg) | 870 | 900 | 847.5 | 855 | 847.5 | 855 | 870 | 900 | 870 | 900 |
| Appearance of peak at 11° | Day 20 | Day 30 | Day 20 | Day 13 | Day 11 | Day 11 | Day 20 | Day 30 | Day 11 | Day 11 |

Example 14: Preparation of Tablets Comprising Sodium Benzoate Compound and Clozapine 1. Wet Granulation The active ingredients (e.g. any of the sodium benzoate compounds and clozapine) and excipients were milled and sieved by a 40-mesh screen separately. The milled and sieved powders were mixed in a mortar. 75% ethanol, which was used as a binder solution, was added slowly into the mortar to perform wet granulation. The obtained wet mass was screened by a 20-mesh screen for coarse screening. Then the moist granules were dried at 50° C. for 3 hours. The dried granules were further sieved twice: (1) by a 40-mesh screen, and the granules larger than 40-mesh were kept; and (2) by a 20-mesh screen, and the granules passed the screen were kept. After sieving with the 40- and 20-mesh screens, the granules having sizes between 20 and 40 meshes were obtained. The resulted granules were then blended with magnesium stearate as a lubricant for approximately 3 minutes, and the blend was compressed by ZP01 Single punch tablet press (Taizhou Liming Pharmaceutical Machinery Co., Ltd.) into tablets. The obtained tablets were weighted, and their hardness, friability, disintegration time and dissolution release time were tested.

2. Hardness Test

The obtained tablets were subjected to a hardness test, and the power (kg) needed for breaking the tested tablet was recorded. The harness of tablets was controlled between 5 to 10 kg.

3. Friability Test

Ten tablets were put in a tablet friability apparatus and rotated at 25±1 rpm for 100 circles. The test was determined as failed if any of the tested tablets were broken. When the tablets were not broken, they would be weighted to calculate their weight loss (%). The weight loss (%) should be lower than 1%.

4. Disintegration Test

Six tablets were put into water at 37±2° C. The test was determined as failed if these tablets were not disintegrated within 30 minutes. The disintegration time (minutes) of these tablets was recorded.

5. Dissolution Test

The dissolution test was performed based on the USP method for dissolution of clozapine. Six tablets were added into the dissolution medium (acetate buffer, pH 4.0) and subjected to the dissolution test. The volume of the dissolution medium was 500 mL and the rotation speed was of 100 rpm. The test was determined as failed if these tablets were not dissolved within 30 minutes. The dissolution time (minutes) of these tablets was recorded.

Both sodium alginate and sodium citrate enhance the immediate release effect, but the tablet formulations 1-2, which comprise sodium alginate and sodium citrate, flaked off during the dissolution test, and the addition of sodium starch glycolate (SSG) as a disintegrating agent improved this defect, as shown in Table 3.

TABLE 3

Tablet formulations

| | Formulation | | |
|---|---|---|---|
| | 1 | 2 | 3 |
| Sodium benzoate (Merck) (mg) | 500 | 500 | 500 |
| Clozapine (mg) | 300 | 200 | 300 |
| Sodium alginate (mg) | 60 | 60 | 60 |
| Sodium citrate (mg) | 60 | 60 | 60 |
| Magnesium stearate (mg) | 10 | 10 | 10 |
| Sodium starch glycolate (mg) | — | — | 90 |
| TOTAL (mg) | 930 | 830 | 1020 |
| Hardness (kg) | 7~8 | 13-14 | 10 |
| Friability (%) | 0.73 | 0.51 | 0.6 |
| Disintegration time (min) | 20 | 19 | 13 |
| Dissolution release time (min) | <30 | <30 | 15 |

Tablet formulations comprising the combination of clozapine and commercially available sodium benzoate (purchased from Merck) or the polymorphic form #4 sodium benzoate obtained from Example 4, as shown in Tables 4 and 5, were then examined. The results showed that the tablets comprising the polymorphic form #4 of sodium benzoate of the invention had shorter disintegration time and dissolution release time, which were benefit for preparation of immediate release dosage form of drugs.

TABLE 4

Tablet formulations comprising commercially available sodium benzoate and clozapine

| Formulation | 4 | 5 | 6 | 7 | 8 | 9 | 10 | 11 |
|---|---|---|---|---|---|---|---|---|
| Sodium benzoate (Merck) (mg) | 500 | 500 | 500 | 500 | 500 | 500 | 500 | 500 |
| Clozapine (mg) | 300 | 300 | 300 | 300 | 200 | 200 | 200 | 200 |
| Sodium alginate (mg) | 50 | 70 | 50 | 70 | 50 | 70 | 50 | 70 |
| Sodium citrate (mg) | 50 | 70 | 60 | 60 | 50 | 70 | 60 | 60 |
| Magnesium stearate (mg) | 5 | 15 | 10 | 10 | 5 | 15 | 10 | 10 |
| Sodium starch glycolate (mg) | 80 | 100 | 100 | 80 | 80 | 100 | 100 | 80 |
| TOTAL (mg) | 985 | 1055 | 1020 | 1020 | 885 | 955 | 920 | 920 |
| Hardness (kg) | 9~10 | 9~10 | 9~10 | 9~10 | 10~11 | 10~11 | 10~11 | 10~11 |
| Friability (%) | 0.42 | 0.50 | 0.76 | 0.53 | 0.36 | 0.38 | 0.40 | 0.34 |
| Disintegration time (min) | 16~17 | 16~18 | 13~14 | 15~16 | 11~12 | 11~12 | 11~12 | 13~14 |
| Dissolution release time (min) | 14~15 | 15~16 | 13~14 | 15~16 | 11~12 | 12~13 | 11~12 | 13~14 |

TABLE 5

Tablet formulations comprising the polymorphic form #4 of sodium benzoate of the invention and clozapine

| Formulation | 12 | 13 | 14 | 15 | 16 | 17 | 18 | 19 |
|---|---|---|---|---|---|---|---|---|
| Polymorphic form #4 of sodium benzoate (mg) | 500 | 500 | 500 | 500 | 500 | 500 | 500 | 500 |
| Clozapine (mg) | 300 | 300 | 300 | 300 | 200 | 200 | 200 | 200 |
| Sodium alginate (mg) | 50 | 70 | 50 | 70 | 50 | 70 | 50 | 70 |
| Sodium citrate (mg) | 50 | 70 | 60 | 60 | 50 | 70 | 60 | 60 |
| Magnesium stearate (mg) | 5 | 15 | 10 | 10 | 5 | 15 | 10 | 10 |
| Sodium starch glycolate (mg) | 80 | 100 | 100 | 80 | 80 | 100 | 100 | 80 |
| TOTAL (mg) | 985 | 1055 | 1020 | 1020 | 885 | 955 | 920 | 920 |
| Hardness (kg) | 6~7 | 6~7 | 6~7 | 6~7 | 6~7 | 6~7 | 6~7 | 6~7 |
| Friability (%) | 0.68 | 0.71 | 0.67 | 0.63 | 0.52 | 0.69 | 0.66 | 0.78 |
| Disintegration time (min) | 5~6 | 6~7 | 5~6 | 6~7 | 5~6 | 6~7 | 5~6 | 5~6 |
| Dissolution release time (min) | 8~9 | 8~9 | 8~9 | 8~9 | 7~8 | 8~9 | 8~9 | 8~9 |

Example 15: Comparative Features of Various Polymorph Forms of Sodium Benzoate Polymorph forms #1, 2, 3 and 6 ("polymorph forms #1-3 and 6") were prepared following the methods disclosed above (Examples 1, 2, 3, and 6, respectively).

Another sodium benzoate polymorph was prepared following the conditions disclosed in Howard et al. (*Crystal Growth and Design*, Vol. 9, pages 3964-3975; see, e.g., Section 2.4 and FIG. 4) ("polymorph #7"), which differ from the conditions used for preparing Forms #1-3 and 6 in at least the time frame for polymorph formation, solvent used for dissolving sodium benzoate, etc. Specifically, Howard discloses a sodium benzoate polymorph prepared over approximately 40 hours by: antisolvent crystallization performed using sodium benzoate in pure water with an initial concentration of 545 mg/mL; heating the system from 20 to 25° C. and kept at 25° C. until all the crystals dissolved, resulting in a clear solution; then adding propan-2-ol (IPA) was then added using a dosing rate within the range 0.3-2 g/min, reaching a final volume ratio of IPA/water of 5:1. Howard, Section 2.4.

Polymorph forms #1-3 and 6 involve a process of preparation comprising: (i) dissolving sodium benzoate in a polar solvent that is not purely water (e.g., either methanol, acetonitrile, or isobutanol; or acetonitrile followed by addition of methanol) to form a slurry, (ii) stirring the slurry for approximately 10 minutes to approximately 6 days (e.g., 10 minutes, 2 days, or 6 days (in contrast with the 40 hours for preparing polymorph #7)), and (iii) filtering and collecting the polymorphic form of sodium benzoate thus formed. The Howard polymorph is prepared using a final solvent ratio of IPA/water of 5:1, which is different from the polar solvents used for preparing polymorph forms #1-3 and 6 (shown in Examples 1, 2, 3, and 6, respectively).

Figure 29:
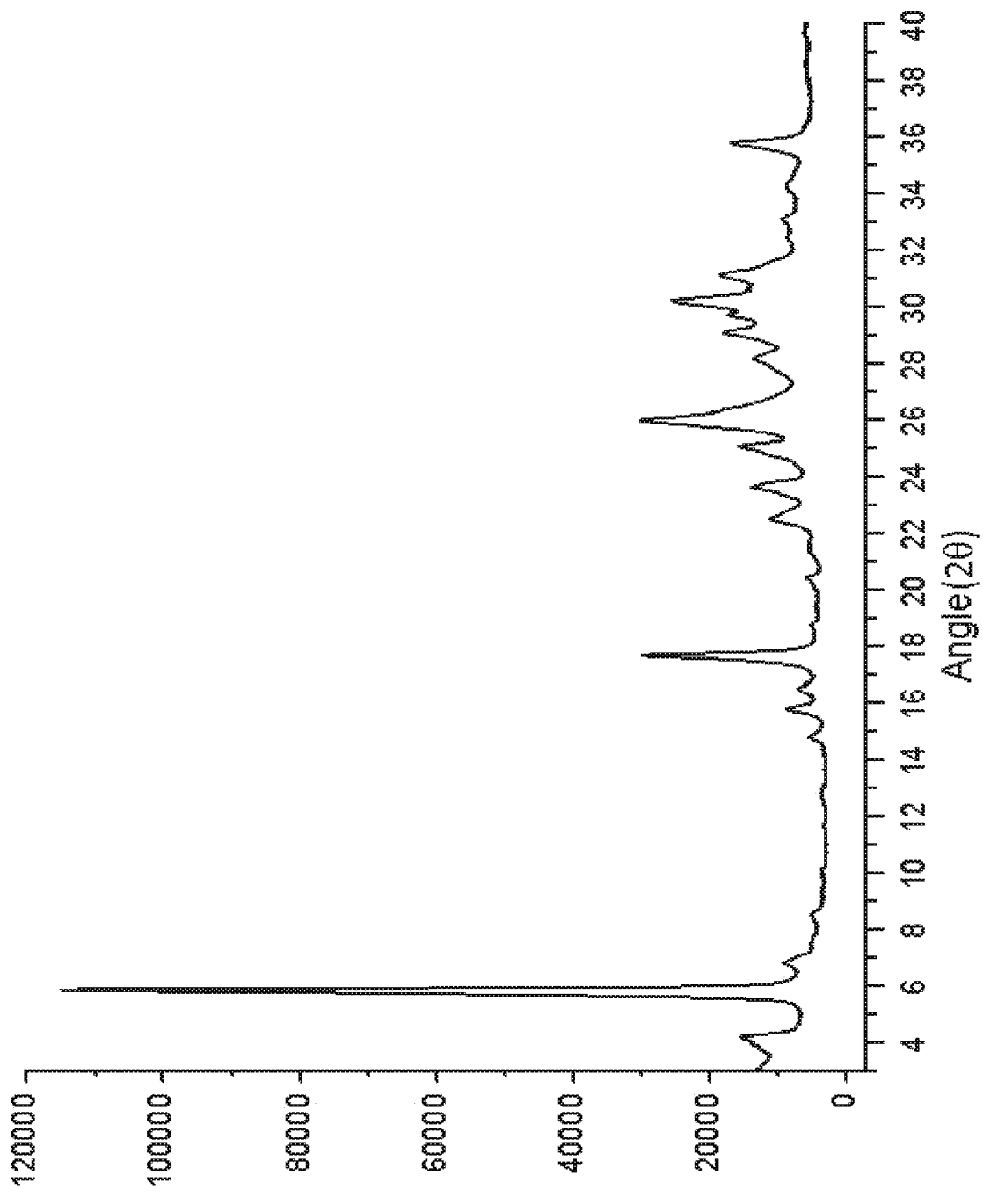
FIG. 29 shows the X-ray powder diffraction (XRPD) of a sodium benzoate polymorph was prepared following the conditions disclosed in Howard et al. (*Crystal Growth and Design*, Vol. 9, pages 3964-3975; see, e.g., Section 2.4 and FIG. 4), with peaks (°) of: 4.2, 5.8, 6.8, 8.5, 10.0, 11.7, 12.8, 14.8, 15.7, 16.4, 17.6, 18.7, 19.4, 20.4, 21.2, 22.5, 23.6, 25.0, 25.9, 28.1, 29.0, 29.7, 30.2, 31.1, 32.4, 33.0, 34.2, and 35.7; wherein the X-ray diffraction pattern is determined by a period of a scan speed of about 1.0 second per step.

XRPD patterns of polymorph forms #1-3 and 6, obtained using a period of a scan speed of about 1.0 second per step, were different from the XRPD pattern of the different polymorph obtained under the same XRPD scan speed conditions in Howard prepared using conditions of Section 2.4 and FIG. 4. A comparison of the XRPD patterns of polymorph forms #1-3 and 6 with polymorph #7 of Howard is shown in Tables 6, 7, 8, and 9 below, all obtained under the same XRPD scan speed conditions (using a period of a scan speed of about 1.0 second per step). Specifically, the peaks of the XRPD pattern for polymorph #1 are shown below in Table 6, and the XRPD pattern is shown in FIG. 25. The peaks of the XRPD pattern for polymorph #2 are shown below in Table 7, and the XRPD pattern is shown in FIG. 26. The peaks of the XRPD pattern for polymorph #3 are shown below in Table 7, and the corresponding XRPD pattern is shown in FIG. 27. The peaks of the XRPD pattern for polymorph #3 are shown below in Table 8, and the corresponding XRPD pattern is shown in FIG. 27. The peaks of the XRPD pattern for polymorph #6 are shown below in Table 9, and the corresponding XRPD pattern is shown in FIG. 28. The peaks of the XRPD pattern for polymorph #7 are shown below in Tables 6, 7, 8, and 9, and the XRPD pattern for polymorph #7 is shown in FIG. 29.

TABLE 6

XRPD Peaks in Angle (2θ)

| | |
|---|---|
| Polymorph Form #1 | 3.6, 4.2, 5.9, 6.8, 7.5, 8.5, 9.2, 11.1, 11.7, 12.4, 14.9, 15.9, 16.6, 17.6, 18.8, 19.4, 20.4, 21.6, 22.9, 23.7, 24.7, 25.1, 25.8, 26.1, 26.6, 27.7, 28.1, 29.1, 29.4, 29.7, 30.2, 30.6, 30.9, 31.5, 32.4, 32.9, 33.6, 34.2, 35.7, 38.6, 39.6 |
| Polymorph #7 | 4.2, 5.8, 6.8, 8.5, 10.0, 11.7, 12.8, 14.8, 15.7, 16.4, 17.6, 18.7, 19.4, 20.4, 21.2, 22.5, 23.6, 25.0, 25.9, 28.1, 29.0, 29.7, 30.2, 31.1, 32.4, 33.0, 34.2, 35.7 |

TABLE 7

XRPD Peaks in Angle (2θ)

| | |
|---|---|
| Polymorph Form #2 | 3.7, 5.9, 6.8, 7.5, 8.9, 11.1, 14.9, 17.6, 22.7, 23.5, 24.8, 26.2, 26.6, 27.6, 28.3, 29.3, 30.2, 30.9, 32.2, 32.9, 34.0, 35.7, 37.8 |
| Polymorph #7 | 4.2, 5.8, 6.8, 8.5, 10.0, 11.7, 12.8, 14.8, 15.7, 16.4, 17.6, 18.7, 19.4, 20.4, 21.2, 22.5, 23.6, 25.0, 25.9, 28.1, 29.0, 29.7, 30.2, 31.1, 32.4, 33.0, 34.2, 35.7 |

TABLE 8

XRPD Peaks in Angle (2θ)

| | |
|---|---|
| Polymorph Form #3 | 3.7, 5.9, 6.3, 6.8, 7.5, 9.4, 11.7, 16.4, 17.7, 23.6, 24.5, 25.7, 26.7, 27.7, 28.4, 29.0, 29.4, 30.2, 30.4, 31.0, 31.2, 32.3, 34.2, 35.4, 35.9 |
| Polymorph #7 | 4.2, 5.8, 6.8, 8.5, 10.0, 11.7, 12.8, 14.8, 15.7, 16.4, 17.6, 18.7, 19.4, 20.4, 21.2, 22.5, 23.6, 25.0, 25.9, 28.1, 29.0, 29.7, 30.2, 31.1, 32.4, 33.0, 34.2, 35.7 |

TABLE 9

XRPD Peaks in Angle (2θ)

| | |
|---|---|
| Polymorph Form #6 | 3.7, 4.2, 5.6, 5.9, 6.6, 7.4, 8.4, 9.4, 11.2, 12.5, 14.8, 17.6, 18.6, 21.6, 22.8, 23.6, 25.1, 26.3, 26.5, 27.1, 28.2, 29.5, 30.2, 31.1, 31.3, 32.0, 33.0, 34.0, 35.7, 38.0 |
| Polymorph #7 | 4.2, 5.8, 6.8, 8.5, 10.0, 11.7, 12.8, 14.8, 15.7, 16.4, 17.6, 18.7, 19.4, 20.4, 21.2, 22.5, 23.6, 25.0, 25.9, 28.1, 29.0, 29.7, 30.2, 31.1, 32.4, 33.0, 34.2, 35.7 |

Polymorph forms #1-3 and 6, obtained using a period of a scan speed of about 1.0 second per step, have at a reflection angle 2θ of at least the characteristic XRPD peaks (°) of: approximately 3.6, 7.5, 26.6, and 29.4; which are not present in polymorph #7. Polymorph forms #1-3, obtained using a period of a scan speed of about 1.0 second per step, have at a reflection angle 2θ of at least the characteristic XRPD peaks (°) of: approximately 5.9, 6.8, 17.6, 27.6, 30.2, 30.9, and 32.3; which are not present in polymorph #7. Polymorph forms #1, 2, and 6, obtained using a period of a scan speed of about 1.0 second per step, have at a reflection angle 2θ of at least the characteristic XRPD peaks (°) of: approximately 11.1, 14.9, 26.2, 32.9, and 35.7; which are not present in polymorph #7. Polymorph forms #1 and 6, obtained using a period of a scan speed of about 1.0 second per step, have at a reflection angle 2θ of at least the characteristic XRPD peaks (°) of: approximately 12.4 and 22.9; which are not present in polymorph #7.

EQUIVALENTS AND SCOPE

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A polymorphic form of sodium benzoate, which has an X-ray diffraction pattern comprising characteristic peaks at a reflection angle 2θ of 3.7, 5.9, 6.6, 7.4, 9.4, 11.2, 12.5, 22.8, 25.1, 26.3, 28.2, 29.5, 30.2, 31.1, 31.3, 33.0, and 34.0 degrees; and wherein the X-ray diffraction pattern is determined by a period of a scan speed of about 1.0 second per step.

2. The polymorphic form of sodium benzoate of claim 1, wherein the X-ray diffraction pattern comprises characteristic peaks at a reflection angle 2θ of approximately 3.7, 4.2, 5.6, 5.9, 6.6, 7.4, 8.4, 9.4, 11.2, 12.5, 14.8, 17.6, 18.6, 21.6, 22.8, 23.6, 25.1, 26.3, 26.5, 27.1, 28.2, 29.5, 30.2, 31.1, 31.3, 32.0, 33.0, 34.0, 35.7, and 38.0 degrees.

3. A composition, comprising (i) an effective amount of the polymorphic form of sodium benzoate of claim 1, and (ii) a pharmaceutically acceptable carrier, excipient, diluent, binder, additive, filler, lubricant, or a mixture thereof.

4. The composition of claim 3, further comprising a neuropharmaceutical.

5. The composition of claim 4, wherein the neuropharmaceutical is selected from the group consisting of cariprazine, brexpiprazole, iloperidone, pimavanserin, luradisone, butyrophenone, phenothiazine, fluphenazine, perphenazine, prochlorperazine, thioridazine, trifluoperazine, mesoridazine, promazine, triflupromazine, levomepromazine, promethazine, thioxanthene, chlorprothixene, flupenthixol, thiothixene, zuclopenthixol, clozapine, olanzapine, risperidone, quetiapine, ziprasidone, amisulpride, asenapine, paliperidone, aripiprazole, lamotrigine, tetrabenazine, cannabidiol, LY2140023, droperidol, pimozide, butaperazine, carphenazine, remoxipride, piperacetazine, sulpiride, acamprosate, tetrabenazine, vilazodone, levomilnacipran, vortioxetine, fluoxetine, paroxetine, escitalopram, citalopram, sertraline, fluvoxamine, venlafaxine, milnacipram, duloxetine, mirtazapine, mianserin, reboxetine, bupropion, amitriptyline, nortriptiline, protriptyline, desipramine, trimipramine, amoxapine, clomipramine, desipramine, doxepin, isocarboxazid, tranylcypromine, selegiline, trazodone, nefazodone, phenelzine, lamatrogine, lithium, topiramate, gabapentin, carbamazepine, oxacarbazepine, valporate, maprotiline, mirtazapine, brofaromine, gepirone, moclobemide, isoniazid, iproniazid, a statin, an amphetamine, modafinil, desoxyn, methamphetamine, cocaine, arecoline, dexmethylphenidate, dextroamphetamine, methylphenidate, lisdexamfetamine dimesylate, mixed salts amphetamine, atomoxetine, clonidine hydrochloride, guanfacine hydrochloride, arecoline, pemoline, donepezil, tacrine, rivastigmine, memantine, physostigmine, lithium salts, nicotine, arecoline, huperzine alpha, selegiline, riluzole, sarcosine, vitamin C, vitamin E, carotenoids, tannic acid, and *Ginkgo biloba* extract.

6. The composition of claim 4, wherein the polymorphic form of sodium benzoate and the neuropharmaceutical in the composition are at a ratio of 1:1 to 100:1 by weight.

7. The composition of claim 4, wherein the neuropharmarceutical is clozapine, donepezil, sarcosine, or tannic acid.

8. The composition of claim 3, wherein the composition is a pharmaceutical composition, a nutraceutical composition, a health food, or a medical food.

9. The composition of claim 7, which comprises 50 to 1000 mg of the polymorphic form of sodium benzoate, 25 to 300 mg of clozapine, and a pharmaceutically acceptable excipient, wherein the composition is a pharmaceutical composition in a solid dosage form.

10. A composition, comprising (i) an effective amount of the polymorphic form of sodium benzoate of claim 2, and (ii) a pharmaceutically acceptable carrier, excipient, diluent, binder, additive, filler, lubricant, or a mixture thereof.

11. The composition of claim 10, further comprising a neuropharmaceutical.

12. The composition of claim 11, wherein the neuropharmaceutical is selected from the group consisting of cariprazine, brexpiprazole, iloperidone, pimavanserin, luradisone, butyrophenone, phenothiazine, fluphenazine, perphenazine, prochlorperazine, thioridazine, trifluoperazine, mesoridazine, promazine, triflupromazine, levomepromazine, promethazine, thioxanthene, chlorprothixene, flupenthixol, thiothixene, zuclopenthixol, clozapine, olanzapine, risperidone, quetiapine, ziprasidone, amisulpride, asenapine, paliperidone, aripiprazole, lamotrigine, tetrabenazine, cannabidiol, LY2140023, droperidol, pimozide, butaperazine, carphenazine, remoxipride, piperacetazine, sulpiride, acamprosate, tetrabenazine, vilazodone, levomilnacipran, vortioxetine, fluoxetine, paroxetine, escitalopram, citalopram, sertraline, fluvoxamine, venlafaxine, milnacipram, duloxetine, mirtazapine, mianserin, reboxetine, bupropion, amitriptyline, nortriptiline, protriptyline, desipramine, trimipramine, amoxapine, clomipramine, desipramine, doxepin, isocarboxazid, tranylcypromine, selegiline, trazodone, nefazodone, phenelzine, lamatrogine, lithium, topiramate, gabapentin, carbamazepine, oxacarbazepine, valporate, maprotiline, mirtazapine, brof aromine, gepirone, moclobemide, isoniazid, iproniazid, a statin, an amphetamine, modafinil, desoxyn, methamphetamine, cocaine, arecoline, dexmethylphenidate, dextroamphetamine, methylphenidate, lisdexamfetamine dimesylate, mixed salts amphetamine, atomoxetine, clonidine hydrochloride, guanfacine hydrochloride, arecoline, pemoline, donepezil, tacrine, rivastigmine, memantine, physostigmine, lithium salts, nicotine, arecoline, huperzine alpha, selegiline, riluzole, sarcosine, vitamin C, vitamin E, carotenoids, tannic acid, and *Ginkgo biloba* extract.

13. The composition of claim 11, wherein the polymorphic form of sodium benzoate and the neuropharmaceutical in the composition are at a ratio of 1:1 to 100:1 by weight.

14. The composition of claim 11, wherein the neuropharmarceutical is clozapine, donepezil, sarcosine, or tannic acid.

15. The composition of claim 10, wherein the composition is a pharmaceutical composition, a nutraceutical composition, a health food, or a medical food.

16. The composition of claim 14, which comprises 50 to 1000 mg of the polymorphic form of sodium benzoate, 25 to 300 mg of clozapine, and a pharmaceutically acceptable excipient, wherein the composition is a pharmaceutical composition in a solid dosage form.

\* \* \* \* \*